(12) United States Patent
Ohkawa et al.

(10) Patent No.: US 6,172,085 B1
(45) Date of Patent: Jan. 9, 2001

(54) CYCLIC ETHER COMPOUNDS AS SODIUM CHANNEL MODULATORS

(75) Inventors: Shigenori Ohkawa; Tadatoshi Hashimoto, both of Osaka; Kohji Fukatsu, Hyogo, all of (JP)

(73) Assignee: Takeda Chemical Industries, Ltd., Osaka (JP)

( * ) Notice: Under 35 U.S.C. 154(b), the term of this patent shall be extended for 0 days.

(21) Appl. No.: 09/242,067

(22) PCT Filed: Aug. 28, 1997

(86) PCT No.: PCT/JP97/03007

§ 371 Date: Feb. 8, 1999

§ 102(e) Date: Feb. 8, 1999

(87) PCT Pub. No.: WO98/08842

PCT Pub. Date: Mar. 5, 1998

(30) Foreign Application Priority Data

Aug. 29, 1996 (JP) .................................................. 8-228845
Apr. 4, 1997 (JP) .................................................. 9-086496

(51) Int. Cl.[7] ........................ C07D 405/06; A61K 31/343
(52) U.S. Cl. .................... 514/320; 514/217.03; 514/307; 514/318; 514/322; 514/417; 540/596; 546/150; 546/196; 546/199; 546/201; 546/204; 548/477
(58) Field of Search ........................... 540/596; 546/150, 546/196, 199, 201, 204; 548/477; 514/212, 217.03, 318, 307, 320, 322, 417

(56) References Cited

U.S. PATENT DOCUMENTS 5,552,552 9/1996 Ohkawa et al. ..................... 546/196

FOREIGN PATENT DOCUMENTS

483772 * 5/1992 (EP) .
06041123 * 2/1994 (JP) .

OTHER PUBLICATIONS

Ohkawa et al., 5–Aminocoumarans, J. Med. Chem., vol. 40, No. 4, pp. 559–573, 1997.*
Atwal et al., Cardioselective Anti–Ischemic ATP Sensitive Potassium Channel Openers, J. Med. Chem., vol. 36, No. 24, pp. 3971–3974, 1993.*

* cited by examiner

Primary Examiner—Mukund J. Shah
Assistant Examiner—Deepak R. Rao
(74) Attorney, Agent, or Firm—Foley & Lardner

(57) ABSTRACT

A compound of the formula:

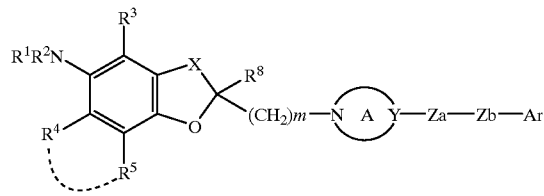

wherein $R^1$ and $R^2$ each represents hydrogen, lower alkyl which may be substituted or acyl; $R^3$, $R^4$ and $R^5$ each represents lower alkyl which may be substituted or lower alkoxy which may be substituted or $R^4$ and $R^5$ taken together represent a 5- or 6-membered carbocyclic group; $R^6$ represents lower alkyl; Ar represents an aromatic group which may be substituted; ring A represents a 5- to 8-membered nitrogen-containing heterocyclic ring which may be substituted; X represents lower alkylene which may be substituted; Y represents carbon or nitrogen; Za represents $CH_2$, $COCH_2$, $OCH_2$, $SCH_2$, $NHCH_2$, etc.; Zb represents a bond or a divalent aliphatic hydrocarbon group which may be substituted and may contain O, N or S; and m represents an integer of 1 to 3, or a salt thereof is useful for a pharmaceutical composition for modulating sodium channel.

23 Claims, No Drawings

CYCLIC ETHER COMPOUNDS AS SODIUM CHANNEL MODULATORS

This application is a 371 of PCT/JP97/03007 filed Aug. 28, 1997.

TECHNICAL FIELD

The present invention relates to novel cyclic ether compounds having very satisfactory sodium channel modulating activity, their production and use.

BACKGROUND ART

Substances which modulate the voltage-gated sodium channel are known as local anesthetics, antiarrythmic drugs, or anticonvulsants. Recent research has shown that sodium channel modulators are effective also as therapeutic drugs for central nervous system diseases and disturbances, such as ischemic central nervous disorder, brain trauma, and spinal cord injury, among others (Trends in Pharmacological Science, 16, 309–316, 1995). Ischemic or traumatic nerve injury entails retention of sodium ions in the local neurons or nerve fibers (Stroke, 20, 1377–1382, 1989) and this sodium retention leads to edematization, abnormal release of various neurotransmitters such as dopamine and glutamates (Trends in Neuroscience, 16, 415–419, 1993), and promotion of calcium ion influx by the $Na^+Ca^{2+}$ exchanger (Neuron, 12, 295–300, 1994) to thereby cause cell injuries.

While BW619C89, lifarizine, riluzole, and certain other compounds are known as sodium channel modulators (Trends in Pharmacological Science, 16, 309–316, 1995), cyclic ethers having amino groups on fused ring systems are not known.

As cyclic ethers having amino groups on fused ring systems, the following compounds, among others, are known.

1) The aminocoumaran compounds of the following formula which has inhibitory activity of lipid peroxidation (EP-A-483772 and its counterpart, JP-A-5-140142).

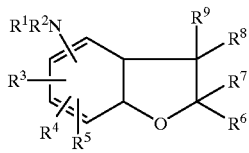

wherein $R^1$ and $R^2$ each represents hydrogen, acyl, alkoxycarbonyl, or an aliphatic or aromatic group which may be substituted; $R^3$, $R^4$ and $R^5$ each represents a hydroxy which may be acylated or an amino, alkoxy or aliphatic group which may be substituted, or two of $R^3$, $R^4$ and $R^5$ may form a carbocycle; $R^6$ and $R^7$ each represents an aliphatic group which may be substituted and at least one of $R^6$ and $R^7$ has methylene in α-position; $R^8$ and $R^9$ each represents hydrogen or an aliphatic or aromatic group which may be substituted.

2) The aminocoumaran compounds of the following formula which has inhibitory activity of lipid peroxidation (JP-A-6-41123).

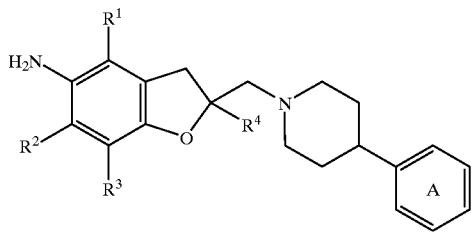

wherein $R^1$, $R^2$, $R^3$, and $R^4$ may be the same or different and each represents lower alkyl; ring A represents a benzene ring substituted by at least one substituent selected from among lower alkyl, lower alkoxy and halogen.

3) A crystalline salt of an enantiomer of 5-amino-2,4,6,7-tetramethyl-2-(4-phenylpiperidinomethyl)-2,3-dihydrobenzo[b]furan having inhibitory activity of lipid peroxidation (U.S. Pat. No. 5,552,552).

However, there is not report about the relationship of these compounds with sodium channel modulating activity.

Any sodium channel modulatory substance possessed of satisfactory sodium channel modulating activity coupled with favorable intracranial transfer kinetics and metabolic stability is expected to show good efficacy in central nervous system (CNS) diseases and disorders such as central nervous system ischemia, central nervous system trauma (e.g. brain trauma, spinal cord injury, whiplash injury, etc.), epilepsy, neurodegenerative diseases (e.g. amyotrophic lateral sclerosis (ALS), Alzheimer's disease, Huntington's chorea, Parkinson's disease, diabetic neuropathy, etc.), vascular dementia (e.g. multi-infarct dementia, Binswanger's disease, etc.), manic-depressive psychosis, depression, schizophrenia, chronic pain, trigeminal neuralgia, migraine and cerebral edema. However, no fully satisfactory modulator is available today and there has been a standing need for development of a compound possessed of satisfactory sodium channel modulating activity and qualified for use as a medicine.

The inventors of the present invention explored broadly for compounds having sodium channel modulating activity and succeeded in the creation of a novel compound which is structurally characterized in that the carbon atom in 2-position of a fused cyclic ether has been concurrently substituted by a lower alkyl group and a group of the formula:

wherein each of the symbols has the same meaning as defined below, and is of the formula:

(I)

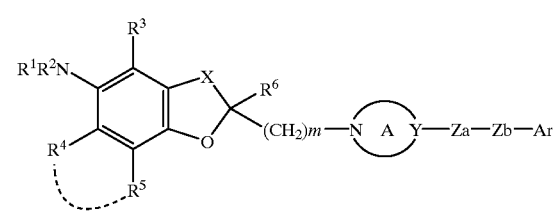

wherein

R¹ and R² each represents a hydrogen atom, a lower alkyl which may be substituted or an acyl;

R³, R⁴ and R⁵ each represents a lower alkyl which may be substituted or a lower alkoxy which may be substituted, or R⁴ and R⁵ taken together represent a 5- or 6-membered carbocyclic group;

R⁶ represents a lower alkyl;

Ar represents an aromatic group which may be substituted;

ring A represents a 5- to 8-membered nitrogen-containing heterocyclic ring which may be substituted;

X represents a lower alkylene which may be substituted;

Y represents a carbon or nitrogen atom;

Za represents a group of the formula:

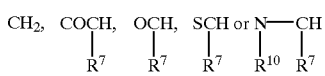

wherein

R⁷ represents a hydrogen atom or an aromatic group which may be substituted; R¹⁰ represents a hydrogen atom, a hydrocarbon group which may be substituted or an acyl;

Zb represents a bond or a divalent aliphatic hydrocarbon group which may be substituted and may contain oxygen, nitrogen or sulfur; and m represents an integer of 1 to 3, or a salt thereof [hereinafter referred to briefly as compound (I)].

They discovered surprisingly that a compound of the following formula or a salt thereof [hereinafter referred to briefly as compound (Ia)] including compound (I) has very favorable properties required of a sodium channel modulator, for example a good affinity for the sodium channel as well as high stability, and as such is fully satisfactory for use as a medicine. The present invention has been developed on the basis of the above findings:

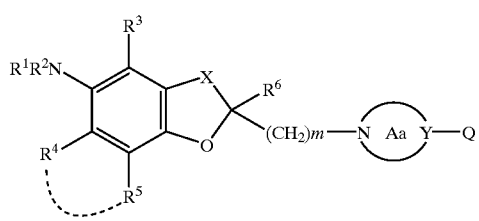

wherein Q represents a hydrogen atom, an aromatic group which may be substituted or a group of the formula:

—Zc—Ar wherein Zc represents a divalent aliphatic hydrocarbon group which may be substituted and may contain oxygen, nitrogen or sulfur; Ar has the same meaning as defined above; ring Aa represents a 5- to 8-membered nitrogen-containing heterocyclic ring which may be substituted or the corresponding fused benzologue system thereof; the other respective symbols have the same meanings as defined above.

DISCLOSURE OF INVENTION

The present invention is directed to (1) compound (I), (2) a compound of the above (1) wherein R¹ and R² each is i) a hydrogen atom, ii) a $C_{1-6}$ alkyl which may be substituted by 1 to 5 substituents selected from the group consisting of halogen, $C_{3-6}$ cycloalkyl, $C_{2-6}$ alkynyl, $C_{2-6}$ alkenyl, $C_{6-10}$ aryl, $C_{7-11}$ aralkyl, $C_{1-6}$ alkoxy, $C_{6-10}$ aryloxy, $C_{1-6}$ alkyl-carbonyl, $C_{6-10}$ aryl-carbonyl, $C_{1-6}$ alkyl-carbonyloxy, carbamoyl, amidino, imino, amino, mono-$C_{1-6}$ alkylamino, di-$C_{1-6}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, or iii) an acyl selected from the group consisting of formyl, $C_{1-6}$ alkyl-carbonyl, $C_{6-10}$ aryl-carbonyl, $C_{6-10}$ aryl-$C_{1-6}$ alkyl-carbonyl, $C_{1-6}$ alkoxy-carbonyl, $C_{6-10}$ aryl-$C_{1-6}$ alkoxy-carbonyl, $C_{1-6}$ alkylsulfonyl, $C_{6-10}$ aryl-sulfonyl which may be substituted by 1 to 3 $C_{1-6}$ alkyl and $C_{6-10}$ aryl-$C_{1-6}$ alkylsulfonyl;

R³, R⁴ and R⁵ each is i) a $C_{1-6}$ alkyl which may be substituted by 1 to 5 substituents selected from the group consisting of halogen, $C_{3-6}$ cycloalkyl, $C_{2-6}$ alkynyl, $C_{2-6}$ alkenyl, $C_{6-10}$ aryl, $C_{7-11}$ aralkyl, $C_{1-6}$ alkoxy, $C_{6-10}$ aryloxy, $C_{1-6}$ alkyl-carbonyl, $C_{6-10}$ aryl-carbonyl, $C_{1-6}$ alkyl-carbonyloxy, $C_{6-10}$ aryl-carbonyloxy, carboxy, $C_{1-6}$ alkoxy-carbonyl, carbamoyl, amidino, imino, amino, mono-$C_{1-6}$ alkylamino, di-$C_{1-6}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, or ii) a $C_{1-6}$ alkoxy which may be substituted by 1 to 5 substituents selected from the group consisting of halogen, $C_{3-6}$ cycloalkyl, $C_{2-6}$ alkynyl, $C_{2-6}$ alkenyl, $C_{6-10}$ aryl, $C_{7-11}$ aralkyl, $C_{1-6}$ alkoxy, $C_{6-10}$ aryloxy, $C_{1-6}$ alkyl-carbonyl, $C_{6-10}$ aryl-carbonyl, $C_{1-6}$ alkyl-carbonyloxy, $C_{6-10}$ aryl-carbonyloxy, carboxy, $C_{1-6}$ alkoxy-carbonyl, carbamoyl, amidino, imino, amino, mono-$C_{1-6}$ alkylamino, di-$C_{1-6}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, or R⁴ and R⁵ form, taken together with the respective adjacent carbon atoms, a 5- or 6-membered carbocyclic group selected from the group consisting of a 6-membered aromatic hydrocarbon ring and a 5- or 6-membered cycloalkene;

R⁶ is a $C_{1-6}$ alkyl;

Ar is i) a $C_{6-14}$ aryl or ii) a 5- to 10-membered aromatic heterocyclic group containing 1 to 4 hetero atoms selected from nitrogen, sulfur and oxygen in addition to carbon, each of which may be substituted by 1 to 5 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy;

ring A is a 5- to 8-membered nitrogen-containing heterocyclic ring optionally containing 1 to 4 hetero atoms selected from nitrogen, sulfur and oxygen in addition to nitrogen and carbon, which may be substituted by 1 to 3 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy;

X represents a $C_{1-6}$ alkylene which may be substituted by 1 to 3 substituents selected from the group consisting of halogen, $C_{1-6}$ alkyl, $C_{3-6}$ cycloalkyl, $C_{2-6}$ alkenyl, $C_{2-6}$ alkynyl, $C_{6-14}$ aryl, nitro, cyano, hydroxy, $C_{1-6}$ alkoxy, amino, mono-$C_{1-6}$ alkylamino, di-$C_{1-6}$ alkylamino, $C_{1-6}$ alkyl-carbonyl, $C_{6-10}$ aryloxy and oxo;

Y is i) a nitrogen atom or ii) a group of the formula:

$$>C(R^8)—$$

wherein

R$^8$ is a hydrogen atom, halogen, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl or $C_{6-10}$ aryloxy;

R$^7$ is a hydrogen atom or i) a $C_{6-14}$ aryl or ii) a 5- to 10-membered aromatic heterocyclic group containing 1 to 4 hetero atoms selected from nitrogen, sulfur and oxygen in addition to carbon, each of which may be substituted by 1 to 5 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy;

R$^{10}$ is i) a hydrogen atom, ii) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{3-6}$ cycloalkyl, $C_{2-6}$ alkynyl, $C_{2-6}$ alkenyl, $C_{6-10}$ aryl, $C_{7-11}$ aralkyl, $C_{1-6}$ alkoxy, $C_{6-10}$ aryloxy, $C_{1-6}$ alkyl-carbonyl, $C_{6-10}$ aryl-carbonyl, $C_{1-6}$ alkyl-carbonyloxy, $C_{6-10}$ aryl-carbonyloxy, carboxy, $C_{1-6}$ alkoxy-carbonyl, carbamoyl, amidino, imino, amino, mono-$C_{1-6}$ alkylamino, di-$C_{1-6}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, or iii) an acyl selected from the group consisting of formyl, $C_{1-6}$ alkyl-carbonyl, $C_{6-10}$ aryl-carbonyl, $C_{6-10}$ aryl-$C_{1-6}$ alkyl-carbonyl, $C_{1-6}$ alkoxy-carbonyl, $C_{6-10}$ aryl-$C_{1-6}$ alkoxy-carbonyl, $C_{1-6}$ alkylsulfonyl, $C_{6-10}$ arylsulfonyl which may be substituted by 1 to 3 $C_{1-6}$ alkyl and $C_{6-10}$ aryl-$C_{1-6}$ alkylsulfonyl; and Zb is a divalent aliphatic hydrocarbon group selected from the group consisting of (i) a $C_{1-8}$ alkylene, (ii) a $C_{2-8}$ alkenylene, (iii) a $C_{2-8}$ alkynylene or (iv) a group of the formula: —(CH$_2$)$_p$—M—(CH$_2$)$_q$— wherein p and q each is an integer of 0 to 8 and p+q is an integer of 1 to 8; M is O, NR$^9$, S, SO or SO$_2$, wherein R$^9$ is a hydrogen atom, $C_{1-6}$ alkyl, $C_{3-6}$ cycloalkyl, $C_{6-14}$ aryl, $C_{7-11}$ aralkyl or an acyl selected from the group consisting of formyl, $C_{1-6}$ alkyl-carbonyl, $C_{6-10}$ aryl-carbonyl, $C_{6-10}$ aryl-$C_{1-6}$ alkyl-carbonyl, $C_{1-6}$ alkoxy-carbonyl, $C_{6-10}$ aryl-$C_{1-6}$ alkoxy-carbonyl, $C_{1-6}$ alkylsulfonyl, $C_{6-10}$ arylsulfonyl which may be substituted by 1 to 3 $C_{1-6}$ alkyl and $C_{6-10}$ aryl-$C_{1-6}$ alkylsulfonyl, each of which divalent group may be substituted by 1 to 5 substituents selected from the group consisting of halogen, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{6-14}$ aryl, $C_{7-11}$ aralkyl, $C_{6-10}$ aryloxy, oxo, formyl, $C_{1-6}$ alkyl-carbonyl, $C_{6-10}$ aryl-carbonyl, $C_{6-10}$ aryl-$C_{1-6}$ alkyl-carbonyl, $C_{1-6}$ alkoxy-carbonyl, $C_{6-10}$ aryl-$C_{1-6}$ alkoxy-carbonyl, $C_{1-6}$ alkylsulfonyl, $C_{6-10}$ arylsulfonyl which may be substituted by 1 to 3 $C_{1-6}$ alkyl and $C_{6-10}$ aryl-$C_{1-6}$ alkylsulfonyl, (3) a compound of the above (1) wherein Za is a group of the formula:

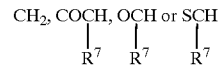

wherein R$^7$ has the same meaning as defined above, (4) a compound of the above (1) wherein R$^1$ and R$^2$ each is a hydrogen atom, (5) a compound of the above (1) wherein R$^3$, R$^4$, and R$^5$ each is $C_{1-6}$ alkyl, (6) a compound of the above (1) wherein R$^6$ is $C_{1-6}$ alkyl, (7) a compound of the above (1) wherein Ar is a $C_{6-14}$ aryl which may be substituted by 1 to 3 substituents selected from the group consisting of halogen, $C_{1-6}$ alkyl and $C_{1-6}$ alkoxy, (8) a compound of the above (1) wherein ring A is a 6-membered nitrogen-containing heterocyclic ring which may be substituted, (9) a compound of the above (1) wherein X is methylene,

(10) a compound of the above (1) wherein Y is CH,

(11) a compound of the above (1) wherein Za is a group of the formula:

wherein respective symbols have the same meanings as defined above,

(12) a compound of the above (1) wherein $R^7$ is $C_{6-10}$ aryl which may be substituted,

(13) a compound of the above (1) wherein $R^{10}$ is a hydrogen atom,

(14) a compound of the above (1) wherein Zb is a bond,

(15) a compound of the above (1) wherein m is 1,

(16) a compound of the above (1) wherein $R^1$ and $R^2$ each is a hydrogen atom;

$R^3$, $R^4$, $R^5$, and $R^6$ each is a $C_{1-6}$ alkyl;

Ar is a phenyl which may be substituted by 1 to 3 substituents selected from the group consisting of halogen, $C_{1-6}$ alkyl and $C_{1-6}$ alkoxy;

ring A is a 6-membered nitrogen-containing heterocyclic ring;

X is methylene;

Y is CH or N;

Za is a group of the formula:

wherein $R^{7'}$ is a phenyl which may be substituted by 1 to 3 substituents selected from the group consisting of halogen, $C_{1-6}$ alkyl and $C_{1-6}$ alkoxy; and $R^{10'}$ is a hydrogen atom;

Zb is a bond or a $C_{1-6}$ alkylene which may be substituted by a $C_{6-10}$ aryl; and m is 1 or 2,

(17) a compound of the above (1) wherein $R^1$ and $R^2$ each is a hydrogen atom;

$R^3$, $R^4$, $R^5$, and $R^6$ each is a $C_{1-6}$ alkyl;

Ar is a $C_{6-10}$ aryl which may substituted by a methylenedioxy;

ring A is a 6-membered nitrogen-containing heterocyclic ring;

X is methylene;

Y is CH or N;

Za is a group of the formula:

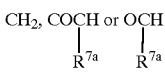

wherein $R^{7a}$ is a hydrogen atom or $C_{6-10}$ aryl;

Zb is a bond or a (i) $C_{1-6}$ alkylene or (ii) $C_{2-6}$ alkenylene group which may be substituted by a $C_{6-10}$ aryl; and m is 1,

(18) a compound of the above (1) wherein $R^1$ and $R^2$ each is hydrogen;

$R^3$, $R^4$, $R^5$, and $R^6$ each is a $C_{1-6}$ alkyl;

Ar is a $C_{6-10}$ aryl which may be substituted by 1 to 3 substituents selected from the group consisting of halogen, methylenedioxy, $C_{1-6}$ alkyl and $C_{1-6}$ alkoxy;

ring A is a 6-membered nitrogen-containing heterocyclic ring;

X is methylene;

Y is CH or N;

Za is a group of the formula:

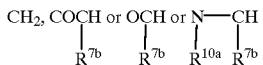

wherein $R^{7b}$ is a hydrogen atom or a $C_{6-10}$ aryl which may be substituted by a halogen; and $R^{10a}$ is a hydrogen atom or a $C_{7-11}$ aralkyl;

Zb is a bond or a divalent group selected from the group consisting of (i) a $C_{1-6}$ alkylene, (ii) a $C_{2-6}$ alkenylene and (iii) a group of the formula: —$(CH_2)_{p'}$—M'—$(CH_2)_{q'}$— wherein p' and q' each is an integer of 0 to 5, p'+q' is an integer of 1 to 6 and M' is O or NH, each of which divalent group may be substituted by a $C_{6-10}$ aryl; and m is 1 or 2,

(19) a compound of the above (1) which is

1-[(5-amino-2,3-dihydro-2,4,6,7-tetramethylbenzofuran-2-yl)methyl]-N-(diphenylmethyl)-4-piperidinamine, (−)-1-[(5-amino-2,3-dihydro-2,4,6,7-tetramethylbenzofuran-2-yl)methyl]-N-(diphenylmethyl)-4-piperidinamine, (−)-1-[(5-amino-2,3-dihydro-2,4,6,7-tetramethylbenzofuran-2-yl)methyl]-N-(diphenylmethyl)-4-piperidinamine, (1-[(5-amino-2,3-dihydro-7-isopropyl-2,4,6-trimethylbenzofuran-2-yl)methyl]-N-(diphenylmethyl-4-piperidinamine, (−)-1-[(5-amino-2,3-dihydro-7-isopropyl-2,4,6-trimethylbenzofuran-2-yl)methyl]-N-(diphenylmethyl)-4-piperidinamine, (+)-1-[(5-amino-2,3-dihydro-7-isopropyl-2,4,6-trimethylbenzofuran-2-yl)methyl]-N-(diphenylmethyl)-4-piperidinamine, or a salt thereof,

(20) a process for producing a compound of the above (1) which comprises (i) reacting a compound of the formula:

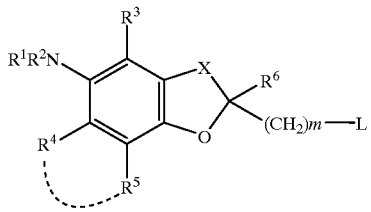

wherein L represents a leaving group; the other symbols have the same meanings as defined above, or a salt thereof with a compound of the formula:

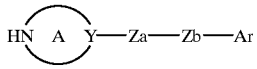

wherein the respective symbols have the same meanings as defined above, or a salt thereof;

(ii) subjecting a compound of the formula:

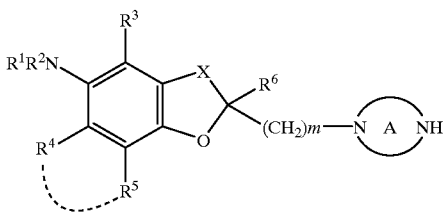

wherein the respective symbols have the same meanings as defined above, or a salt thereof to (a) alkylation, (b) acylation or (c) acylation followed by reduction;

(iii) reacting a compound of the formula:

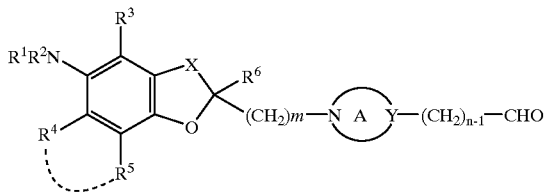

wherein n represents an integer of 1 to 4; the other symbols have the same meanings as defined above, or a salt thereof with a compound of the formula:

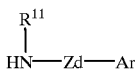

wherein $R^{11}$ represents a hydrogen atom or a hydrocarbon group which may be substituted; Zd represents a divalent aliphatic hydrocarbon group which may be substituted and may contain oxygen, nitrogen or sulfur; Ar as the same meaning as defined above, or a salt thereof, (iv) reacting a compound of the formula:

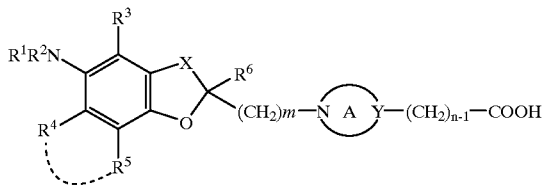

wherein the respective symbols have the same meanings as defined above, or a salt thereof with a compound of the formula:

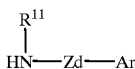

wherein the respective symbols have the same meanings as defined above, or a salt thereof, optionally followed by reduction; or (v) subjecting a compound of the formula:

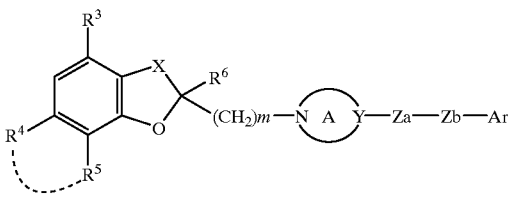

wherein the respective symbols have the same meanings as defined above, or a salt thereof to (a) nitration followed by reduction or (b) diazo coupling reaction followed by reduction,

(21) a pharmaceutical composition which comprises a compound of the above (1), if necessary together with a pharmaceutically acceptable carrier,

(22) a composition of the above (21) which is for modulating sodium channel,

(23) a composition of the above (22) which is for the prophylaxis or treatment of central nervous system ischemia, central nervous system trauma, neurodegenerative disease or cerebral edema,

(24) a method for modulating sodium channel in a mammal in need thereof which comprises administering to such mammal an effective amount of a compound of the above (1) or a pharmaceutically acceptable salt thereof with a pharmaceutically acceptable excipient, carrier or diluent,

(25) use of a compound of the above (1) or a salt thereof for manufacturing a pharmaceutical composition for modulating sodium channel,

(26) a pharmaceutical composition for modulating sodium channel which comprises compound (Ia), and

(27) a composition of the above (26) which comprises
(S)-2,3-dihydro-2,4,6,7-tetramethyl-2-[(4-phenyl-1-piperidinyl)methyl]-5-benzofuranamine,
2,3-dihydro-7-isopropyl-2,4,6-trimethyl-2-[(4-phenyl-1-piperidinyl)methyl]-5-benzofuranamine,
(−)-2,3-dihydro-7-isopropyl-2,4,6-trimethyl-2-[(4-phenyl-1-piperidinyl)methyl]-5-benzofuranamine,
(+)-2,3-dihydro-7-isopropyl-2,4,6-trimethyl-2-[(4-phenyl-1-piperidinyl)methyl]-5-benzofuranamine,
7-tert-butyl-2,3-dihydro-2,4,6-trimethyl-2-[(4-phenyl-1-piperidinyl)methyl]-5-benzofuranamine,
(−)-7-tert-butyl-2,3-dihydro-2,4,6-trimethyl-2-[(4-phenyl-1-piperidinyl)methyl]-5-benzofuranamine,
(+)-7-tert-butyl-2,3-dihydro-2,4,6-trimethyl-2-[(4-phenyl-1-piperidinyl)methyl]-5-benzofuranamine, or a salt thereof.

Referring to the above formulas, the "lower alkyl" of the "lower alkyl which may be substituted" or $R^1$, $R^2$, $R^3$, $R^4$ or $R^5$ includes, for example, $C_{1-6}$ alkyl such as methyl, ethyl, propyl, isopropyl, butyl, isobutyl, sec-butyl, tert-butyl-pentyl, and hexyl.

The "substituent" by which the "lower alkyl" may be substituted includes, for example, halogen (e.g. fluorine, chlorine, bromine, iodine, etc.), cycloalkyl (e.g. $C_{3-6}$ cycloalkyl such as cyclopropyl, cyclobutyl, cyclopentyl, cyclohexyl, etc.), lower alkynyl (e.g. $C_{2-6}$ alkynyl such as ethynyl, 1-propynyl, propargyl, etc.), lower alkenyl (e.g. $C_{2-6}$ alkenyl such as vinyl, allyl, isopropenyl, butenyl, isobutenyl, etc.), aryl (e.g. $C_{6-10}$ aryl such as phenyl, naphthyl, etc.), aralkyl (e.g. $C_{7-11}$ aralkyl such as benzyl, α-methylbenzyl, phenethyl, etc.), lower alkoxy (e.g. $C_{1-6}$ alkoxy such as methoxy, ethoxy, propoxy, isopropoxy, butoxy, isobutoxy, sec-butoxy, tert-butoxy, etc.), aryloxy (e.g. $C_{6-10}$ aryloxy such as phenoxy etc.), lower alkanoyl (e.g. $C_{1-6}$ alkyl-carbonyl such as acetyl, propionyl, butyryl, isobutyryl, etc.), arylcarbonyl (e.g. $C_{6-10}$ aryl-carbonyl such as benzoyl, naphthoyl, etc.), lower alkanoyloxy (e.g. $C_{1-6}$ alkyl-carbonyloxy such as acetyloxy, propionyloxy, butyryloxy, isobutyryloxy, etc.), arylcarbonyloxy (e.g. $C_{6-10}$ aryl-carbonyloxy such as benzoyloxy, naphthoyloxy, etc.), carboxy, lower alkoxycarbonyl (e.g. $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl, etc.), carbamoyl, amidino, imino, amino, mono-lower alkylamino (e.g. mono-$C_{1-6}$ alkylamino such as methylamino, ethylamino, propylamino, isopropylamino, butylamino, etc.), di-lower alkylamino (e.g. di-$C_{1-6}$ alkylamino such as dimethylamino, diethylamino, methylethylamino, dipropylamino, diisopropylamino, dibutylamino, etc.), 3- to 6-membered cyclic amino optionally containing 1–3 hetero atoms selected from among oxygen, sulfur and nitrogen in addition to carbon and one nitrogen atom (e.g. 3 to 6-membered cyclic amino such as aziridinyl, azetidinyl, pyrrolidinyl, pyrrolinyl, pyrrolyl, imidazolyl, pyrazolyl, imidazolidinyl, piperidino, morpholino, thiomorpholino, dihydropyridyl, pyridyl, N-methylpiperazinyl, N-ethylpiperazinyl, etc.), alkylenedioxy (e.g. $C_{1-3}$ alkylenedioxy such as methylenedioxy, ethylenedioxy, etc.), hydroxy, nitro, cyano, mercapto, sulfo, sulfino, phosphono, sulfamoyl, monoalkyl-sulfamoyl (e.g. mono-$C_{1-6}$ alkylsulfamoyl such as methylsulfamoyl, ethylsulfamoyl, propylsulfamoyl, isopropylsulfamoyl, butylsulfamoyl, etc.), dialkylsulfamoyl, (e.g. di-$C_{1-6}$ alkylsulfamoyl such as dimethylsulfamoyl, diethylsulfamoyl, dipropylsulfamoyl, dibutylsulfamoyl, etc.), lower alkylthio (e.g. $C_{1-6}$ alkylthio such as methylthio, ethylthio, propylthio, isopropylthio, butylthio, sec-butylthio, tert-butylthio, etc.), arylthio, (e.g. $C_{6-10}$ arylthio such as phenylthio, naphthylthio, etc.), lower alkylsulfinyl (e.g. $C_{1-6}$ alkylsulfinyl such as methylsulfinyl, ethylsulfinyl, propylsulfinyl, butylsulfinyl, etc.), arylsulfinyl (e.g. $C_{6-10}$ arylsulfinyl such as phenylsulfinyl, naphthylsulfinyl, etc.), lower alkylsulfonyl (e.g. $C_{1-6}$ alkylsulfonyl such as methylsulfonyl, ethylsulfonyl, propylsulfonyl, butylsulfonyl, etc.), and arylsulfonyl (e.g. $C_{6-10}$ arylsulfonyl such as phenylsulfonyl, naphthylsulfonyl, etc.).

The "lower alkyl" of the "lower alkyl which may be substituted" may have any of the above-mentioned substituents in 1 to 5, preferably 1 to 3, substitutable positions and when the number of substitutions is not less than 2, the substituents may be the same or different.

The "acyl" for $R^1$ or $R^2$ includes, for example, acyl derived from carboxylic acid or sulfonic acids. The preferred acyl includes formyl, lower alkylcarbonyl (e.g. $C_{1-6}$ alkyl-carbonyl such as acetyl, propionyl, butyryl, isobutyryl, etc.), arylcarbonyl (e.g. $C_{6-10}$ aryl-carbonyl such as benzoyl, naphthoyl, etc.), aralkylcarbonyl (e.g. $C_{6-10}$ aryl-$C_{1-6}$ alkyl-carbonyl such as benzylcarbonyl, phenethylcarbonyl, naphthylmethylcarbonyl, etc.), lower alkoxycarbonyl (e.g. $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl, etc.), aralkyloxycarbonyl (e.g. $C_{6-10}$ aryl-$C_{1-6}$ alkoxy-carbonyl such as benzyloxycarbonyl, etc.), lower alkylsulfonyl (e.g. $C_{1-6}$ alkylsulfonyl such as mesyl, ethylsulfonyl, propylsulfonyl, etc.), $C_{6-10}$ arylsulfonyl optionally having $C_{1-6}$ alkyl (e.g. phenylsulfonyl, naphthylsulfonyl, tosyl, etc.), and aralkylsulfonyl (e.g. $C_{6-10}$ aryl-$C_{1-6}$ alkylsulfonyl such as benzylsulfonyl, phenethylsulfonyl, naphthylmethylsulfonyl, etc.).

Preferably, $R^1$ and $R^2$ each is a hydrogen atom, $C_{1-6}$ alkyl or $C_{1-6}$ alkyl-carbonyl. More preferred is hydrogen atom or $C_{1-6}$ alkyl. Particularly preferred is a hydrogen atom.

The "lower alkoxy" of the "lower alkoxy which may be substituted" for $R^3$, $R^4$ or $R^5$ includes, for example, $C_{1-6}$ alkoxy such as methoxy, ethoxy, propoxy, isopropoxy, butoxy, isobutoxy, pentyloxy, and hexyloxy. The "substituent" by which the "lower alkoxy" may be substituted includes the same substituents as mentioned above for the "lower alkyl" and the number of substituents may also be similar to that mentioned for the "lower alkyl".

The "5- or 6-membered carbocyclic group" that may be formed by $R^4$ and $R^5$ taken together with the respective adjacent carbon atoms includes, for example, 6-membered aromatic hydrocarbon rings (e.g. benzene ring, etc.) and 5- or 6-membered cycloalkenes (e.g. cyclpentene, cyclopentadiene, cyclohexene, etc.).

Preferably, $R^3$, $R^4$, and $R^5$ each is $C_{1-6}$ alkyl. More preferably, $R^3$ and $R^4$ each is methyl.

The "lower alkyl" for $R^6$ may be similar to the "lower alkyl" of the "lower alkyl which may be substituted" as mentioned for $R^1$, $R^2$, $R^3$, $R^4$ or $R^5$.

Preferably, $R^6$ is $C_{1-6}$ alkyl. More preferred is methyl.

The "aromatic group" of the "aromatic group which may be substituted" for Ar includes, for example, aromatic hydrocarbon groups and aromatic heterocyclic groups.

The "aromatic hydrocarbon group" includes, for example, $C_{6-14}$ monocyclic or fused polycyclic aromatic hydrocarbon groups. Thus, for example, $C_6$-aryl such as phenyl, 1-naphthyl, 2-naphthyl, anthryl, etc. can be mentioned. Preferred are $C_{6-10}$ aryl such as phenyl, 1-naphthyl, 2-naphthyl, etc. Particularly preferred is phenyl.

The "aromatic heterocyclic group" mentioned above includes, for example, 5- to 10-membered monocyclic or its fused heteroaromatic groups containing one or more, for example 1 to 4, heteroatoms, selected from among nitrogen, sulfur and oxygen in addition to carbon. Specifically, it includes monovalent groups available upon elimination of any one hydrogen atom respectively from aromatic heterocyclic rings or fused ring systems consisting of any such heterocyclic ring (preferably a 5- or 6-membered monocyclic ring) and one or more (preferably 1 or 2, more preferably 1) aromatic rings (e.g. benzene ring or pyridine ring, etc.), such as thiophene, benzothiophene, benzofuran, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, isoquinoline, quinoline, carbazole, isothiazole, isoxazole, etc. The preferred "aromatic heterocyclic group" includes 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzothienyl, benzofuranyl, 2-thienyl, 3-thienyl, 2-benzoxazolyl, 2-benzimidazolyl, and 2-pyridothiazolyl. Particularly preferred are 2-pyridyl, 3-pyridyl, 4-pyridyl, 2-quinolyl, 3-quinolyl, 4-quinolyl, 2-indolyl, and 3-indolyl.

The "substituent" of "aromatic group which may be substituted" for Ar includes, for example, halogen (e.g. fluorine, chlorine, bromine, iodine, etc.), $C_{1-3}$ alkylenedioxy (e.g. methylenedioxy, ethylenedioxy, etc.), nitro, cyano, $C_{1-6}$ alkyl which may be halogenated, $C_{3-6}$ cycloalkyl (e.g. cyclopropyl, cyclobutyl, cyclopentyl, cyclohexyl, etc.), $C_{1-6}$ alkoxy which may be halogenated, $C_{1-6}$ alkylthio which may be halogenated, hydroxy, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, methylethylamino, dipropylamino, dibutylamino, etc.), $C_{1-6}$ alkyl-carbonyl (e.g. acetyl, propionyl, etc.), carboxy, $C_{1-6}$ alkoxy-propoxycarbonyl, butoxycarbonyl, etc.), carbamoyl, mono-$C_{1-6}$ alkyl-carbamoyl (e.g. methylcarbamoyl, ethylcarbamoyl, etc.), di-$C_{1-6}$ alkyl-carbamoyl (e.g. dimethylcarbamoyl, diethylcarbamoyl, etc.) $C_{6-10}$ aryl-carbamoyl (e.g. phenylcarbamoyl, naphthylcarbamoyl, etc.), sulfo, $C_{1-6}$ alkylsulfonyl (e.g. methylsulfonyl, ethylsulfonyl, etc.), $C_{6-10}$ aryl (e.g. phenyl, naphthyl, etc.), and $C_{6-10}$ aryloxy (e.g. phenyloxy, naphthyloxy, etc.). When the substitutent is $C_{1-13}$ alkylenedioxy, it preferably forms a ring with the adjacent two carbon atoms.

The "$C_{1-6}$ alkyl which may be halogenated" includes, for example, $C_{1-6}$ alkyl (e.g. methyl, ethyl, propyl, isopropyl, butyl, isobutyl, sec-butyl, tert-butyl, pentyl, hexyl, etc.) optionally having 1 to 3 halogen atoms (e.g. fluorine, chlorine, bromine, iodine, etc.). Thus, for example, methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc. may be mentioned.

The "$C_{1-6}$ alkoxy which may be halogenated" includes, for example, $C_{1-6}$ alkoxy optionally having 1 to 3 halogen atoms (e.g. fluorine, chlorine, bromine, iodine, etc.). Thus, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc. can be mentioned.

The "$C_{1-6}$ alkylthio which may be halogenated" includes, for example, $C_{1-6}$ alkylthio (e.g. methylthio, ethylthio, propylthio, isopropylthio, butylthio, sec-butylthio, tert-butylthio, etc.) optionally having 1 to 3 halogen atoms (e.g. fluorine, chlorine, bromine, iodine, etc.). Thus, for example, methylthio, difluoromethylthio, trifluoromethylthio, ethylthio, propylthio, isopropylthio, butylthio, 4,4,4-trifluorobutylthio, pentylthio, hexylthio, etc. can be mentioned.

The "aromatic group" of the "aromatic group which may be substituted" may have 1 to 5, preferably 1 to 3, substituents in substitutable nuclear positions and the specific substituents that may be present include those mentioned above. When two or more substitutions are involved, the substituents may be similar or dissimilar.

Preferably, Ar is a $C_{6-14}$ aryl (preferably phenyl), 2-pyridyl, 3-pyridyl, 4-pyridyl, 2-indolyl or 3-indolyl group which may be substituted. More preferably, Ar is a $C_{6-10}$ aryl which may be substituted. The preferred "substituent" in this instance includes halogen, $C_{1-6}$ alkoxy and $C_{1-6}$ alkyl. More preferably, Ar is $C_{6-14}$ aryl (preferably phenyl) which may be substituted by 1 to 3 substituents selected from among halogen, $C_{1-6}$ alkoxy and $C_{1-6}$ alkyl.

The "5- to 8-membered nitrogen-containing heterocyclic ring" of the "5- to 8-membered nitrogen-containing heterocyclic ring which may be substituted" for ring A includes, for example, 5- to 8-membered saturated or unsaturated heterocyclic rings, each of which contains at least one nitrogen atom in addition to carbon. The specific list of such heterocyclic rings includes peperidine, piperazine, 1,2,5,6-tetrahydropyridine, pyrrolidine, 1 H-azepine, 1H-2,3-dihydroazepine, 1H-2,3,4,5-tetrahydroazepine, 1 H-2,3,6,7-tetrahydroazepine, 1H-2,3,4,5,6,7-hexahydroazepine, 1H-1,4-diazepine, 1H-2,3-dihydro-1,4-diazepine, 1H-2,3,4,5-tetrahydro-1,4-diazepine, 1H-2,3,6,7-tetrahydro-1,4-diazepine, 1H-2,3,4,5,6,7-hexahydro-1,4-diazephine, 1,2-dihydroazocine, 2,3,4,5 -tetrahydroazocine, 1,2,3,4,5,6-hexahydroazocine, 1,2,3,4,5,6,7,8-octahydroazocine, 1,2-dihydro-1,5-diazocine, 1,2,3,4,5,6-hexahydro-1,5-diazocine, 1,2,3,4,5,6,7,8-octahydro-1,5-diazocine, etc. Preferred is 6-membered nitrogen-containing heterocyclic ring. More preferred are piperidine and piperazine.

The "substituent" which may optionally be present on the "5- to 8-membered nitrogen-containing heterocyclic ring" includes the same groups as those mentioned above for the "aromatic group which may be substituted" as mentioned for Ar. The number of substituents may range from 1 to 3 and when two or more substituents are involved, the substituents may be similar or dissimilar.

Preferably, ring A is a 6membered nitrogen-containing heterocyclic ring which may be substituted. More preferably, ring A is piperidine or piperazine.

The "lower alkylene" of the "lower alkylene which may be substituted" for X includes, for example, divalent groups available upon elimination of two hydrogen atoms respectively from $C_{1-6}$ alkanes. The "lower alkylene" includes, for example, straight-chain $C_{1-6}$ alkylene such as methylene, ethylene, trimethylene, tetramethylene, pentamethylene, butylene, pentylene, etc. Preferred are methylene and ethylene. Particularly preferred is methylene.

The "substituent" optionally present on the "lower alkylene which may be substituted" as mentioned above includes, for example, halogen (e.g. fluorine, chlorine, bromine, iodine, etc.), $C_{1-6}$ alkyl (e.g. methyl, ethyl, propyl, isopropyl, butyl, isobutyl, pentyl, hexyl, etc.), $C_{3-6}$ cycloalkyl (e.g. cyclopropyl, cyclobutyl, cyclopentyl, etc.), $C_{2-6}$ alkenyl (e.g. vinyl, allyl, 1-propenyl, 2-butenyl, etc.), $C_{1-6}$ alkynyl (e.g. ethynyl, 2-propynyl, 2-butynyl, etc.), $C_{6-14}$ aryl (e.g. phenyl, 1-naphthyl, 2-naphthyl, biphenylyl, etc.), nitro, cyano, hydroxy, $C_{1-6}$ alkoxy (e.g. methoxy, ethoxy, propoxy, isopropoxy, butoxy, isobutoxy, pentyloxy, hexyloxy, etc.), amino, mono-$C_{1-6}$ alkylamino (e.g. methylamino, ethylamino, etc.), di-$C_{1-6}$ alkylamino (e.g. dimethylamino, diethylamino, methylethylamino, etc.), $C_{6-10}$ aryloxy (e.g. phenyloxy, naphthyloxy, etc.), and oxo.

The "lower alkylene" of the "lower alkylene which may be substituted" may have 1 to 3, preferably 1 to 2, such substituents in substitutable positions of the lower alkylene and when two or more substituents are involved, the substituents may be similar or dissimilar.

The preferred example of X is methylene.

When Y represents carbon, a group of the formula:

may by typically mentioned.

In the above formula, $R^8$ is, for example, a hydrogen atom, halogen (e.g. fluorine, chlorine, bromine, iodine, etc.), nitro, cyano, $C_{1-6}$ alkyl which may be halogenated, $C_{3-6}$ cycloalkyl (e.g. cyclopropyl, cyclobutyl, cyclopentyl, cyclohexyl, etc.), $C_{1-6}$ alkoxy which may be halogenated, $C_{1-6}$ alkylthio which may be halogenated, hydroxy, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, methylethylamino, dipropylamino, dibutylamino, etc.), $C_{1-6}$ alkyl-carbonyl (e.g. acetyl, propionyl, etc.), carboxy, $C_{1-6}$ alkoxy-carbonyl (e.g. methoxycarbonyl, ethoxycarbonyl, propoxycarbonyl, butoxycarbonyl, etc.), carbamoyl, mono-$C_{1-6}$ alkyl-carbamoyl (e.g. methylcarbamoyl, ethylcarbamoyl, etc.), di-$C_{1-6}$ alkyl-carbamoyl (e.g. dimethylcarbamoyl, diethylcarbamoyl, etc.), $C_{6-10}$ aryl-carbamoyl (e.g. phenylcarbamoyl, naphthylcarbamoyl, etc.), sulfo, $C_{1-6}$ alkylsulfonyl (e.g. methylsulfonyl, ethylsulfonyl, etc.), $C_{6-10}$ aryl (e.g. phenyl, naphthyl, etc.), and $C_{6-10}$ aryloxy (e.g. phenyloxy, naphthyloxy, etc.). Preferably, $R^8$ is hydrogen, cyano, $C_{1-6}$ alkyl (e.g. methyl, ethyl, propyl, isopropyl, butyl, isobutyl, pentyl, hexyl, etc.), $C_{1-6}$ alkoxy (e.g. methoxy, ethoxy, propoxy, isopropoxy, butoxy, isobutoxy, pentyloxy, hexyloxy, etc.), hydroxy, amino, mono-$C_{1-6}$ alkylamino, di-$C_{1-6}$ alkylamino or $C_{1-6}$ alkylcarbonyl.

When Y represents nitrogen, Za is preferably a group of the formula:

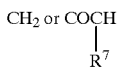

wherein $R^7$ is as defined above.

Preferably, Y is CH or N. More preferably, Y is CH.

The "aromatic group which may be substituted" for $R^7$ includes groups similar to those mentioned for the "aromatic group which may be substituted" as mentioned for Ar.

Preferably, $R^7$ is hydrogen or a $C_{6-10}$ aryl which may be substituted. More preferred is a $C_{6-10}$ aryl (e.g. phenyl, 1-naphthyl, 2-naphthyl, etc; preferably phenyl) which may be substituted by a halogen.

The "hydrocarbon group" of the "hydrocarbon group which may be substituted" for $R^{10}$ is a group available upon elimination of one hydrogen atom from a hydrocarbon compound, thus including both acyclic and cyclic hydrocarbon groups (e.g. alkyl, alkenyl, alkynyl, cycloalkyl, aryl, aralkyl, etc.). Preferred is the following acyclic or cyclic $C_{1-16}$ hydrocarbon group.

(i) $C_{1-6}$ alkyl (e.g. methyl, ethyl, propyl, isopropyl, butyl, isobutyl, sec-butyl, tert-butyl, pentyl, hexyl, etc.), (ii) $C_{2-6}$ alkenyl (e.g. vinyl, allyl, isopropenyl, butenyl, isobutenyl, sec-butenyl, etc.), (iii) $C_{2-6}$ alkynyl (e.g. ethynyl, propargyl, butynyl, 1-hexynyl, etc.), (iv) $C_{3-6}$ cycloalkyl (e.g. cyclopropyl, cyclobutyl, cyclopentyl, cyclohexyl, etc.), (v) $C_{6-14}$ aryl (e.g. phenyl, 1-naphthyl, 2-naphthyl, biphenyl, 2-anthryl, etc.; preferably phenyl), (vi) $C_{7-16}$ aralkyl (e.g. benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, etc.; preferably benzyl).

The "substituent" optionally present on the "hydrocarbon group which may be substituted" includes 1 to 5, preferably 1 to 3 substituents similar to the "substituent" of the "lower alkyl which may be substituted" as mentioned for $R^1$, $R^2$, $R^3$, $R^4$ or $R^5$.

The "acyl" for $R^{10}$ is the same as the "acyl" mentioned for $R^1$ or $R^2$.

Preferably, $R^{10}$ is hydrogen or $C_{7-11}$ aralkyl. Particularly preferred is hydrogen.

Za is preferably a group of the formula:

wherein the respective symbols have the same meanings as defined above. More preferred is a group of the formula:

wherein $R^7$ has the same meaning as defined above.

The "divalent aliphatic hydrocarbon group which may may contain oxygen, nitrogen or sulfur" of the "divalent aliphatic hydrocarbon group which may be substituted and may contain oxygen, nitrogen or sulfur" as mentioned for Zb includes, for example, (i) methylene or (ii) a divalent group available upon elimination of one hydrogen atom from each of the two carbon atoms of a saturated or unsaturated aliphatic hydrocarbon and optionally having 1 or 2, preferably 1, hetero atom selected from among oxygen, nitrogen and sulfur between carbon atoms or at the terminal position (s). Preferred is group having 1 to 8 carbon atoms. Examples of the group include (i) $C_{1-8}$ alkylene (e.g. —$CH_2$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, etc.), (ii) $C_{2-8}$ alkenylene (e.g. —CH=CH—, —$CH_2$—CH=CH—, —$CH_2$—CH=CH—$CH_2$—, —$CH_2$—$CH_2$—CH=CH—, —CH=CH—$CH_2$—$CH_2$—$CH_2$—, —$CH_2$—$CH_2$—$CH_2$—$CH_2$—CH=CH—, etc.), (iii) $C_{2-8}$ alkynylene (e.g. —C≡C—, —$CH_2$—C≡C—, —$CH_2$—C≡C—$CH_2$—$CH_2$—, etc.), (iv) group of the formula: —$(CH_2)_p$—M-$(CH_2)_q$— wherein M represents O, $NR^9$, S, SO or $SO_2$; p and q each represents an integer of 0 to 8 and p+q represents an integer of 1 to 8. In the above formula $R^9$ represents a hydrogen atom, $C_{1-6}$ alkyl (e.g. methyl, ethyl, propyl, isopropyl, butyl, isobutyl, pentyl, hexyl, etc.), $C_{3-6}$ cycloalkyl (e.g. cyclopropyl, cyclobutyl, cyclopentyl, etc.), $C_{6-14}$ aryl (e.g. phenyl, 1-naphthyl, 2-naphthyl, biphenylyl, etc.), $C_{7-11}$ aralkyl (e.g. benzyl, phenethyl, etc.) or acyl, The "acyl" mentioned just above includes the same groups as mentioned for the "acyl" represented by $R^1$ or $R^2$.

M is preferably O or $NR^9$, where $R^9$ is preferably hydrogen.

Each of p and q is preferably an integer of 0 to 5, more preferably an integer of 0 to 4.

The "substituent" optionally present on the "divalent aliphatic hydrocarbon group which may contain oxygen, nitrogen or sulfur" includes, for example, halogen (e.g. fluorine, chlorine, bromine, iodine, etc.), nitro, cyano, $C_{1-6}$ alkyl which may be halogenated, $C_{3-6}$ cycloalkyl (e.g. cyclopropyl, cyclobutyl, cyclopentyl, cyclohexyl, etc.), $C_{1-6}$ alkoxy which may be halogenated, $C_{1-6}$ alkylthio which may be halogenated, hydroxy, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, methylethylamino, dipropylamino, dibutylamino, etc.), $C_{6-14}$ aryl (e.g. phenyl, 1-naphthyl, 2-naphthyl, biphenylyl, etc.), $C_{7-11}$ aralkyl (e.g. benzyl, phenethyl, etc.), $C_{6-10}$ aryloxy (e.g. phenyloxy, naphthyloxy, etc.), oxo, and acyl. The above-mentioned "$C_{1-6}$ alkyl which may be halogenated", "$C_{1-6}$ alkoxy which may be halogenated" and "$C_{1-6}$ alkylthio which may be halogenated" may be those mentioned hereinbefore as substituents on the aromatic group for Ar. The "acyl" mentioned just above includes the same groups as mentioned for the "acyl" represented by $R^1$ or $R^2$.

Those substituents may be present in 1 to 5 substitutable positions and where the number of substituents is 2 or more, the substituents may be similar or dissimilar.

Zb is preferably a bond or a $C_{1-8}$ alkylene. More preferably, Zb is a bond.

The "aromatic group which may be substituted" for Q may be the same as the "aromatic group which may be substituted" as mentioned for Ar.

The "divalent aliphatic hydrocarbon group which may be substituted and may contain oxygen, nitrogen or sulfur" for Zc may be similar to the "divalent aliphatic hydrocarbon group which may be substituted and may contain oxygen, nitrogen or sulfur" as mentioned for Zb.

Q is preferably an aromatic group which may be substituted.

The "5- to 8-membered nitrogen-containing heterocyclic ring which may be substituted" of the "5- to 8-membered nitrogen-containing heterocyclic ring which may be substituted or corresponding fused benzologue system" for ring Aa may be the same as the "5- to 8-membered nitrogen-containing heterocyclic ring which may be substituted" for ring A. The "fused benzologue system corresponding to the 5- to 8-membered nitrogen-containing heterocyclic ring which may be susbtituted" may be the fused ring system available upon condensation of the "5- to 8-membered nitrogen-containing heterocyclic ring which may be substituted" for ring A with "a benzene ring which may be substituted" on a condensable plane. The "substituent optionally present on the "benzene ring which may be substituted" may be similar to the substituent optionally present on the "aromatic group which may be substituted" for Ar. The number of the substituents may range from 1 to 4.

Preferably, ring Aa is a 6-membered nitrogen-containing heterocyclic ring. More preferably, ring Aa is a piperidine.

In compound (I), the preferred is a compound wherein $R^1$ and $R^2$ each is a hydrogen atom;

$R^3$, $R^4$, $R^5$, and $R^6$ each is $C_{1-6}$ alkyl;

Ar is a phenyl which may be substituted by 1 to 3 substituents selected from the group consisting of halogen, $C_{1-6}$ alkyl and $C_{1-6}$ alkoxy;

ring A is a 6-membered nitrogen-containing heterocyclic ring;

x is methylene;

Y is CH or N;

Za is a group of the formula:

wherein $R^{7'}$ is a phenyl which may be substituted by 1 to 3 substituents selected from the group consisting of halogen, $C_{1-6}$ alkyl and $C_{1-6}$ alkoxy; and $R^{10'}$ is a hydrogen atom;

Zb is a bond or a $C_{1-6}$ alkylene which may be substituted by a $C_{6-10}$ aryl; and m is 1 or 2.

Preferred are compounds, inclusive of salts thereof, of formula (I) wherein $R^1$ and $R^2$ each is a hydrogen atom;

$R^3$, $R^4$, $R^5$ and $R^6$ each is a $C_{1-6}$ alkyl;

Ar is a (i) $C_{6-10}$ aryl, (ii) 2-pyridyl, (iii) 3-pyridyl, (iv) 4-pyridyl, (v) 2-indolyl or (vi) 3-indolyl, each of which may be substituted by 1 to 3 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy;

ring A is a 6-membered nitrogen-containing heterocyclic ring;

X is methylene;

Y is CH or N;

Za is a group of the formula:

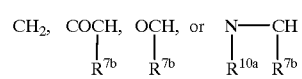

$R^{7b}$ is a hydrogen atom or a $C_{6-10}$ aryl which may be substituted by a halogen;

$R^{10a}$ is a hydrogen atom or a $C_{7-11}$ aralkyl;

$Z^b$ is a bond or a (i) $C_{1-6}$ alkylene, (ii) $C_{2-6}$ alkenylene or (iii) group of the formula: $—(CH_2)_{p'}—M'—(CH_2)_{q'}—$ wherein p' and q' each represents an integer of 0 to 5 and p'+q' represents an integer of 1 to 6; M' represents O or NH, each of which may be substituted by a $C_{6-10}$ aryl; and m is 1 or 2.

Particularly preferred are compounds wherein $R^{10a}$ is a hydrogen atom, Zb is a bond, and m is 1, and salts thereof.

Also preferred are compounds of formula (I), inclusive of salts thereof, wherein $R^1$ and $R^2$ each is a hydrogen atom;

$R^3$, $R^4$, $R^5$ and $R^6$ each is a $C_{1-6}$ alkyl;

Ar is a $C_{6-10}$ aryl which may be substituted by a methylenedioxy;

ring A is a 6-membered nitrogen-containing heterocyclic ring;

X is methylene;

Y is CH or N;

Za is a group of the formula;

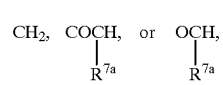

$R^{7a}$ is a hydrogen atom or a $C_{6-10}$ aryl;

Zb is (i) a bond or (ii) a $C_{1-6}$ alkylene or $C_{2-6}$ alkenylene group which may be substituted by a $C_{6-10}$ aryl; and m is 1.

Also preferred are compounds of formula (I), inclusive of their salts, wherein $R^1$ and $R^2$ each is a hydrogen atom;

$R^3$, $R^4$, $R^5$ and $R^6$ each is a $C_{1-6}$ alkyl;

Ar is a $C_{6-10}$ aryl which may be substituted by 1 to 3 substituents selected from the group consisting of halogen, methylenedioxy, $C_{1-6}$ alkyl and $C_{1-6}$ alkoxy;

ring A is a 6-membered nitrogen-containing heterocyclic ring;

X is methylene;

Y is CH or N;

Za is a group of the formula;

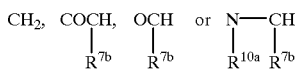

$R^{7b}$ is a hydrogen atom or a $C_{6-10}$ aryl which may be substituted by a halogen;

$R^{10a}$ is a hydrogen atom or a $C_{7-11}$ aralkyl;

Zb is a bond or a (i) $C_{1-6}$ alkylene, (ii) $C_{2-6}$ alkenylene or (iii) group of the formula: —$(CH_2)_{p'}$-M'-$(CH_2)_{q'}$— wherein p' and q' each represents an integer of 0 to 5 and p'+q' represents an integer of 1 to 6; M' represents O or NH, each of which may be substituted by a $C_{6-10}$ aryl; and m is 1 or 2.

The preferred species of compound (I) of the present invention includes,

2-[(4-benzyl-1-piperidinyl)methyl]-2,3-dihydro-2,4,6,7-tetramethyl-5-benzofuranamine, 1-[(5-amino-2,3-dihydro-2,4,6,7-tetramethylbenzofuran-2-yl)methyl]-N-(diphenylmethyl)-4-piperidinamine, (−)-1-[(5-amino-2,3-dihydro-2,4,6,7-tetramethylbenzofuran-2-yl)methyl]-N-(diphenylmethyl)-4-piperidinamine, (+)-1-[(5-amino-2,3-dihydro-2,4,6,7-tetramethylbenzofuran-2-yl)methyl]-N-(diphenylmethyl)-4-piperidinamine, 1-[(5-amino-2,3-dihydro-7-isopropyl-2,4,6-trimethylbenzofuran-2-yl)methyl]-N-(diphenylmethyl)-4-piperidinamine, (−)-1-[(5-amino-2,3-dihydro-7-isopropyl-2,4,6-trimethylbenzofuran-2-yl)methyl]-N-(diphenylmethyl)-4-piperidinamine, (+)-1-[(5-amino-2,3-dihydro-7-isopropyl-2,4,6-trimethylbenzofuran-2-yl)methyl]-N-(diphenylmethyl)-4-piperidinamine, 2-[[4-diphenylmethoxy)-1-piperidinyl]methyl]-2,3-dihydro-2,4,6,7-tetramethyl-5-benzofuranamine, 1-[(5-amino-2,3-dihydro-2,4,6,7-tetramethylbenzofuran-2-yl)methyl]-N-(3,3-diphenylpropyl)-4-piperidineethylamine, 2,3-dihydro-2,4,6,7-tetramethyl-2-[[4-(2-phenylethyl)-1-piperazinyl]methyl]-5-benzofuranamine, and salts thereof.

More preferred is

1-[(5-amino-2,3-dihydro-2,4,6,7-tetramethylbenzofuran-2-yl)methyl]-N-(diphenylmethyl)-4-piperidinamine, (−)-1-[(5-amino-2,3-dihydro-2,4,6,7-tetramethylbenzofuran-2-yl)methyl]-N-(diphenylmethyl)-4-piperidinamine, (+)-1-[(5-amino-2,3-dihydro-2,4,6,7-tetramethylbenzofuran-2-yl)methyl]-N-(diphenylmethyl)-4-piperidinamine, 1-[(5-amino-2,3-dihydro-7-isopropyl-2,4,6-trimethylbenzofuran-2-yl)methyl]-N-(diphenylmethyl)-4-piperidinamine, (−)-1-[(5-amino-2,3-dihydro-7-isopropyl-2,4,6-trimethylbenzofuran-2-yl)methyl]-N-(diphenylmethyl)-4-piperidinamine, (+)-1-[(5-amino-2,3-dihydro-7-isopropyl-2,4,6-trimethylbenzofuran-2-yl)methyl]-N-(diphenylmethyl)-4-piperidinamine, or a salt thereof.

Preferred compounds of formula (Ia), inclusive of salts thereof, are compounds wherein $R^1$ and $R^2$ each is a hydrogen atom, a $C_{1-6}$ alkyl or $C_{1-6}$ alkyl-carbonyl;

$R^3$, $R^4$, $R^5$ and $R^6$ each is a $C_{1-6}$ alkyl;

ring Aa is a 6- or 7-membered nitrogen-containing heterocyclic ring which may be fused to a benzene ring;

X is methylene;

Y is (i) a group of the formula

(wherein $R^{8a}$ represents a hydrogen atom or hydroxy) or (ii) N;

Q is (i) a hydrogen atom, (ii) a $C_{6-10}$ aryl or 6-membered nitrogen-containing aromatic group which may be substituted by halogen or $C_{1-6}$ alkoxy, or (iii) a group of the formula

(wherein Zc' represents a $C_{1-6}$ alkylene or $C_{2-6}$ alkenylene group which may be substituted by $C_{6-10}$ aryl or oxo and may contain oxygen; and Ar' represents a $C_{6-10}$ aryl); and m is 1.

The preferred species of compound (Ia) includes (S)-2,3-dihydro-2,4,6,7-tetramethyl-2-[(4-phenyl-1-piperidinyl)methyl]-5-benzofuranamine, 2,3-dihydro-7-isopropyl-2,4,6-trimethyl-2-[(4-phenyl-1-piperidinyl)methyl]-5-benzofuranamine, (−)-2,3-dihydro-7-isopropyl-2,4,6-trimethyl-2-[(4-phenyl-1-piperidinyl)methyl]-5-benzofuranamine, (+)-2,3-dihydro-7-isopropyl-2,4,6-trimethyl-2-[(4-phenyl-1-piperidinyl)methyl]-5-benzofuranamine, 7-tert-butyl-2,3-dihydro-2,4,6-trimethyl-2-[(4-phenyl-1-piperidinyl)methyl]-5-benzofuranamine, (−)-7-tert-butyl-2,3-dihydro-2,4,6-trimethyl-2-[(4-phenyl-1-piperidinyl)methyl]-5-benzofuranamine, (+)-7-tert-butyl-2,3-dihydro-2,4,6-trimethyl-2-[(4-phenyl-1-piperidinyl)methyl]-5-benzofuranamine, or a salt thereof.

More preferred is (S)-2,3-dihydro-2,4,6,7-tetramethyl-2-[(4-phenyl-1-piperidinyl)methyl]-5-benzofuranamine and its salt.

While compound (I) and compound (Ia) include stereoisomers, the respective isomers and mixtures thereof also fall within the scope of the present invention.

The salt of compound (I) of the present invention or compound (Ia) is typically a pharmacologically acceptable salt such as salts with inorganic bases, ammonium salts, salts with organic bases, salts with inorganic acids, salts with organic acids, and salts with basic or acidic amino acids. The preferred salts with inorganic bases are salts with alkali metals such as sodium, potassium, etc., salts with alkaline earth metals such as calcium, magnesium, etc., aluminum salt, etc. The preferred salts with organic bases are salts with trimethylamine, triethylamine, pyridine, picoline, 2,6-lutidine, ethanolamine, diethanolamine, triethanolamine, cyclohexylamine, dicyclohexylamine, and N,N'-dibenzylethylenediamine, among others. The preferred salts with inorganic acids are salts with hydrochloric acid, hydrobromic acid, nitric acid, sulfuric acid, phosphoric acid, etc. The preferred salts with organic acids are salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. The preferred salts with basic amino acids are salts with arginine, lysine, ornithine, etc. The preferred salts with acidic amino acids are salts with aspartic acid, glutamic acid, etc.

Particularly preferred salts are pharmacologically acceptable salts. When compound (I) or (Ia) contains a basic functional group, the preferred salt includes the corresponding represented by the reaction schemes presented hereinafter. Compound (Ia) can be produced by the per se known methods (e.g. the processes disclosed in EP-A-483772, JP-A-5-140142 and JP-A-6-41123, U.S. Pat. No. 5,552,552, etc.), or analogous thereto, or the processes represented by the reaction schemes presented below.

In the following reaction schemes, the respective symbols have the same meanings as defined hereinbefore. The compounds (II) through (XXVIII) in the reaction schemes include their salts which may be of the same kinds as those mentioned for compound (I).

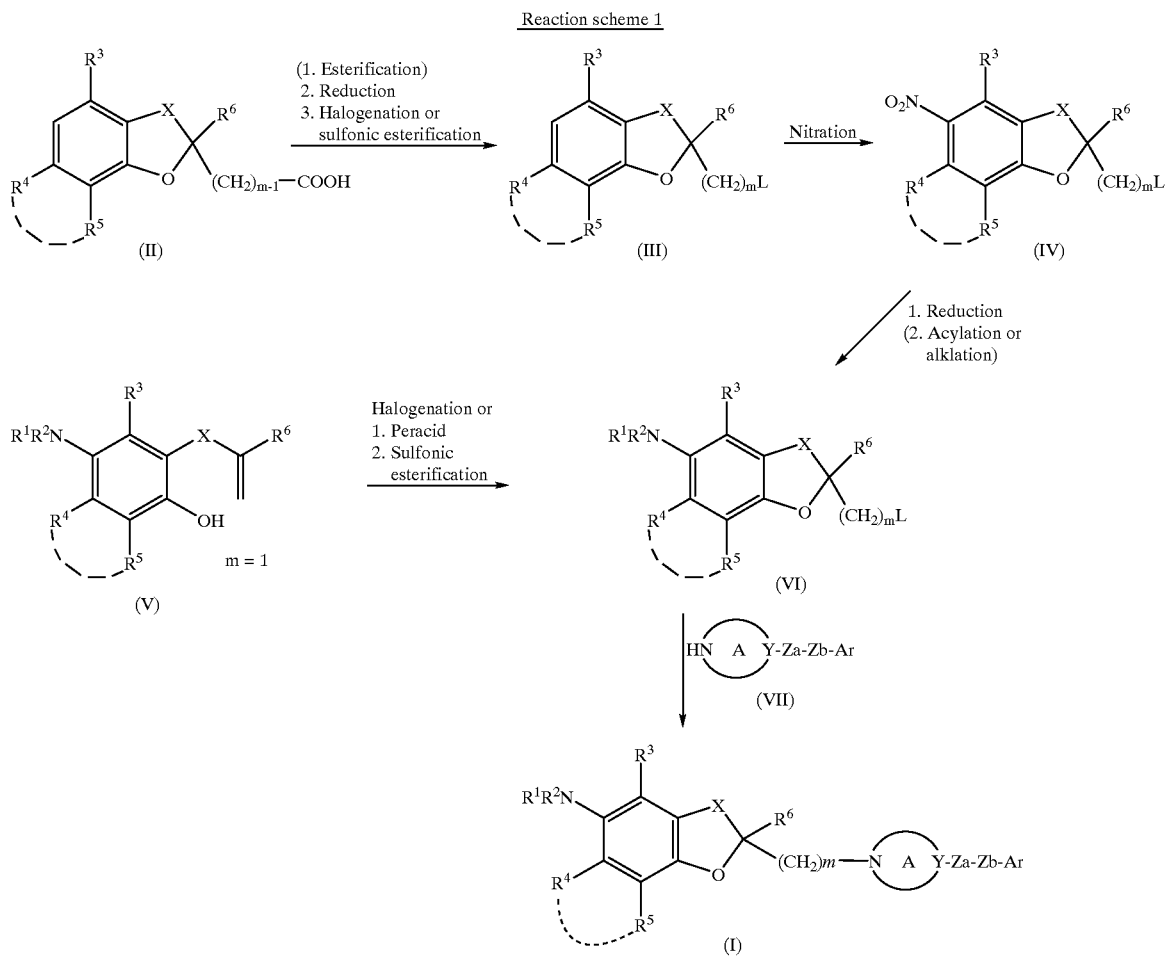

ing salts with inorganic acids such as hydrochloric acid, hydrobromic acid, nitric acid, sulfuric acid, phosphoric acid, etc. and salts with organic acids such as acetic acid, phthalic acid, fumaric acid, oxalic acid, tartaric acid, maleic acid, citric acid, succinic acid, methanesulfonic acid, p-toluenesulfonic acid, etc. When an acidic functional group is present, the preferred salt includes the corresponding salts with alkali metals such as sodium, potassium, etc., salts with alkaline earth metals such as calcium, magnesium, etc., and ammonium salts.

The process for producing compound (I) of the present invention is not described.

Compound (I) of the invention can be produced by the per se known methods or analogous thereto, or the processes Compound (II) can be obtained by the per se known method, for example any of the processes disclosed in JP-A-62-87585, JP-A-5-140142, J. Am. Oil Chem. Soc., 51, 200–203, 1974, etc., or any process analogous thereto.

Compound (V) can be obtained by the per se known method, for example the process disclosed in JP-A-5-140142, or any process analogous thereto.

Compound (VII) may be purchased from a commercial source if it is available on the market to be obtained by the per se known method, for example the processes disclosed in Eur. J. Med. Chem. 15, 363–370, 1980, JP-A-2-49726, etc., or any process analogous thereto.

Compound (III) (wherein L represents a leaving group) can be obtained by a process which comprises reducing the carboxyl group of compound (II) either directly or after esterification to give the corresponding alcohol and subjecting it to sulfonic esterification or halogenation.

The "leaving group" for L includes, for example, halogen (e.g. fluorine, chlorine, bromine, iodine, etc.), $C_{1-5}$ alkylsulfonyloxy which may be halogenated (e.g. methanesulfonyloxy, ethanesulfonyloxy, trichloromethanesulfonyloxy, etc.), and arylsulfonyloxy (e.g. benzenesulfonyloxy which may be substituted, typically p-toluenesulfonyloxy and benzenesulfonyloxy, etc.).

The reducing agent for use in the reduction of carboxyl includes, for example, metal hydrides such as aluminum hydride, diisobutylaluminum hydride, etc., metal hydrogen complexes such as lithium aluminum hydride, sodium borohydride, etc., borane complexes such as borane tetrahydrofuran complex, borane dimethyl sulfide complex, etc., alkylboranes such has thexylborane, disiamylborane, etc., and diborane. The proportion of the reducing agent, taking a metal hydride as an example, is about 0.5 to 10 mols, preferably about 0.5 to 3.0 mols, per mol of compound (II), and in the case of a metal hydrogen complex, about 0.5 to 10 mols, preferably about 0.5 to 5.0 mols, per mol of compound (II). The proportion of a borane complex, an alkylborane or diborane is about 1.0 to 10.0 mols, preferably 1.0 to 5.0 mols, per mol of compound (II). This reaction can be carried out advantageously in the presence of an inert solvent. There is otherwise no particular limitation on the kind of solvent only if it does not interfere with progress of the reaction. It is preferable to use alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., organic acids such as formic acid, acetic acid, etc., and mixtures of such solvents. The reaction time is generally 1–100 hours, preferably about 1–50 hours. The reaction temperature is generally 0–120° C., preferably 20–80° C. After completion of the reaction, the reaction mixture can be submitted to the next reaction either as it is or after partial purification but the product compound can be easily isolated by per se known method and purified by the routine procedure such a recrystallization, distillation, chromatography, etc.

The reducing agent for use in the process comprising esterifying compound (II) by the routine method of organic chemistry and reducing the resultant ester includes, for example, metal hydrides such as aluminum hydride, diisobutylaluminum hydride, etc., metal hydrogen complexes such as lithium aluminum hydride, sodium borohydride, etc., borane complexes such as borane tetrahydrofuran complex, borane dimethyl sulfide complex, etc., alkylboranes such as thexylborane, disiamylborane, etc., diborane, and hydrogenation catalysts such as Raney nickel, Raney cobalt, and so on. The proportion of the reducing agent, taking a metal hydride as an example, is about 1.0 to 10 mols, preferably about 1.0 to 3.0 mols, per mol of the ester of compound (II) and, in the case of a metal hydrogen complex, about 1.0 to 10 mols, preferably about 1.0 to 3.0 mols, per mole of the ester of compound (II). In the case of a borane complex, an alkylborane or diborane, the proportion per mol of the ester of compound (II) is about 1.0 to 5.0 mols. In the case of hydrogenation, a hydrogenation catalyst is used in a proportion of about 10 to 1000 weight %, preferably about 80 to 300 weight %, based on the weight of the ester of compound (II). This reaction is carried out with advantage in the presence of an inert solvent. There is otherwise no particular limitation on the solvent that can be used only if it does not interfere with the reaction. Examples of the solvent include alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., organic acids such as formic acid, acetic acid, etc., and mixtures of such solvents. Depending on the activity and amount of the catalyst used, the reaction time is generally 1–100 hours, preferably 1–50 hours. The reaction temperature is generally 0–120° C., preferably 20–80° C. When a hydrogenation catalyst is employed, the hydrogen pressure is set to generally 1–100 atmospheres. After completion of the reaction, the reaction mixture can be submitted to the next reaction either as it is or after partial purification but the product compound can be easily isolated by per se known method and purified by the routine purification procedure such as recrystallization, distillation, chromatography, etc.

For conversion of the thus-obtained alcohol to the sulfonic acid ester, a sulfonating agent such as methanesulfonyl chloride or p-toluenesulfonyl chloride is employed, optionally in combination with a base if necessary. The sulfonating agent is used in a proportion of about 1.0 to 5.0 mols, preferably about 1.0 to 2.0 mols, per mol of the alcohol. This reaction is preferably conducted in an inert solvent. There is no particular limitation on the kind of solvent that can be used but ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichlorethane, etc., nitriles such as acetonitrile, propionitrile, etc., sulfoxides such as dimethyl sulfoxide etc., nitrogen-containing aromatic hydrocarbon compounds such as pyridine, lutidine, quinoline, etc., and mixtures of such solvents can be used with advantage. The base that can be optionally used includes, for example, triethylamine and pyridine. The reaction temperature is about –20–150° C., preferably 0–100° C. The reaction time is generally 5 minutes to 24 hours, preferably 10 minutes to 5 hours.

The halogenating agent includes, for example, thionyl halides such as thionyl chloride, thionyl bromide, etc., phosphoryl halides such as phosphoryl chloride, phosphoryl bromide, etc., phosphorus halides such as phosphorus pentachloride, phosphorus trichloride, phosphorus pentabromide, phosphorus tribromide, etc., oxalyl halides such as oxalyl chloride etc., and phosgene. The halogenating agent is used in a proportion of about 1.0 to 30 mols, preferably about 1.0 to 10 mols, per mol of the alcohol. This reaction is preferably carried out in the absence of a solvent or in an inert solvent. The kind of solvent is not so critical but aromatic hydrocarbons such as benzene, toluene, etc., saturated hydrocarbons such as cyclohexane, hexane, etc., ethers such as tetrahydrofuran, dioxane, 1,2-dimethoxyethane, etc., amides such as N,N-dimethylformamide, N,N-dimethylacetamide, etc., halogenated hydrocarbons such as dichloromethane, chloroform, carbon tetrachloride, 1,2-dichloroethane, etc., and mixtures of such solvents can be used with advantage. The reaction time is generally 10 minutes to 12 hours, preferably 10 minutes to 5 hours. The reaction temperature is generally –10–200° C., preferably –10–120° C. Thus obtained compound (III) can be submitted to the next reaction either as the reaction mixture or after partial purification, but can be easily isolated by per se known method and purified by the routine purification procedure such as recrystallization, distillation, chromatography, etc.

Compound (IV) can be produced by nitrating compound (III). The nitrating agent that can be used includes, for example, mixed acid, acetyl nitrate, fuming nitric acid, nitronium tetrafluoroborate ($NO_2^+BF_4^-$), and nitronium trifluoromethanesulfonate ($NO_2^+CF_3SO_3^-$). The nitrating agent is used in a proportion of about 1.0 to 50 mols, preferably about 1.0 to 10 mols, per mol of compound (III). This reaction can be advantageously conducted in the absence of a solvent or in an inert solvent. The kind of solvent used is not so critical but organic acids such as acetic acid, acid anhydrides such as acetic anhydride, mineral acids such as sulfuric acid, nitric acid, etc., saturated hydrocarbons such as cyclohexane, hexane, etc., halogenated hydrocarbons such as dichloromethane, chloroform, carbon tetrachloride, 1,2-dichloroethane, etc., and mixtures of such solvents are preferred. The reaction time is generally 10 minutes to 12 hours, preferably 10 minutes to 5 hours. The reaction temperature is generally −10–200° C. and preferably −10–120° C. Thus obtained compound (IV) can be submitted to the next reaction either as the reaction mixture or after partial purification but may be easily isolated by per se known method and purified by the routine purification procedure such as recrystallization, distillation, chromatography, etc.

Compound (VI) can be produced by reducing compound (IV) and optionally subjecting it to alkylation and/or acylation. The reducing agent that can be used for this reduction includes, for example, metal hydrides such as aluminum hydride, diisobutylaluminum hydride, etc., metal hydrogen complexes such as lithium aluminum hydride, sodium borohydride, etc., borane complexes such as borane tetrahydrofuran complex, borane dimethyl sulfide complex, etc., alkylboranes such as thexylborane, disiamylborane, etc., diborane, certain metals such as sinc, aluminum, tin, iron, etc., and alkali metal (e.g. sodium, lithium, etc.)/liquid ammonia (Birch reduction). Aside from those reducing agents, various catalysts such as palladium on carbon, platinum oxide, Raney nickel, Raney cobalt, etc. can be used as hydrogenation catalysts. The proportion of the reducing agent, taking a metal hydride as an example, is about 1.0 to 10 mols, preferably about 1.0 to 3.0 mols, per mol of compound (IV) and, in the case of a metal hydrogen complex, is about 1.0 to 10 mols, preferably about 1.0 to 3.0 mols, per mol of compound (IV). In the case of a borane complex, an alkylborane or diborane, the proportion per mol of compound (IV) is about 1.0 to 5.0 mols. In the case of a metal, it is used in a proportion of about 1.0 to 20 equivalents, preferably about 1 to 5 equivalents. In the case of an alkali metal, its proportion is about 1 to 20 equivalents, preferably about 1 to 5 equivalents. In the case of hydrogenation, the catalyst such as palladium on carbon, platinum oxide, Raney nickel and Raney cobalt, is used in a proportion of about 5 to 1000 weight %, preferably about 10 to 300 weight %, based on the weight of compound (IV). This reaction can be advantageously carried out in an inert solvent. The kind of solvent is not so critical only if it does not interfere with the reaction. Preferred are alcohols such as methanol, ethanol, propanol, etc., ethers such as diethyl ether, tetrahydrofuran, dioxane, 1,2-dimethoxyethane, etc., hydrocardbons such as benzene, toluene, cyclohexane, etc., amides such as N,N-dimethylformamide, N,N-dimethylacetamide, etc., organic acids such as formic acid, acetic acid, etc., and mixtures of such solvents. When Raney nickel or Raney cobalt is used, an amine such as ammonia may be added for suppression of side reactions. Depending on the kind and amount of the catalyst used, the reaction time is generally 1–100 hours, preferably 1–50 hours. The reaction temperature is generally 0–120° C., preferably 20–80° C. When a hydrogenation catalyst is used, the hydrogen pressure is generally 1 to 100 atmospheres. After completion of the reaction, the reaction mixture can be submitted to the next reaction either as it is or after partial purification, but the product compound can be easily isolated by per se known method and purified by the routine purification procedure such as recrystallization, distillation, chromatography, etc.

The resultant amine is alkylated where necessary.

Thus, compound (VI) (wherein at least one of $R^1$ and $R^2$ represents a hydrogen atom) is reacted with the corresponding alkylating agent (e.g. the corresponding alkyl halide or corresponding alkyl sulfonate, etc.), optionally in the presence of a base. Relative to each mol of compound (VI), the alkylating agent is used in a proportion of about 1.0 to 5.0 mols, preferably about 1.0 to 2.0 mols. The base that can be used includes, for example, inorganic bases such as sodium carbonate, potassium carbonate, cesium carbonate, sodium hydrogen carbonate, etc., aromatic amines such as pyridine, lutidine, etc., tertiary amines such as triethylamine, tripropylamine, tributylamine, cyclohexldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., and metal alkoxides such as sodium methoxide, sodium ethoxide, potassium tert-butoxide, etc. The base is used in a proportion of about 1.0 to 5.0 mols, preferably about 1.0 to 2.0 mols, per mol of compound (VI). This reaction is advantageously carried out in an inert solvent. There is no particular limitation on the kind of solvent. Preferred are alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitriles such as acetonitrile, propionitrile, etc., sulfoxides such as dimethyl sulfoxide etc., and mixtures of such solvents. The reaction time is generally 30 minutes to 48 hours, preferably 1–24 hours. The reaction temperature is generally −20–200° C., and preferably 0–150° C.

The amine obtained is acylated as necessary.

Thus, compound (VI) (wherein at least one of $R^1$ and $R^2$ represents a hydrogen atom) is reacted with an acylating agent, optionally in the presence of a base or an acid. The acylating agent may for example be the corresponding carboxylic acid or a reactive derivative thereof (e.g. acid halide, acid anhydride, ester, etc.). The acylating agent is used in a proportion of about 1.0 to 5.0 mols, preferably about 1.0 to 2.0 mols, per mol of compound (VI). This reaction can be advantageously carried out in the absence of a solvent or an intert solvent. There is no particular limitation on the kind of solvent that can be used. Preferred are ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitriles such as acentonitrile, propionitrile, etc., sulfoxides such as dimethyl sulfoxide etc., nitrogen-containing aromatic hydrocarbon compounds such as pyridine, lutidine, quinoline, etc., and mixtures of such solvents. The base that can be used optionally includes, for example, triethylamine and pyridine. The acid that can be used optionally includes, for example, methaneulfonic acid, p-toluenesulfonic acid, and camphorsulfonic acid. The reaction temperature is about −20–150° C., preferably 0–100° C. the reaction time is generally 5 minutes to 24 hours, preferably 10 minutes to 5 hours. Thus obtained compound (VI) can be submitted to the next reaction either as the reaction mixture or after partial purification, but can be easily isolated by per se known method and purified by the routine purification procedure such as recrystallization, distillation, chromatography, etc.

If desired, the above alkylation and acylation reactions can be carried out in combination or repeatedly.

Compound (VI) can also be produced by treating compound (V) with a halogenation reagent. This reaction can be conducted with bases, basic salts or radical initiator or under light exposure, where necessary. The halogenation reagent includes, for example, halogen such as bromine, chlorine, or iodine, imide such as N-bromosuccinimide, halogen adduct such as benzyltrimethylammonium dichloroiodate, benzyltrimethylammonium tribromide, tetramethylammonium bromide bromine adduct, pyridinium bromide perbromide, dioxane dibromide. The halogenation reagent is used in a proportion of about 1.0 to 5.0 mols, preferably about 1.0 to 2.0 mols, per mol of compound (V). This reaction is preferably carried out in the absence of a solvent or in an inert solvent. There is no particular limitation on the kind of solvent unless progress of the reaction is not interfered with. Preferred are ethers such as diethyl ether, tetrahydrofuran, dioxane, 1,2-dimethoxyethane, etc., alcohols such as methanol, ethanol, propanol, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitriles such as acetonitrile, propionitrile, etc., sulfoxides such as dimethyl sulfoxide etc., organic acids such as acetic acid, propionic acid, etc., nitroalkanes such as nitromethane, etc., aromatic amines such as pyridine, lutidine, quinoline, etc., and mixtures of such solvents. the base that can be optionally used includes, for example, inorganic bases such as sodium carbonate, potassium carbonate, cesium carbonate, sodium hydrogen carbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The basic salt that can be optionally used includes, for example, sodium acetate, potassium acetate, etc. the radical initiator that can be optionally used includes, for example, benzoyl peroxide, azobisisobutyronitrile, etc. In the case of the light exposure, halogen lamp can be used. The reaction temperature is about −50–150° C., preferably 0–100° C. The reaction time is generally 5 minutes to 24 hours, preferably 10 minutes to 5 hours.

Compound (VI) can also be produced by a process which comprises cyclizing compound (V) with an organic peracid optionally in the presence of a base and subjecting the resultant alcohol to sulfonic esterification. The organic peracid that can be used includes, for example, m-chloroperbenzoic acid and peracetic acid. The organic peracid is used in a proportion of about 1.0 to 5.0 mols, preferably about 1.0 to 2.0 mols, per mol of compound (V). This reaction is preferably carried out in an inert solvent. There is no particular limitation on the kind of solvent that can be used unless the reaction is hindered. Preferred are water, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitriles such as acetonitrile, propionitrile, etc., sulfoxides such as dimethyl sulfoxide etc., organic acids such as acetic acid, propionic acid, etc., nitrogen-containing aromatic hydrocarbon compounds such as pyridine, lutidine, quinoline, etc., and mixtures of such solvents. The base that can be optionally employed includes, for example, inorganic bases such as sodium carbonate, potassium carbonate, cesium carbonate, sodium hydrogen carbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The reaction temperature is about −20–150° C., preferably 0–100° C. The reaction time is generally 5 minutes to 24 hours and preferably 10 minutes to 5 hours. The next sulfonic esterification reaction can be carried out under the same conditions as described for the production of compound (III) from compound (II). Thus obtained compound (VI) can be submitted to the next reaction either as the reaction mixture or after partial purification, but can be easily isolated by per se known method and purified by the routine purification procedures such as recrystallization, distillation, chromatography, etc.

Compound (I) can be produced by subjecting compound (VI) to condensation with compound (VII).

This condensation of compound (VI) with compound (VII) can be carried out optionally in the presence of a base. The base includes, for example, inorganic bases such as sodium carbonate, potassium carbonate, cesium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., alkali metal hydrides such as sodium hydride, potassium hydride, etc., metal amides such as sodium amide, lithium diisopropylamide, lithium hexamethyldisilazide, etc., and metal alkoxides such as sodium methoxide, sodium ethoxide, potassium tert-butoxide, etc. The base is used in a proportion of about 1.0 to 30 mols, preferably about 1.0 to 10 mols, per mol of compound (VI). This reaction is advantageously carried out in the absence of a solvent or in an inert solvent. There is no particular limitation on the kind of solvent that can be used unless the reaction is interefered with. Preferred are halogenated hydrocarbons such as dichloroethane, chloroform, etc., aliphatic hydrocarbons such as hexane, cyclohexane, etc., aromatic hydrocarbons such as toluene, xylene, etc., ethers such as diethyl ether, diisopropyl ether, etc., amides such as dimethylformamide, dimethylacetamide, etc., alcohols such as methanol, ethanol, etc., and mixtures of such solvents. The proportion of the solvent is generally 0.2 to 50 μL, preferably 2 to 20 mL, per gram of compound (VI). This reaction is conducted generally at −5–200° C., preferably at 5–180° C. The reaction time is generally about 5 minutes to 72 hours, preferably about 0.5 to 30 hours. When a high reaction temperature is adopted, the reaction is generally carried out in an autoclave or the like.

Reaction scheme 2

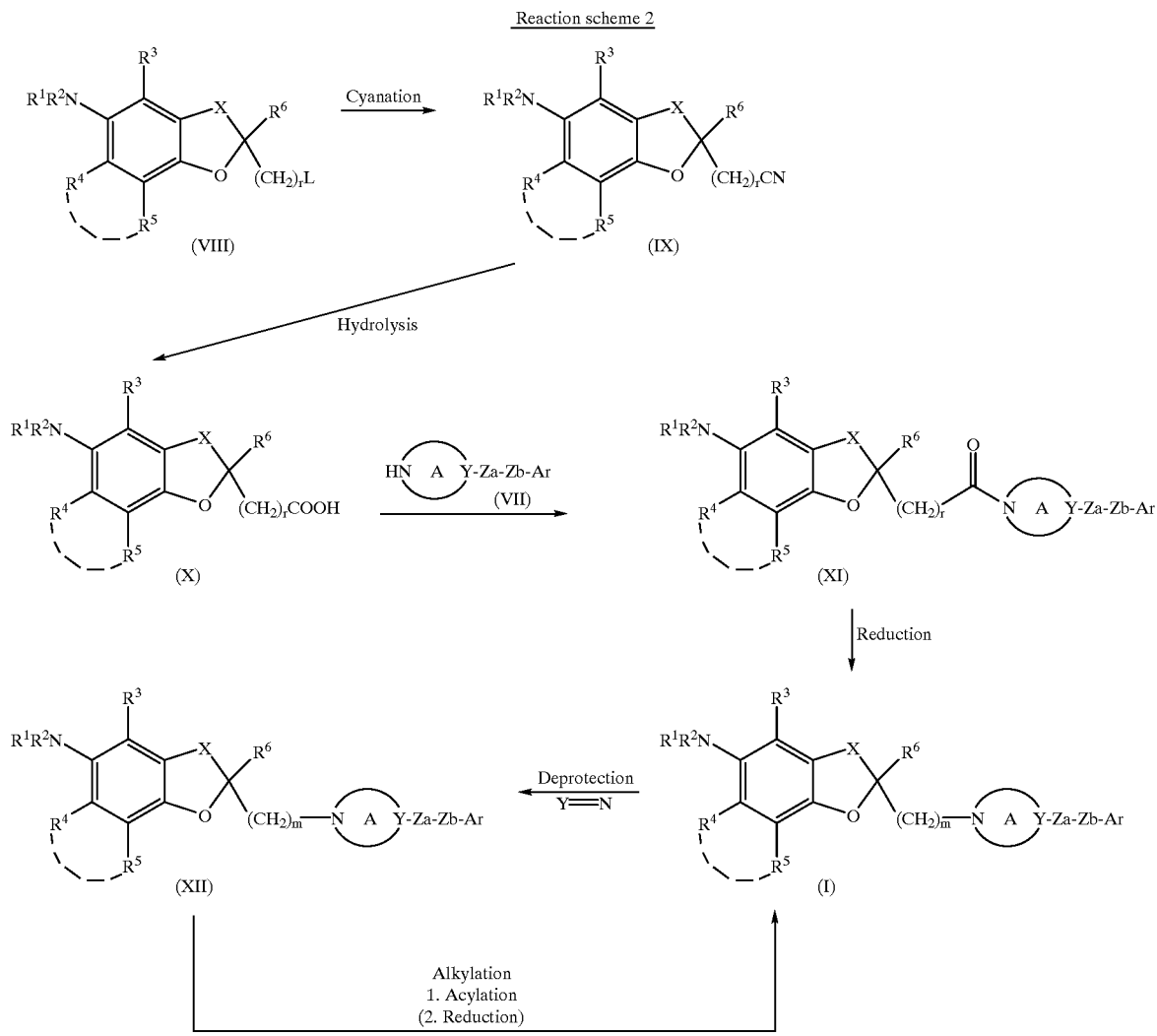

Referring to compound (IX) (wherein L has the same meaning as defined above; r represents 1 or 2), compound (IX) wherein r=1 can be obtained by reacting compound (VI) wherein m=1, that is to say compound (VIII) (wherein r has the same meaning as above) wherein r=1, with a cyano compound. The cyano compound includes, for example, sodium cyanide, potassium cyanide, and a mixture thereof. It is also possible to use a cyano compound prepared by in situ reaction of hydrogen cyanide with an alkali metal salt such as sodium hydroxide, potassium hydroxide, sodium carbonate, potassium carbonate or the like. The cyano compound is used in a proportion of about 0.8 to 10 mols, preferably about 1.0 to 5.0 mols, per mol of compound (VIII). This reaction can be carried out advantageously in an inert solvent. There is no particular limitation on the kind of solvent that can be used unless the reaction is interfered with. The preferred solvent includes alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, chlorobenzene, o-dichlorobenzene, etc., sulfoxides such as dimethyl sulfoxide etc., water, and mixtures of such solents. The reaction may also be carried out using water and a solvent eithe rinsoluble or sparingly soluble in water, as chosen from among the above-mentioned solvents, in the presence of a phase transfer catalyst. The phase transfer catalyst that can be employed includes, for example, quaternary ammonium salts such as tetrabutylammonium bromide, benzyltriethylammonium chloride, etc. and quaternary phosphonium salts. The phase transfer catalyst is used in a proportion of about 0.001 to 10 mols, preferably about 0.005 to 0.5 mols, per mol of compound (VIII). The reaction time is generally 10 minutes to 50 hours, preferably 30 minutes to 20 hours. The reaction temperature is generally 0–200° C. Thus obtained compound (IX) can be submitted to the next reaction either as the reaction mixture or after partial purification, but can be easily isolated by per se known method and purified by the routine procedure such as recrystallization, distillation, chromatography, etc Referring to compound (X) (wherein r has the same meaning as defined above), compound (X) wherein r=1 can be produced by hydrolyzing compound (X) wherein r=1 with an acid or a base.the acid hydrolysis can be carried out with a mineral acid such as hydrochloric acid, hydrobromic acid, sulfuric acid, etc., a Lewis acid such as boron trichloride, boron tribromide, etc., either as it is alone or in combination with a thiol or a sulfide, or an organic acid such as trifluroacetic acid, p-toluenesulfonic acid, etc. The alkaline hydrolysis can be carried out using a metal hydroxide such as sodium hydroxide, potassium hydroxide, barium hydroxide, etc., a metal carbonate such as sodium carbonate, potassium carbonate, etc., a metal alkoxide such as sodium methoxide, sodium ethoxide, potassium tert-butoxide, etc., or an organic base such as triethylamine, imidazole, formamidine, etc. The acid or base is used in a proportion of about 0.1 to 20 mols, preferably about 0.5 to 12 mols, per mol of compound (IX). This reaction can be advantageously carried out in the absence of a solvent or in an inert solvent. There is no particular limitation on the kind of solvent that can be used unless the reaction is interferred with. The preferred solvent includes, for example, alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, hexane, etc., halogenated hydrocarbons such as dichloromethane, chloroform, carbon tetrachloride, 1,2-dichloroethane, chlorobenzene, o-dichlorobenzene, etc., sulfoxides such as dimethyl sulfoxide etc., water, and mixtures of such solvents. The reaction time is generally 10 minutes to 50 hours and preferably 30 minutes to 40 hours. The reaction temperature is generally 0–200° C., preferably 20–150° C. Thus obtained compound (X) can be used either as the reaction mixture or after partial purification, but can be easily isolated by per se known method and purified by the routine procedure such as recrystallization, distillation, chromatography, etc.

Compound (VIII) wherein r=2 can be produced from compound (X) wherein r=1 in the same manner as the above-described production of compound (III) from compound (II).

Compound (IX) wherein r=2 can be produced from compound (VIII) wherein r=1 in the same manner as the above-described production of compound (IX) wherein r=1 from compound (VIII) wherein r=2.

Compound (X) wherein r=2 can be produced from compound (IX) wherein r=2 in the same manner as the above-described production of compound (X) wherein r=1 from compound (IX) wherein r=1.

Compound (XI) (wherein r has the same meaning as defined above) can be produced by condensing compound (VII) with compound (X), a reactive derivative of compound (X) or a salt of compound (X). The reactive derivative of compound (X) includes the corresponding acid halides (e.g. acid chloride, acid bromide, etc.), acid amides (e.g. the corresponding acid amides with pyrazole, imidazole, benzotriazole, etc.), mixed acid anhydrides (e.g. mixed acid anhydrides with mono-$C_{1-4}$ alkylcarbonic acids such as monomethylcarbonic acid, monethylcarbonic acid, monoisopropylcarbonic acid, mono-tert-butylcarbonic acid, etc.; mixed acid anhydrides with mono-$C_{7-10}$ aralkylcarbonic acids such as monobenzylcarbonic acid, mono(p-nitrobenzyl)carbonic acid, etc.; mixed acid anhydrides with $C_{1-6}$ aliphatic carboxylic acids such as acetic acid, cyanoacetic acid, propionic acid, butyric acid, isobutyric acid, valeric acid, isovaleric acid, pivalic acid, trifluoroacetic acid, trichloroacetic acid, acetoacetic acid, etc.; mixed acid anhydrides with $C_{7-11}$ aromatic carboxylic acids such as benzoic acid, p-toluic acid, p-chlorobenzoic acid, etc.; mixed acid anhydrides with organic sulfonic acids such as methanesulfonic acid, ethanesulfonic acid, benzenesulfonic acid, p-toluenesulfonic acid, etc.; and mixed acid anhydrides with monoallylcarbonic acid etc.), acid azides, active esters (e.g. diethoxyphosphoric acid ester, diphennoxyphosphoric acid ester, p-nitrophenyl ester, 2,4-dinitrophenyl ester, cyanomethyl ester, pentachlorophenyl ester, ester with N-hydroxysuccinimide, ester with N-hydroxyphthalimide, ester with 1-hydroxybenzoltriazole, ester with 6-chloro-1-hydroxybenzotriazole, ester with 1-hydroxy-1H-2-pyridone, etc.), and active thioesters (e.g. 2-pyridylthio ester, 2-benzothiazolylthio ester, etc.).

As an alternative to using the reactive derivative of compound (X) as above, compound (X) or a salt of compound (X) may be directly reacted with compound (VII) in the presence of a suitable condensing agent. The condensing agent that can be used includes, for example, N,N'-disubstituted carbodiimides such as N,N'-dicyclohexylcarbodiimide, 1-ethyl-3-(3-dimethylaminopropyl)carbodiimide (WSC) hydrochloride, etc., azolides such as N,N'-carbonyldiimidazole etc., dehydrating agents such as N-ethoxycarbonyl-2-ethoxy-1,2-dihydroquinoline, phosphorus oxychloride, alkoxyacetylenes, etc., and 2-halopyridinium salts such as 2-chloromethylpyridinium iodide, 2-fluoro-1-methylpyridinium iodide, etc. Compound (VII) is used in a proportion of generally about 1.0 to 5.0 mols, preferably about 1.0 to 2.0 mols, per mol of compound (X), a reactive derivative of compound (X) or a salt of compound (X). This reaction can be advantageously carried out in an inert solvent. There is no particular limitation on the kind of solvent that can be used unless the reaction is interferred with. Preferred are ethers such as diethyl ether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitriles such as acetonitrile, propionitrile, etc., sulfoxides such as dimethyl sulfoxide etc., water, and mixtures of such solvents. When the acid halide, mixed acid anhydride, or reactive ester is used as the reactive derivative of compound (X), the reaction can be carried out in the presence of an acid acceptor for removing the released acid from the reaction system. The acid acceptor that can be used for this purpose includes inorganic bases such as sodium carbonate, potassium carbonate, sodium hydrogen carbonate, etc., aromatic amines such as pyridine, lutidine, etc., and tertiary amines such as triethylamine, tripropylamine, tributylamine, cyclohexylidimethylamine, 4-dimethylaminopyridine, N,N-dimethylaniline, N-methylpiperidine, N-methylpyrrolidine, N-methylmorpholine, etc. Though it depends on the kinds of reagent and solvent used, the reaction time is generally 30 minutes to 48 hours, preferably 30 minutes to 24 hours. The reaction temperature is generally 0–100° C., preferably 0–70° C.

Thus obtained compound (XI) can be submitted to the next reaction either as the reaction mixture or after partial purification, but can be easily isolated by per se known method and purified by the routine purification procedure such as recrystallization, distillation, chromatography, etc.

Compound (I) can also be produced by reducing compound (XI). The reducing agent that can be used for this reduction includes, for example, metal hydrides such as aluminum hydride, diisobutylaluminum hydride, etc., metal hydrogen complexes such as lithium aluminum hydride, sodium borohydride, etc., borane complexes such as borane tetrahydrofuran complex, borane dimethyl sulfide complex, etc., alkylboranes such as thexylborane, disiamylborane, etc., and diborane. Relative to each mol of compound (XI), the reducing agent is used in a proportion of about 1.0 to 10 mols, preferably about 1.0 to 3.0 mols, in the case of a metal hydride, about 1.0 to 3.0 mols, preferably about 1.0 to 5.0 mols, in the case of a metal hydrogen complex, and about 1.0 to 10.0 mols, preferably 1.0 to 7.0 mols, in the case of a borane complex, an alkylborane, or diborane. This reaction can be advantageously carried out in an inert solvent. There is no particular limitation on the kind of solvent that can be used unless the reaction is interferred with. Preferred solvent are ethers such as diethyl ether, tetrahydrofuran, dioxane, 1,2-dimethoxyethane, etc., hydrocarbons such as benzene, toluene, cyclohexane, etc., and mixtures of such solvents. The reaction time is generally 15 minutes to 100 hours, preferably 20 minutes to 50 hours. The reaction temperature is generally 0–120° C., preferably 10–80° C. After comple- The alkylation can be carried out in the same manner as the above-described production of compound (I) from compound (VI).

The acylation can be carried out in the same manner as the above-described production of compound (XI) from compound (X).

The step wherein the amide obtained by the acylation is reduced can be carried out in the same manner as the above-described production of compound (I) from compound (XI).

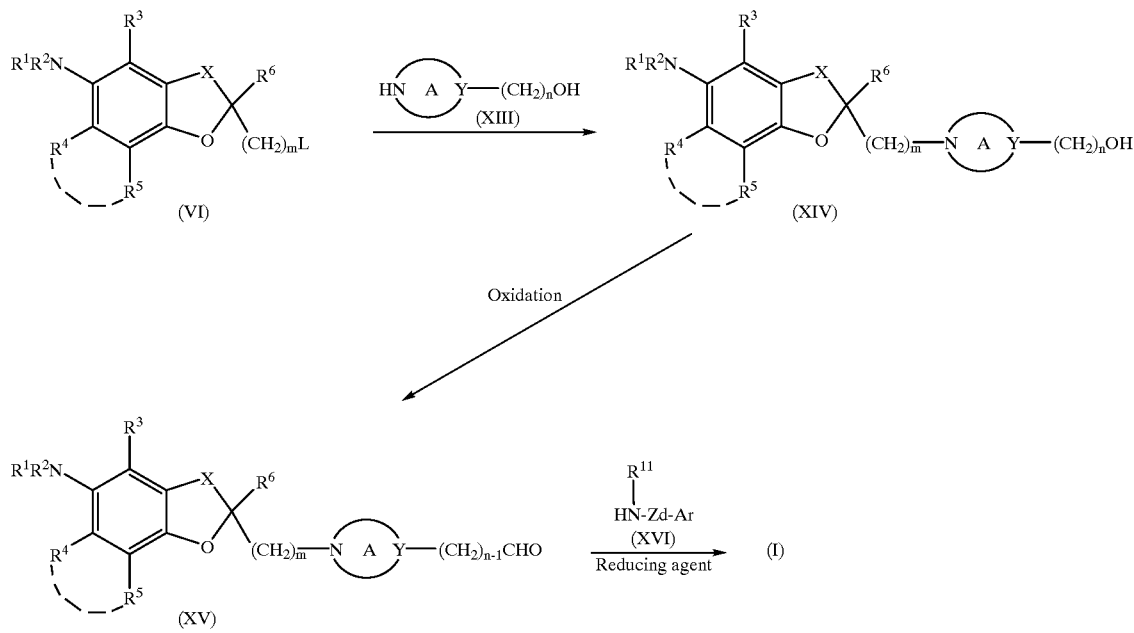

Reaction scheme 3 tion of the reaction, the reaction mixture can be submitted to the next reaction either as it is or after partial purification but the obtained compound in the reaction system can be easily isolated by per se known method and purified by the routine separatory procedure such as recrystallization, distillation, chromatography, etc.

Compound (XII) can be produced by removing a group of the formula: —Za—Zb—Ar (wherein the respective symbols have the meanings defined above) from compound (I) wherein Y=N. This deprotection can be achieved by treating the above compound (I) with a suitable reagent such as an acid, a base, ultraviolet light, hydrazine, phenylhydrazine, sodium N-methyldithiocarbamate, tetrabutylammonium fluoride and palladium acetate, or by reduction reaction. These reactions can be carried out in accordance with per se known processes, for example, the processes described in Protective Groups in Organic Synthesis, Second Edition, John Wiley & Sons, Inc., 1991. Thus obtained compound (XII) can be submitted to the next reaction either as the reaction mixture or after partial purification, but can be easily isolated by per se known method and purified by the routine purification procedure such as recrystallization, distillation, chromatography, etc.

Compound (I) wherein Y=N can be produced from compound (XII) wherein Y=N by subjecting the latter to (i) alkylation, (ii) acylation or (iii) acylation and subsequent reduction of the resultant amide.

Compound (XIV) (wherein n represents an integer of 1 to 4) can be produced by subjecting compound (VI) and compound (XIII) (wherein n has the same meaning as above) to a condensation similar to the above-described condensation of compound (VI) and compound (VII).

Compound (XIII) can be purchased and used, when it is available on a market, or be obtained by a per se known method, for example, the process described in J. Med. Chem., 34, 1073, 1991, etc.

Compound (XV) (wherein n has the same meaning as defined above) can be produced by subjecting compound (XIV) to a per se known oxidation. The oxidizing agent that can be used for this reaction includes chromic acid compounds such as chromic anhydride, sodium dischromate, potassium dichromate, etc., periodic acid compounds such as p-periodic acid, m-periodic acid, sodium m-periodate, etc., metal oxides such as manganese dioxide, silver oxide, lead oxide, etc., a combination of a sulfoxide such as dimethyl sulfoxide, with a dehydrating agent such as oxalyl chloride or N,N'-dicyclohexylcarbodiimide. The oxidizing agent is used in a proportion of about 1 to 30 mols, preferably about 1 to 10 mols, per mol of compound (XIV). There is no particular limitation on the kind of solvent that can be used only if the reaction is not interferred with. Preferred are ethers such as diethyl ether, tetrahydrofuran, dioxane, 1,2-dimethoxyethane, etc., hydrocarbons such as benzene, toluene, cyclohexane, etc., amides such as N,N- dimethylformamide, N,N-dimethylacetamide, etc., halogenated hydrocarbons such as dichloromethane, chloroform, carbon tetrachloride, 1,2-dichloroethane, etc., ketones such as acetone, methyl ethyl ketone, etc., nitriles such as acetonitrile, propionitrile, etc., sulfoxides such as dimethyl sulfoxide etc., water, and mixtures of such solvents. The reaction time is generally 5 minutes to 48 hours, preferably 5 minutes to 16 hours. The reaction temperature is generally −90–200° C., preferably −80–150° C. After completion of the reaction, the reaction mixture can be submitted to the next reaction either as it is or after partial purification but the objective compound produced in the reaction system can be easily isolated by per se known method and purified by the routine purification procedure such as recrystallization, distillation, chromatography, etc.

Compound (I) can also be produced by reductive condensation of compound (XV) and compound (XVI) (wherein $R^{11}$ represents a hydrogen atom or a hydrocarbon group which may be substituted; Zd represents a divalent aliphatic hydrocarbon group which may be substituted and may contain oxygen, nitrogen or sulfur).

The "hydrocarbon group which may be substituted" for $R^{11}$ may be similar to the "hydrocarbon group which may be substituted" for $R^{10}$ above.

The "divalent aliphatic hydrocarbon group which may be substituted and may contain oxygen, nitrogen or sulfur" for Zd may be similar to the "divalent aliphatic hydrocarbon group which may be substituted and may contain oxygen, nitrogen or sulfur" as mentioned for Zb. When the above "divalent aliphatic hydrocarbon group which may be substituted" contains oxgen or sulfur, the hetero atom exist between carbon atoms.

Compound (XVI) may be purchased and used, when it is commercially available or be obtained by per se known method.

Compound (XVI) is used in a proportion of about 0.5 to 2 mols, preferably 0.8 to 1.5 mols, per mol of compound (XV). The reducing agent that can be used includes, for example, metal hydrides such as aluminum hydride, diisobutylaluminum hydride, etc., metal hydrogen complexes such as lithium aluminum hydride, sodium borohydride, sodium cyanoborohydride, etc., borane complexes such as borane tetrahydrofuran complex, borane dimethyl sulfide complex, etc., alkylboranes such as thexylborane, disiamylborane, etc., and diborane. In conducting this reaction, an acid (e.g. hydrogen chloride, sulfuric acid, acetic acid, trifluoroacetic acid, etc.) may be optionally employed. Relative to each mol of compound (XV), the reducing agent is used in a proportion of about 0.3 to 10 mols, preferably about 0.3 to 3.0 mols, in the case of a metal hydride, about 0.3 to 10 mols, preferably about 0.5 to 5.0 mols, in the case of a metal hydrogen complex, and about 1.0 to 10.0 mols, preferably 1.0 to 3.0 mols, in the case of a borane complex, an alkylborane or diborane. This reaction can be advantageously carried out in an inert solvent. There is no particular limitation on the kind of solvent that can be used unless the reaction is interfered with but preferred solvent are alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., water, and mixtures of such solvents. The reaction time is generally 10 minutes to 10 hours, preferably 10 minutes to 2 hours. The reaction temperature is generally −20–120° C., preferably −10–80° C. After completion of the reaction, the reaction mixture can be submitted to the next reaction either as it is or after partial purification but the product compound can be easily isolated by per se known method and purified by the routine purification procedure such as recrystallization, distillation, chromatography, etc.

Compound (I) can also be produced by subjecting compound (XV) and compound (XVI) to reductive condensation using hydrogen and a hydrogenation catalyst such as platinum oxide, palladium on carbon, Raney nickel, Raney cobalt, or the like. The proportion of the hydrogenation catalyst relative to compound (XV) is about 0.1 to 1000 weight %, preferably about 1 to 300 weight %. This reaction can be advantageously carried out in an invert solvent. There is no particular limitation on the kind of solvent that can be used unless the reaction is interfered with but preferred solvent are alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., organic acids such as formic acid, acetic acid, etc., and mixtures of such solvents. Though it depends on the activity and amount of the catalyst used, the reaction time is generally 10 minutes to 100 hours, preferably 10 minutes to 10 hours. The reaction temperature is generally 0–120° C., preferably 20–80° C. When the hydrogenation catalyst is used, the hydrogen pressure is generally 1 to 100 atmospheres. After completion of the reaction, the reaction mixture can be submitted to the next reaction either as it is or after partial purification but the objective compound produced in the reaction mixture can be easily isolated by per se known method and purified by the routine purification procedure such as recrystallization, distillation, chromatography, etc.

Reaction scheme 4

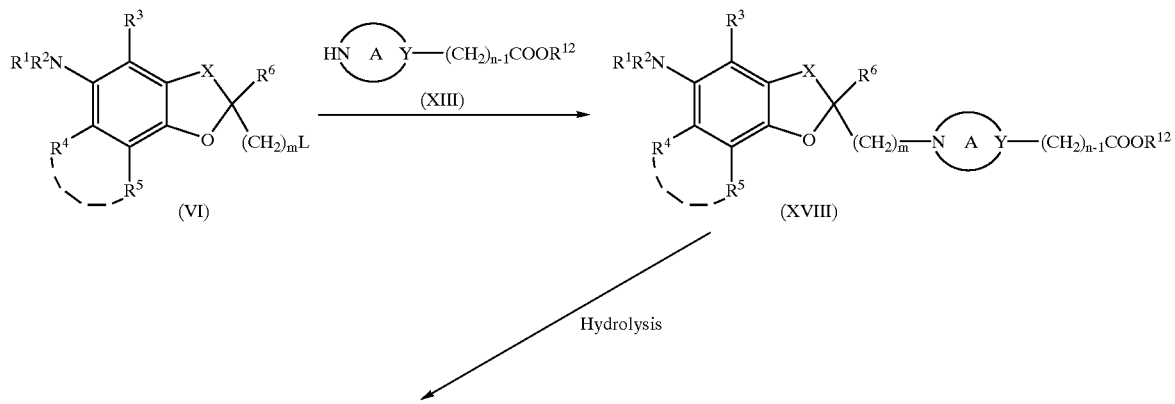

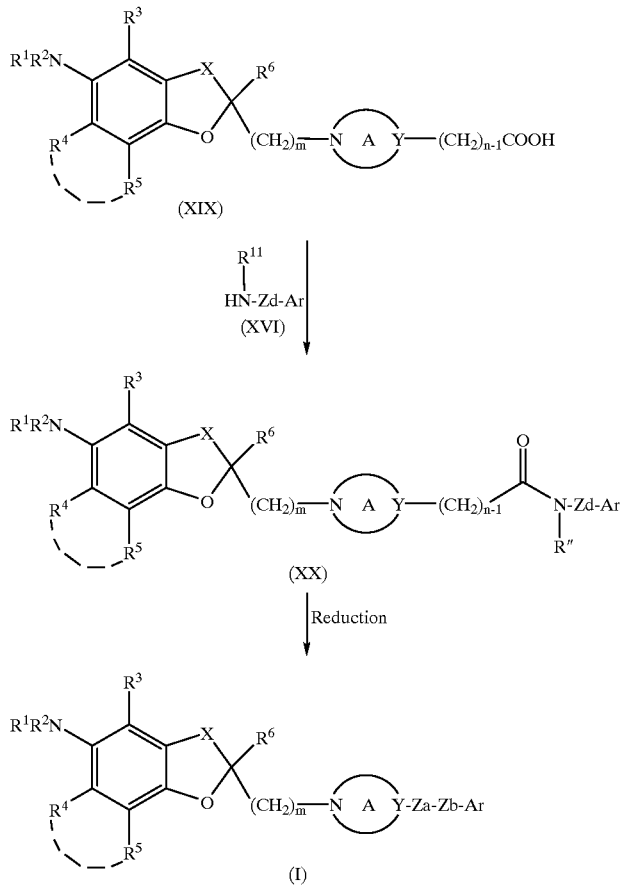

Compound (XVIII) (wherein $R^{12}$ represents a hydrogen atom or a hydrocarbon group; n has the same meaning as defined above) can be produced by subjecting compound (VI) and compound (XVII) (wherein the respective symbols have the same meanings as defined above) to a condensation similar to that used in the production of compound (I) from compound (VI).

The "hydrocarbon group" for $R^{12}$ may be similar to the "hydrocarbon group" of the "hydrocarbon group which may be substituted" as mentioned for $R^{10}$.

Compound (XVII) can be purchased and used, when it is commercially available or be obtained by per se known method, for example the method described in J. Am. Chem. Soc., 75, 6249, 1953, etc.

Compound (XIX) (wherein n has the same meaning as defined above) can be produced by subjecting compound (XVIII) to acid or alkaline hydrolysis. The acid hydrolysis can be carried out using, for example, a mineral acid such as hydrochloric acid, sulfuric acid, etc., a Lewis acid such as boron trichloride, boron tribromide, etc., a combination of a Lewis acid with either a thiol or a sulfide, or an organic acid such as trifluoroacetic acid, p-toluenesulfonic acid, etc. The alkaline hydrolysis can be carried out using a metal hydroxide such as sodium hydroxide, potassium hydroxide, barium hydroxide, etc., a metal carbonate such as sodium carbonate, potassium carbonate, etc., a metal alkoxide such as sodium methoxide, sodium ethoxide, potassium tert-butoxide, etc., or an organic base such as triethylamine, imidazole, formamidine, etc., for instance. The acid or base is used in a proportion of about 0.5 to 20 mols, preferably about 0.5 to 10 mols, per mol of compound (XVIII). This reaction can be advantageously carried out in the absence of a solvent or in an inert solvent. There is no particular limitation on the kind of solvent that can be used unless the reaction is interefered with. Preferred are alcohols such as methanol, ethanol, propanol, etc., aromatic hydrocarbons such as benzene, toluene, etc., saturated hydrocarbons such as cyclohexane, hexane, etc., organic acids such as formic acid, acetic acid, etc., ethers such as tetrahydrofuran, dioxane, 1,2-dimethoxyethane, etc., amides such as N,N-dimethylformamide, N,N-dimethylacetamide, etc., halogenated hydrocarbons, such as dichloromethane, chloroform, carbon tetrachloride, 1,2-dichloroethane, etc., nitriles such as acetonitrile, propionitrile, etc., ketones such as acetone, methyl ethyl ketone, etc., sulfoxides such as dimethyl sulfoxide etc., water, and mixtures of such solvents. The reaction time is generally 10 minutes to 60 hours, preferably 10 minutes to 12 hours. The reaction temperature is generally −10–200° C., preferably 0–120° C. Thus obtained compound (XIX) can be submitted to the next reaction either as the reaction mixture or after partial purification but can be easily isolated by per se known method and purified by the routine purification procedure such as recrystallization, distillation, chromatography, etc.

Compound (XX) (wherein n and ZD have the same meanings as respectively defined above) can be produced by subjecting compound (XVI) to condensation with compound (XIX), a reactive derivative of compound (XIX) or a salt of compound (XIX) in the same manner as described for the production of compound (XI) from compound (X).

Compound (I) can also be produced by subjecting compound (XX) to reduction in the same manner as described for the production of compound (I) from compound (XI).

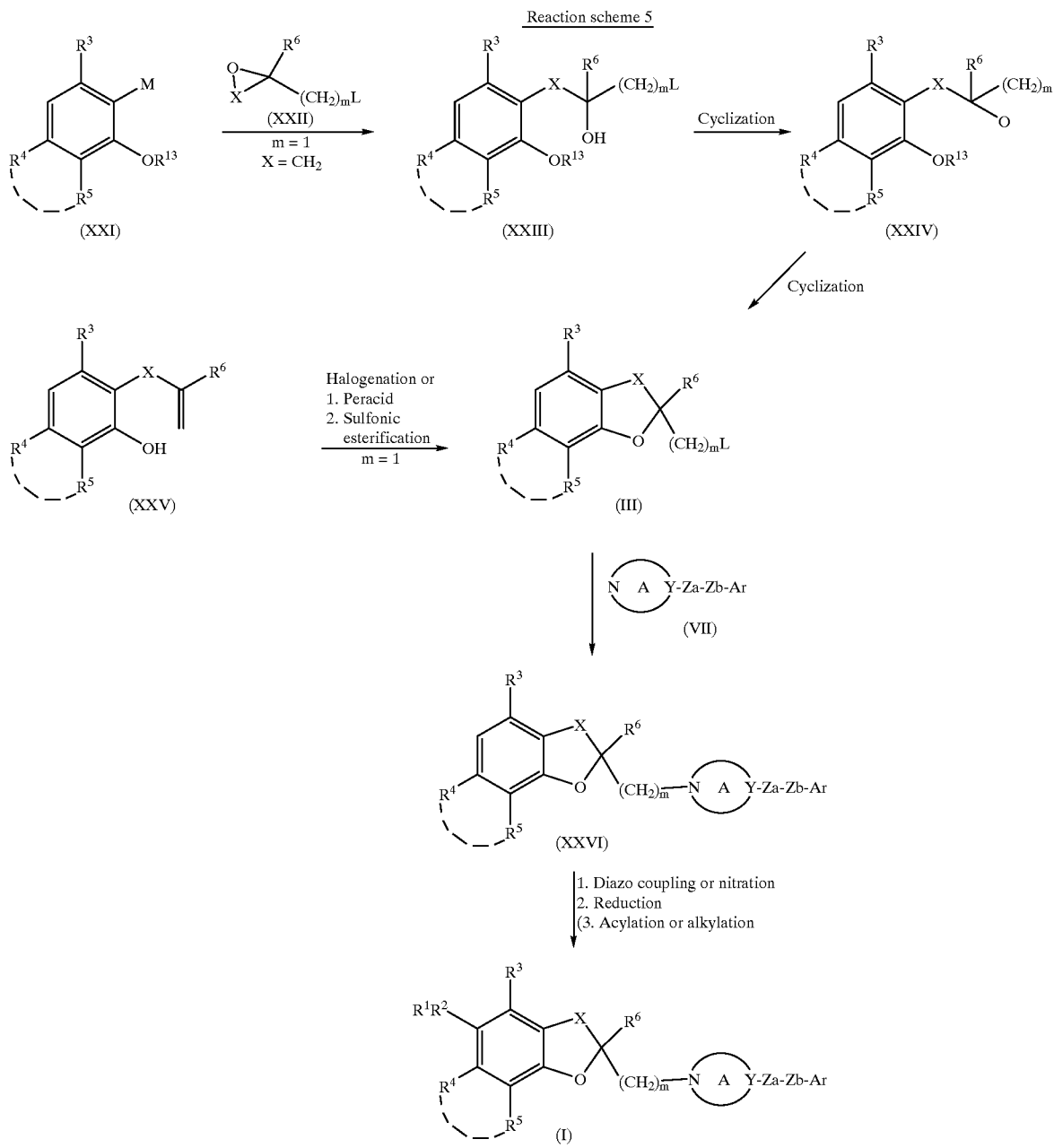

Reaction scheme 5

Compound (XXI) (wherein M represents a metal and $R^{13}$ represents a hydrocarbon group which may be substituted or a silyl) can be produced by the per se known technology, for example the process described in JP-A-5-140142 or any process analogous thereto.

The "metal" for M includes, for example, alkali metals such as lithium, sodium, etc., alkaline earth metals such as magnesium etc., copper, zinc, boron, aluminum, cerium, and titanium.

The "hydrocarbon group which may be substituted" for $R^{13}$ includes the "hydrocarbon group which may be substituted" as mentioned for $R^{10}$.

The "sylyl" for $R^{13}$ includes, for example, tri $C_{1-6}$ alkylsilyl (e.g. trimethylsilyl, tert-butyldimethylsilyl).

Compound (XXII) (wherein the respective symbols have the meanings defined above) can be produced by the per se known technology, for example the processes described in Journal of The American Chemical Society, 109, 5765–5780, 1987 or any processes analogous thereto.

Compound (XXV) can be produced by the per se known technology, for example the processes described in JP-A-5-140142 and other literature or any processes analogous thereto.

Among species of compound (XXIII) (wherein the respective symbols have the meanings defined above), the compound wherein m=1 and X=methylene can be produced by subjecting compound (XXI) and compound (XXII) wherein m=1 and X=methylene or condensation. Compound (XXI) is used in a proportion of about 0.8 to 10 mols, preferably about 1.0 to 5.0 mols, per mol of compound (XXII). This reaction can be conducted with advantage in an inert solvent (i.e. a solvent indifferent to the reaction; the same applies hereinafter). There is no particular limitation on the type of solvent that can be used. Preferred, however, are ethers such as diethyl ether, tetrahydrofuran, dioxane, 1,2-dimethoxyethane, etc., hydrocarbons such as benzene, toluene, cyclohexane, etc., and mixtures of such solvents. The reaction time is generally 10 minutes to 100 hours and preferably 10 minutes to 10 hours. The reaction temperature is generally −100° C. to 30° C. and preferably −80° to 20° C. This reaction can be carried out optionally in the presence of an additive. The additive mentioned just above includes boron trifluoride complexes such as boron trifluoride-diethyl ether, boron trifluoride-dimethyl sulfide, etc. and copper salts such as copper (I) iodide. The additive is used in a proportion of about 0.1 to 3.0 mols, preferably about 0.5 to 1.5 mols, per mol of compound (XXII). The reaction mixture thus obtained can be used, either as it is or in a partially purified form, for the next reaction but the product compound can be easily isolated from the reaction mixture and further purified by such separatory procedures as recrystallization, distillation, chromatography, etc.

Among species of compound (XXIV) (wherein the respective symbols have the meanings defined above), the compound wherein m=1 and X=methylene can be produced by subjecting compound (XXIII) wherein m=1 and X=methylene to cyclization with the aid of a base. The base that can be used for this purpose includes, for example, inorganic bases such as sodium hydroxide, potassium hydroxide, etc., basic salts such as sodium carbonate, potassium carbonate, cesium carbonate, sodium hydrogen carbonate, etc., aromatic amines such as pyridine, lutidine, etc., tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylpyrrolidine, N-methylmorpholine, etc., alkali metal hydrides such as sodium hydride, potassium hydride, etc., metal amides such as sodium amide, lithium, diisopropylamide, lithium hexamethyldisilazide, etc., and metal alkoxides such as sodium methoxide, sodium ethoxide, potassium tert-butoxide, etc. The base is used in a proportion of about 1.0 to 5.0 mols, preferably about 1.0 to 2.0 mols, per mol of compound (XXIII). This reaction can be advantageously carried out in an inert solvent. There is no particular limitation on the type of solvent that can be used. Preferred are alcohols such as methanol, ethanol, propanol, etc., ethers such as diethyl ether, tetrahydrofuran, dioxane, 1,2-dimethoxymethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitriles such as acetonitrile, propionitrile, etc., sulfoxides such as dimethyl sulfoxide etc., water, and mixtures of such solvents. The reaction time is generally 5 minutes to 3 hours and preferably 5 minutes to 2 hours. The reaction temperature is generally −20° C. to 200° C. and preferably −10° C. to 120° C.

Among species of compound (III) (wherein the respective symbols have the meanings defined above), the compound wherein m=1 and X=methylene can be produced alternatively by subjecting compound (XXIV) wherein m=1 and X=methylene to deprotection of $R^{13}$ using acid or base as a catalyst and subsequent cyclization. The catalyst that can be used for this purpose includes a mineral acid such as hydrochloric acid, sulfuric acid, hydrobromic acid, etc., an organic acid such as acetic acid, trifluoroacetic acid, etc., boron trifluoride-diethyl ether, a Lewis acid such as zinc chloride, tin chloride, etc., a sulfonic acid such as p-toluenesulfonic acid, methanesulfonic acid, etc.,m an inorganic base such as sodium hydroxide, potassium hydroxide, etc., a basic salt such as sodium carbonate, potassium carbonate, cesium carbonate, sodium hydrogen carbonate, etc., an aromatic amine such as pyridine, lutidine, etc., a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., an alkali metal hydride such as sodium hydride, potassium hydride, etc., a metal amide such as sodium amide, lithium diisopropylamide, lithium hexamethyldisilazide, etc., or a metal alkoxide such as sodium methoxide, sodium ethoxide, potassium tert-butoxide, etc. Relative to each mol of compound (XXIV), acid or base is used in a proportion of about 0.1 to 30 mols, preferably about 0.5to 10 mols. This reaction can be advantageously carried out in an inert solvent. There is no particular limitation on the type of solvent that can be used. Preferred are alcohols such as methanol, ethanol, propanol, etc., ethers such as diethyl ether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., halogenated hydrocarbons such as dichloromethane, chloroform, 1,2-dichloroethane, carbon tetrachloride, etc., nitriles such as acetonitrile, propionitrile, etc., ketones such as acetone, methyl ethyl ketone, etc., water, and mixtures of such solvents. The reaction time is generally 5 minutes to 100 hours and preferably 5 minutes to 3 hours. The reaction temperature is generally −20° C. to 120° C. and preferably 0° to 80° C. The reaction mixture thus obtained can be used, either as it is or in a partially purified form, for the next reaction but the product compound can be easily isolated from the reaction mixture and further purified by such separatory procedures as recrystallization, distillation, chromatography, etc.

Among species of compound (III) (wherein the respective symbols have the meanings defined above), the compound in which m=1 and X=methylene can also be produced from compound (XXV) wherein X=methylene in the same manner as the production of compound (VI) from compound (V).

Compound (XXVI) can be produced by subjecting compound (III) and compound (VII) to condensation in the same manner as the production of compound (I) from compound (VI).

Compound (I) can also be produced by nitrating compound (XXVI) in the same manner as in the process for production of compound (IV) from compound (III) and then reducing the nitro group in the same manner as in the process for production of compound (VI) from compound (IV). Moreover, the alkylation and acylation reactions to which compound (VI) is optionally subjected can be carried out in combination or in repetition. The reaction mixture thus obtained can be used, either as it is or in a partially purified form, for the next reaction but the product compound can be easily isolated from the reaction mixture by per se known methods and further purified by such separatory procedures as recrystallization, distillation, chromatography, etc.

Compound (I) can be produced by subjecting compound (XXVI) to diazo coupling reaction with a diazonium salt followed by reduction of the resulting azo compound. The diazionium salt that can be used includes aryldiazonium salts such as benzenediazonium chloride, 4-nitrobenzenediazonium chloride, 2,4-dinitrobenzenediazonium chloride, as it is or in a partially purified for, for the next reaction but the product compound can be easily isolated from the reaction mixture by per se known methods and further purified by such separatory procedures as recrystallization, distillation, chromatography, etc.

Furthermore, by using an optically active species of compound (XXII) as a starting material, an optically active species of compound (I) can be easily synthesized.

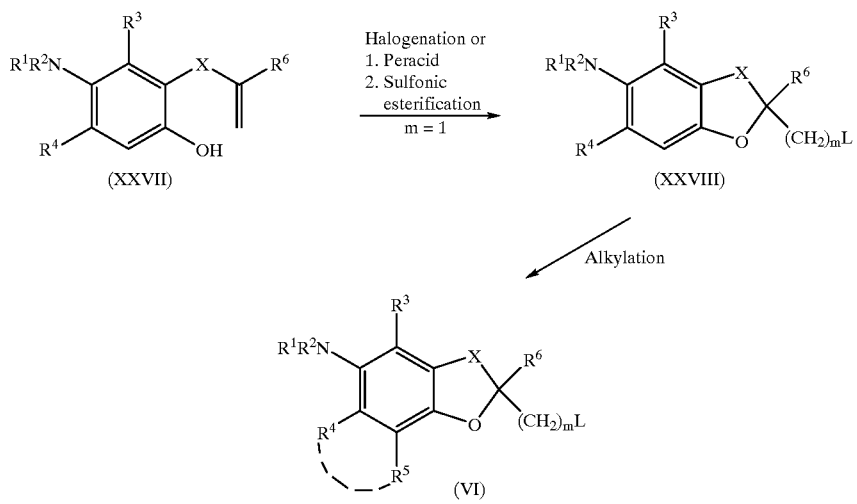

4-sulfobenzenediazonium chloride, etc. The diazonium salt can be prepared by the per se known technology, for example by the processes described in JP-A-5-140142 and other literature or any processes analogous thereto. This diazonium compound is used in a proportion of about 0.8 to 3 mols per mol of compound (XXVI). This diazo coupling reaction can be carried out advantageously in an invert solvent. There is no particular limitation on the inert solvent that can be used only if the reaction can proceed therein. Preferred, however, are ethers such as diethyl ether, tetrahydrofuran, dioxane, 1,2-dimethoxyethane, etc., hydrocarbons such as benzene, toluene, cyclohexane, etc., amides such as N,N-dimethylformamide, N,N-dimethylacetamide, etc., halogenated hydrocarbons such as dichloromethane, chloroform, 1,2-dichloroethane, carbon tetrachloride, etc., nitriles such as acetonitrile, propionitrile, etc., ketones such as acetone, methyl ethyl ketone, etc., organic acids such as acetic acid, propionic acid, etc., water, and mixtures of such solvents. The reaction time is generally 10 minutes to 100 hours, preferably 20 minutes to 30 hours. The reaction temperature is generally −20 ° C. to 80° C., preferably 0° C. to 50° C. The reaction mixture thus obtained can be used, either as it is or in a partially purified form, for the next reaction but the product compound can be easily isolated from the reaction mixture by per se known methods and further purified by such separatory procedures as recrystallization, distillation, chromatography, etc. The subsequent reduction of this azo compound can be carried out under the same conditions as those described for the production of compound (VI) from compound (IV). The alkylation and acylation reactions to which compound (VI) is optionally subjected can be optionally applied, in a suitable combination or either one in repetition, to compound (I) as well. The reaction mixture thus obtained can be used, either Compound (XXVII) can be obtained by the per se known method, for example, the processes disclosed in JP-A-5-140142, or any process analogous thereto.

Compound (XXVIII) (wherein L has the same meaning as defined above; m represents 1) can also be produced by treating compound (V) with a halogenation reagent. This reaction can be conducted with bases, basic salts or radical initiator or under light exposure, where necessary. The halogenation reagent includes, for example, halogen such as bromine, chlorine, or iodine, imide such as N-bromosuccinimide, halogen adduct such as benzyltrimethylammonium dichloroiodate, benzyltrimethylammonium tribromide, tetramethylammonium bromide bromine adduct, pyridinium bromide perbromide, dioxan dibromide. The halogenation reagent is used in a proportion of about 1.0 to 5.0 mols, preferably about 1.0 to 2.0 mols, per mol of compound (V). This reaction is preferably carried out in the absence of a solvent or in an inert solvent. There is no particular limitation on the kind of solvent only if progress of the reaction is not hindered. Preferred are ethers such as diethyl ether, tetrahydrofuran, dioxane, 1,2-dimethoxyethane, etc., alcohols such as methanol, ethanol, propanol, etc., hydrocarbons such as benzene, toluene, cyclohexane, hexane, etc., amides such as N,N-dimethylformamide, N,N-dimethylacetamide, etc., halogenated hydrocarbons, such as dichloromethane, chloroform, carbon tetrachloride, 1,2-dichloroethane, etc., nitriles such as acetonitrile, propionitrile, etc., sulfoxides such as dimethyl sulfoxide etc., organic acids such as acetic acid, propionic acid, etc., nitroalkanes such as nitromethane, etc., aromatic amines such as pyridine, lutidine, quinoline, etc., and mixtures of such solvents. The base that can be optionally used includes, for example, inorganic bases such as sodium carbonate, potassium carbonate, cesium carbonate, sodium hydrogen carbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The basic salt that can be optionally used includes, for example, sodium acetate, potassium acetate, etc. The radical initiator that can be optionally used includes, for example, benzoly peroxide, azobisisobutyronitrile, etc. In case the light exposure, halogen lamp can be used. The reaction temperature is about −50–150° C., preferably 0–100° C. The reaction time is generally 5 minutes to 24 hours, preferably 10 minutes to 5 hours.

Compound (XXVIII) can also be produced by a process which comprises cyclizing compound (XXVII) with an organic peracid optionally in the presence of a base and subjecting the resultant alcohol to sulfonic esterification. The organic peracid that can be used includes, for example, m-chloroperbenzoic acid and peracetic acid. The organic peracid is used in a proportion of about 1.0 to 5.0 mols, preferably about 1.0 to 2.0 mols, per mol of compound (XXVII). This reaction is preferably carried out in an inert solvent. There is no particular limitation on the kind of solvent that can be used unless the reaction is hindered. Preferred are water, ethers such as diethyl ether, tetrahydrofuran, dioxane, 1,2-dimethoxyethane, etc., hydrocarbons such as benzene, toluene, cyclohexane, hexane, etc., amides such as N,N-dimethylformamide, N,N-dimethylacetamide, etc., halogenated hydrocarbons such as dichloromethane, chloroform, carbon tetrachloride, 1,2-dichloroethane, etc., nitriles such as acetonitrile, propionitrile, etc., sulfoxides such as dimethyl sulfoxide etc., organic acids such as acetic acid, propionic acid, etc., aromatic amines such as pyridine, lutidine, quinoline, etc., and mixtures of such solvents. The base that can be optionally used includes, for example, inorganic bases such as sodium carbonate, potassium carbonate, cesium carbonate, sodium hydrogen carbonate, etc., aromatic amines such as pyridine, lutidine, etc., and tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The reaction temperature is about −20–150° C., preferably 0–100° C. The reaction time is generally 5 minutes to 24 hours and preferably 10 minutes to 5 hours. The next sulfonic esterification reaction can be carried out under the same conditions as described for the production of compound (III) from compound (II). Thus obtained compound (XXVII) can be submitted to the next reaction either as the reaction mixture or after partial purification, but can be easily isolated by per se known method and purified by the routine purification procedures such as recrystallization, distillation, chromatography, etc.

Compound (VI) can be obtained by subjecting compound (XXVIII) to alkylation in the presence of a proton acid or a Lewis acid. The alkylating agent includes, for example, alcohols such as methanol, ethanol, isopropylalcohol, tert-butylalcohol, etc., halogenated hydrocarbons such as isopropylchloride, tert-butylchloride, etc., alkenes such as isobutene, etc., esters such as isopropyl acetate, tert-butyl acetate, diisopropyl sulfate, isopropyl p-toluenesulfonate, isopropyl phosphite, etc., ethers such as tert-butyl methyl ether, etc. The alkylating agent is used in a proportion of about 1.0 to 30 mols, preferably about 1.0 to 15 mols, per mol of compound (XXVIII). The proton acid that can be used includes, for example, conc. sulfuric acid, trifluoro acetic acid, etc. The Lewis acid that can be used includes, for example, such as aluminum chloride, aluminum bromide, iron (III) chloride, tin (IV) chloride, titanium chloride, zinc chloride, etc. The proton acid and the Lewis acid can be used solely or in their combination. The proton acid is used in a proportion of about 1.0 to 200 mols. preferably about 1.0 to 100 mols, per mol of compound (XXVIII). The Lewis acid is used in a proportion of about 1.0 to 5.0 mols, preferably about 1.0 to 2.0 mols, per mold of compound (XXVIII). This reaction is advantageously carried out in an inert solvent. There is no particular limitation on the kind of solvent. Preferred are hydrocarbons such as benzene, toluene, xylene, cyclohexane, hexane, etc., halogenated hydrocarbons such as dichloromethane, chloroform, carbon tetrachloride, 1,2-dichloroethane, tetrachloroethane, etc., nitriles such as acetonitrile, propionitrile, etc., nitroalkanes such as nitromethan, etc., and mixtures of such solvents. The reaction temperature is generally −20 −200° C., preferably 0–150° C. The reaction time is generally 5 minutes to 24 hours, preferably 10 minutes to 5 hours. Thus obtained compound (VI) can be submitted to the next reaction either as the reaction mixture or after partial purification, but can be easily isolated by per se known method and purified by the routine purification procedures such as recrystallization, distillation, chromatography, etc.

Referring to the above reactions, where the starting compounds have amino, carboxyl or/and hydroxy as substituent (s), the compounds may be such that the protective groups in common usage in peptide chemistry may have been introduced into these functions and the objective compounds can be obtained by removing the protective groups as necessary.

The protective group for the amino function includes, for example, formyl and a $C_{1-6}$ alkyl-carbonyl (e.g. acetyl, propionyl, etc.), phenylcarbonyl, $C_{1-6}$ alkoxy-carbonyl (e.g. methoxycarbonyl, ethoxycarbonyl, etc.), phenyloxycarbonyl, $C_{7-10}$ aralkyloxy-carbonyl (e.g. benzyloxycarbonyl etc.), trityl and phthaloyl group, each of which may be substituted. The substituent here may for example be halogen (e.g. fluorine, chlorine, bromine, iodine, etc.), $C_{1-6}$ alkyl-carbonyl (e.g. acetyl, propionyl, valeryl, etc.), nitro, etc. The number of substituents that may be present is 1 to 3.

The protective group for the carboxyl function includes, for example, a $C_{1-6}$ alkyl (e.g. methyl, ethyl, propyl, isopropyl, butyl, tert-butyl, etc.), phenyl, trityl and silyl group, each of which may be substituted. The substituent here may for example be halogen (e.g. fluorine, chlorine, bromine, iodine, etc.), formyl, $C_{1-6}$ alkyl-carbonyl (e.g. acetyl, propionyl, butylcarbonyl, etc.), nitro, $C_{1-6}$ alkyl (e.g. methyl, ethyl, tert-butyl, etc.), and $C_{6-10}$ aryl (e.g. phenyl, naphthyl, etc.), among others. The number of substituents that may be present is 1 to 3.

The protective group for the hydroxy function includes, for example, a $C_{1-6}$ alkyl (e.g. methyl, ethyl, propyl, isopropyl, butyl, tert-butyl, etc.), phenyl, $C_{7-11}$ aralkyl (e.g. benzyl etc.), formyl, $C_{1-6}$ alkyl-carbonyl (e.g. acetyl, propionyl, etc.), phenyloxycarbonyl, $C_{7-11}$ aralkyl-oxycarbonyl (e.g. benzyloxycarbonyl etc.), tetrahydropyranyl, tetrahydrofuranyl and silyl group, each of which may be substituted. The substituent may for example be halogen (e.g. fluorine, chlorine, bromine, iodine, etc.), $C_{1-6}$ alkyl (e.g. methyl, ethyl, tert-butyl, etc.), $C_{7-11}$ aralkyl (e.g. benzyl etc.), $C_{6-10}$ aryl (e.g. phenyl, naphthyl, etc.), and nitro, among others. The number of substituents that may be present is 1 to 4.

The protective groups can be removed by per se known procedures or procedures analogous thereto. For example, treatment with an acid, a base, ultraviolet light, hydrazine, phenylhydrazine, sodium N-methyldithiocarbamate, tetrabutylammonium fluoride, palladium acetate or the like or reduction can be mentioned.

In any event, where desired, any known deprotection, acylation, alkylation, hydrogenation, oxidation, reduction, carbon chain extending reaction, and substituent exchange reaction can be used independently or in combination in synthesizing compound (I). Those reactions can be carried out, for example, by the methods described in inter alia Shin Jikken Kagaku Koza (New Series in Experimental Chemistry) 14 and 15, 1977 (Maruzen Publishing Co.), etc.

Where the objective compound is obtained in the free form, it can be converted to a salt in the routine manner. Where the objective compound is obtained as a salt, it can be converted to the free compound or a different kind of salt. Thus obtained compound (I) can be isolated and purified from the reaction mixture by per se known procedures such as redistribution, concentration, solvent extraction, fractional distillation, crystallization, recrystallization, and chromatography.

In case compound (I) exists as configurational isomers (position isomers), diastreomers conformers, the respective isomers can be isolated by the above-described fractionated and purification technology. In case compound (I) is a racemic compound, it can be fractionated into (S) and (R) forms by any conventional optical resolution method. Compound (I) may be a hydrate or an anhydrous compound.

The compound (I) of the present invention and compound (Ia) show a high affinity for the sodium channel, particularly for site 2, with a low toxic potential and a low risk for adverse effects, thus being of value as safe drugs.

Compounds (I) and (Ia) act as sodium channel modulators in mammals (e.g. mouse, rat, hamster, rabbit, cat, dog, bovine, sheep, monkey, human, etc.) and can be used as prophylactic and/or therapeutic agents for various diseases and disorders of the central nervous system, such as central nervous system ischemia, central nervous system trauma (e.g. brain trauma, spinal cord injury, whiplash injury, etc.) epilepsy, neurodegenerative diseases (e.g. amyotrophic lateral sclerosis (ALS), Alzheimer's disease, Huntigton's chorea, Parkinson's disease, diabetic neuropathy, etc.), vascular dementia (e.g. multi-infarct dementia, Binswanger's disease, etc.) manic-depressive psychosis, depression, schizophrenia, chronic pain, trigeminal neuraligia, migraine, cerebral edema, and so on. In addition, compounds (I) and (Ia) have potent antioxidant and dopamine transporter modulating activities and are, therefore, of value as prophylactic and therapeutic agents for the above diseases and ischemic cardiovascular diseases (e.g. myocardial infarction, angina pectoris, etc.), and atherosclerosis, among other diseases. Among others, a prophylactic and/or therapeutic agent for central nervous system ischemia, central nervous system trauma, neurodegenerative diseases or cerebral edema.

Each of compounds (I) and (Ia) is only sparingly toxic and can be administered safely either as it is alone or in the form of a pharmaceutical composition prepared by formulating it with a pharmacologically acceptable carrier in accordance with established pharmaceutical practice in such dosage forms as tablets (including dragees and film-coated tablets), powders, granules, capsules (including soft capsules), solutions, injections, suppositories, and controlled release dosage forms, whether orally or by other routes (e.g. topically, rectally, intravenously, etc.). The proportion of compound (I) or (Ia) in the pharmaceutical composition of the invention may range from about 0.01% to about 100% by weight. The dosage depends on characteristics of the patient or recipient, the route of administration, the disease to be treated, and other factors. Generally speaking, when an injectable dosage form is administered to an adult patient for the treatment of a brain trauma, the recommended dosage in terms of active ingredient [compound (I) or compound (Ia)] is about 0.05 to 30 mg/kg body weight, preferably about 0.1 to 20 mg/kg body weight, more preferably about 0.1 to 5 mg/kg body weight, and still more preferably about 0.1 to 2 mg/kg body weight daily in a single dose or in a few divided doses. Compound (I) or (Ia) can be used in combination with other active substance (e.g. an antithrombotic agent such as argatroban etc., a thrombolytic agent such as urokinase, tissue plasminogen activator, etc., a platelet aggregation inhibitor such as ozagrel, etc., an anticoagulant such as heparin etc., a histamine receptor antagonist such as cimetidine, famotidine, etc., an antiparkinsonian drug such as dopamine, levodopa, etc., a hydantoin series anticonvulsant such as phenytoin, mephenytoin, ethotoin, etc., barbital series anticonvulsants or analgesics such as phenobarbital, mephorbarbital, metharbital, etc., a calcium channel blocker such as diltiazem, etc., imipenem-cilastatin sodium, glycerol, etc.). Thus, any of these other active substances can be formulated in combination with compound (I) or (Ia) in the routine manner to provide a pharmaceutical composition (e.g. tablets, powders, granules, capsules (including soft capsules), solutions, injections, suppositories, controlled release dosage forms, etc.).

The pharmacologically acceptable carrier that can be used in the manufacture of a pharmaceutical composition of the present invention includes various kinds of organic or inorganic carriers which are generally used in pharmaceutical practice, such as the excipient, lubricant, binder, and disintegrator for solid preparations or the solvent, solubilizer, suspending agent, isotonizing agent, buffer, and local anesthetic or soothing agent for liquid preparations. Where necessary, such common additives as the antiseptic, antioxidant, colorant, sweetener, adsorbent, wetting agent, etc. can also be incorporated.

The excipient includes lactose, sucrose, D-mannitol, starch, corn starch, crystalline cellulose, light silicic anhydride, etc.

The lubricant includes magnesium stearate, calcium stearate, talc, colloidal silica, etc.

The binder includes, for example, crystalline cellulsoe, sucrose, D-mannitol, dextrin, hydroxypropylcellulose, hydroxypropylmethylcellulose, polyvinylpyrrolidone, starch, cans sugar, gelatin, methylcellulose, carboxymethylcellulose sodium, etc.

The disintegrator includes starch, carboxymethylcellulose, carboxymethylcellulose calcium, croscarmellose sodium, carboxymethylstarch sodium, L-hydroxypropylcellulose, etc.

The solvent includes water for injection, alcohol, propylene glycol, macrogols, sesame oil, corn oil, olive oil, etc.

The solubilizer includes polyethylene glycol, propylene glycol, D-mannitol, benzyl benzoate, ethanol, trisaminomethane, cholesterol, triethanolamine, sodium carbonate, sodium citrate, etc.

The suspending agent includes a variety of surfactants such as stearyltriethanolamine, sodium lauryl sulfate, laurylaminopropionic acid, lecithin, benzalkonium chloride, benzethonium chloride, glyceryl monostearate, etc. and hydrophilic macromolecular substances such as polyvinyl alcohol, polyvinylpyrrolidone, carboxymethylcellulose sodium, methylcellulose, hydroxymethylcellulose, hydroxyethylcellulose, hydroxypropylcellulose, etc.

The isotonizing agent includes glucose, D-sorbitol sodium chloride, glycerin, D-mannitol, etc.

The buffer includes phosphate, acetate, carbonate, citrate, etc.

The local anesthetic includes benzyl alcohol, etc.

The antiseptic includes p-hydroxybenzoic acid esters, chlorobutanol, benzyl alcohol, phenethyl alcohol, dehydroacetic acid, sorbic acid, etc.

The antioxidant includes sulfites, ascorbic acid, α-tocopherol, etc.

BEST MODE FOR CARRYING OUT OF THE INVENTION

The following reference examples, examples, formulation examples and experimental examples are intended to describe the present invention in further detail and should by no means be construed as defining the scope of the invention.

As used in the following reference and working examples, the term "room temperature" generally means about 10° C.–35° C. The symbol % stands for percentage by weight unless otherwise indicated; provided, however, that all yield values are in mol/mol %.

Basic silica gel used was NH-DM1020, which was manufacturered by Fuji Silysia Chemical Ltd.

The other abbreviations used in the text have the following meanings.

s: singlet
d: doublet
t: triplet
q: quartet
m: multiplet
dd: double doublet
dt: double triplet
br: broad
J: coupling constant
Hz: Hertz
$CDCl_3$: deuterated chloroform
$DMSO-d_6$: deuterated dimethyl sulfoxide
$CD_3OD$: deuterated methanol
$^1H$-NMR: proton nuclear magnetic resonance

EXAMPLES

Reference Example 1

2,3-Dihydro-2-[[4-(4-methoxyphenyl)-1-piperazinyl]methyl]-2,4,6,7-tetramethyl-5-benzofuranamine trihydrochloride In an autoclave, a mixture of 2-bromomethyl-2,3-dihydro-2,4,6,7-tetramethyl-5-benzofuranamine (1.5 g), 1-(4-methoxyphenyl)piperazine (2.0 g), and triethylamine (1.6 g) was stirred under argon gas at 180° C. for 15 hours. After cooling, the reaction mixture was treated with saturated sodium hydrogen carbonate ($NaHCO_3$)/water and extracted with ethyl acetate. The extract was washed with saturated aqueous sodium chloride and dried over anhydrous magnesium sulfate ($MgSO_4$) and the solvent was distilled off under reduced pressure. The residue was purified by silica gel column chromatography (ethyl acetate:hexane=9:1) and treated with 4N-hydrogen chloride solution in ethanol to provide the trihydrochloride. This product was recrystallized from ethanol to provide 0.53 g of the title compound. Yield 20%.

m.p. 194–196° C.

$^1H$-NMR (DMSO-$d_6$) δ: 1.62 (3H, s), 2.08 (3H, s), 2.25 (6H, s), 3.05 (1H, d, J=16.2 Hz), 3.34–3.63 (11H, m), 3.71 (3H, s), 6.88 (2H, d, J=9.0 Hz), 7.05 (2H, d, J=9.0 Hz), 9.92 (2H, br, s).

Reference Example 2

2-[[4-(2-Chlorophenyl)-1-piperazinyl]methyl]-2,3-dihydro-2,4,6,7-tetramethyl-5-benzofuranamine dihydrochloride A suspension of 2-bromomethyl-2,3-dihydro-2,4,6,7-tetramethyl-5-benzofuranamine (1.4 g), 1-(2-chlorophenyl)piperazine hydrochloride (1.4 g), and potassium carbonate (2.1 g) in N,N-dimethylformamide (15 mL) was stirred under nitrogen gas at 145° C. for 20 hours. This reaction mixture was diluted with water and extracted with ethyl acetate. The pooled organic layer was washed with water and saturated aqueous sodium chloride, dried over anhydrous sodium sulfate ($Na_2SO_4$) and silica gel (eluted with ethyl acetate), and concentrated under reduced pressure. The residue was purified by silica gel column chromatography (hexane:ethylacetate=5:1 to 2:1). The 2-[[4-(2-chlorophenyl)-1-piperazinyl]methyl)]-2,3-dihydro-2,4,6,7-tetramethyl-5-benzofuranamine thus obtained was dissolved in methanol and a stoichiometric excess of 10% hydrogen chloride solution in methanol was added. The mixture was concentrated under reduced pressure and recrystallized from ethanol/diethyl ether to provide 1.0 g of the title compound. Yield 44%.

m.p. 167–171° C.

$^1H$-NMR (DMSO-$d_6$) δ: 1.61 (3H, s), 2.07 (3H, s), 2.23 (3H, s), 2.25 (3H, s), 3.06 (1H, d, J=16.6 Hz), 3.1–3.9 (11H, m), 7.0–7.25 (2H, m), 7.3–7.5 (2H, m)

Reference Example 3

2,3-Dihydro-2,4,6,7-tetramethyl-2-[[4-(4-pyridyl)-1-piperidinyl]methyl]-5-benzofuranamine In an autoclave, a mixture of 2-bromomethyl-2,3-dihydro-2,4,6,7-tetramethyl-5-benzofuranamine (0.85 g), 4-(4-piperidinyl)pyridine (0.97 g), and triethylamine (1.3 mL) was stirred under nitrogen gas at 180° C. for 15 hours. To this reaction mixture were added saturated aqueous $NaHCO_3$ and ethyl acetate. The organic layer was separated and the aqueous layer was extracted with ethyl acetate. The pooled organic layer was washed with water and saturated aqueous NaCl, dried over $MgSO_4$, filtered, and concentrated under reduced pressure. The residue was purified by silica gel column chromatography (chloroform:methanol=20.1) and crystallized from ethyl acetate/hexane to provide 0.77 g of the title compound. Yield 70%.

m.p. 126–128° C.

$^1H$-NMR (CDCl$_3$) δ: 1.45 (3H, s), 1.5–1.9 (4H, m), 2.0–2.5 (3H, m), 2.08 (6H, s), 2.11 (3H, s), 2.52 (1H, d, J=13.9 Hz), 2.61 (1H, d, J=13.9 Hz), 2.83 (1H, d, J=15.4 Hz), 2.95–3.3 (2H, m), 3.13 (1H, d, J=15.4 Hz), 7.1–7.2 (2H, m), 8.45–8.55 (2H, m).

Reference Example 4

1-[(5-Amino-2,3-dihydro-2,4,6,7-tetramethylbenzofuran-2-yl)methyl]-N-phenyl-4-piperidinamine Using N-phenyl-4-piperidinamine and proceeding otherwise in the same manner as Reference Example 3, the title compound was provided. Yield 69%.

m.p. 116–118° C. (crystallized from ethyl acetate/hexane).

$^1$NMR (CDCl$_3$) δ: 1.2–1.6 (2H, m), 1.43 (3H, s), 1.9–2.2 (2H, m), 2.07 (6H, s), 2.09 (3H, s), 2.2–2.45 (2H, m), 2.50 (1H, d, J=13.8 Hz), 2.58 (1H, d, J=13.8 Hz), 2.8–2.95 (1H, m), 2.81 (1H, d, J=32 15.0 Hz), 3.0–3.35 (2H, m), 3.11 (1H, d, J=15.0 Hz), 6.5–6.7(3H, m), 7.1–7.2 (2H, m).

Reference Example 5

1-[(5-Amino-2,3-dihydro-2,4,6,7-tetramethylbenzofuran-2-yl)methyl]-4-(4-chlorophenyl)-4-piperidinol A suspension of 2-bromomethyl-2,3-dihydro-2,4,6,7-tetramethyl-5-benzofuranamine (1.4 g) and 4-(4-chlorophenyl)-4-hydroxypiperidine (1.3 g) in xylene (10 mL) was stirred under nitrogen gas at 120° C. for 1.5 hours and, then, refluxed for 16 hours. Thereafter, 0.85 g of 4-(4-chlorophenyl)-4-hydroxypiperidine was added and the mixture was refluxed for 24 hours. After cooling, the reaction mixture was filtered and washed with diethyl ether. The filtrate was extracted with 1N-hydrochloric acid and the aqueous layer was made weakly acidic with saturated aqueous sodium hydrogen carbonate ($NaHCO_3$). This aqueous layer was washed with diethyl ether and made weakly basic with saturated aqueous $NaHCO_3$. This solution was extracted with ethyl acetate and the organic layer was washed with saturated aqueous NaCl, dried over $MgSO_4$, filtered, and concentrated under reduced pressure. The residue was crystallized from diethyl ether/hexane to provide 0.58 g of the title compound. Yield 28%.

m.p. 118–120° C.

$^1$H-NMR ($CDCl_3$) δ: 1.45 (3H, s), 1.5–1.8 (2H, m), 1.9–2.2 (2H, m), 2.07 (6H, s), 2.10 (3H, s), 2.5–2.7 (4H, m), 2.7–2.9 (1H, m), 2.83 (1H, d, J=15.4 Hz), 2.9–3.05 (1H, m), 3.13 (1H, d, J=15.4 Hz), 7.29 (2H, d, J=8.8 Hz), 7.42 (2H, d, J=8.8 Hz).

Reference Example 6

N-[2,3-dihydro-2,4,6,7-tetramethyl-2-[(4-phenyl-1-piperidinyl)methyl]benzofuran-5-yl]acetamide To a suspension of 2,3-dihydro-2,4,6,7-tetramethyl-2-[(4-phenyl-1-piperidinyl)methyl]-5-benzofuranamine dihydrochloride (1.3 g) in tetrahydrofuran (10 mL) was added a solution of sodium carbonate (0.95 g) in water (5 mL) with ice-cooling and the mixture was stirred for 5 minutes. Then, 0.26 mL of acetyl chloride was added dropwise and the mixture was stirred at room temperature for 15 minutes. This reaction mixture was diluted with water and extracted with 2 portions of ethyl acetate. The pooled organic layer was washed with water and saturated aqueous NaCl, dried over $MgSO_4$, filtered, and concentrated under reduced pressure. The residue was crystallized from ethyl acetate/diisopropyl ether to provide 1.1 g of the title compound. Yield 90%.

m.p. 94–96° C.

$^1$H-NMR ($CDCl_3$) δ: 1.4–1.5 (3H, m), 1.6–1.9 (4H, m), 2.0–2.7 (17H, m), 2.81 (1H, d, J=15.4 Hz), 2.9–3.3 (3H, m), 6.5–6.7 (1H, m), 7.1–7.4 (5H, m).

Reference Example 7

N-[2,3-dihydro-2,4,6,7-tetramethyl-2-[(4-phenyl-1-piperazinyl)methyl]benzofuran-5-yl]acetamide hydrochloride Using 2,3-dihydro-2,4,6,7-tetramethyl-2-[(4-phenyl-1-piperazinyl)methyl]-5-benzofuranamine, the procedure of Reference Example 6 was otherwise repeated to provide N-[2,3-dihydro-2,4,6,7-tetramethyl-2-[(4-phenyl-1-piperazinyl)methyl]benzofuran-5-yl]acetamide. Yield 94%. This product was dissolved in tetrahydrofuran and after the solution was diluted with methanol, a stoichiometric excess of 10% HCl solution in methanol was added. The mixture was concentrated under reduced pressure and crystallized from ethanol/diethyl ether to provide the title compound.

m.p. 195–199° C.

$^1$H-NMR (DMSO-$d_6$) δ: 1.62 (3H, s), 1.97 (3H, s), 1.99 (3H, s), 2.02 (3H, s), 2.05 (3H, s), 3.01 (1H, d, J=15.8 Hz), 3.1–4.2 (11H, m), 6.85 (1H, t, J=7.1 Hz), 6.99 (2H, d, J=8.2 Hz), 7.26 (2H, t, J=7.7 Hz), 9.11 (0.5H, s), 10.5–10.9 (0.5H, br).

Reference Example 8

N-ethyl-2,3-dihydro-2,4,6,7-tetramethyl-2-[(4-phenyl-1-piperidinyl)methyl]-5-benzofuranamine To a solution of N-[2,3-dihydro-2,4,6,7-tetramethyl-2-[(4-phenyl-1-piperidinyl)methyl]benzofuran-5-yl]acetamide (0.56 g) in tetrahydrofuran (8 mL) was added 0.11 g of lithium aluminum hydride in small portions under ice-cooling. The mixture was then refluxed for 30 hours. After this reaction mixture was cooled with ice, 0.42 g Hyflo Super-Cel (tradename) and ethyl acetate were added, further followed by addition of water (0.2 mL). The mixture was stirred vigorously and, then, filtered and the filtrate was concentrated under reduced pressure. The residue was subjected to silica gel column chromatography (hexane:ethyl acetate=5:1) to provide 0.35 g of the title compound. Yield 63%.

m.p. 84–86° C.

$^1$H-NMR ($CDCl_3$) δ: 1.20 (3H, t, J=7.1 Hz), 1.46 (3H, s), 1.6–1.9 (4H, m), 2.08 (3H, s), 2.15 (3H, s), 2.18 (3H, s), 2.2–2.6 (3H, m), 2.52 (1H, d, J=14.0 Hz), 2.61 (1H, d, J=14.0 Hz), 2.75–3.1 (4H, m), 3.09 (1H, d, J=15.4 Hz), 3.15–3.3 (1H, m), 7.1–7.4 (5H, m).

Reference Example 9

N-Ethyl-2,3-dihydro-2,4,6,7-tetramethyl-2-[(4-phenyl-1-piperazinyl)methyl]-5-benzofuranamine trihydrochloride Using N-[2,3-dihydro-2,4,6,7-tetramethyl-2-[(4-phenyl-1-piperazinyl)methyl]benzofuran-5-yl]acetamide, the procedure of Reference Example 8 was otherwise repeated to provide N-ethyl-2,3-dihydro-2,4,6,7-tetramethyl-2-[(4-phenyl-1-piperazinyl)methyl]-5-benzofuranamine. This product was dissolved in methanol and an excess of 10% HCl solution in methanol was added. This mixture was concentrated under reduced pressure and the residue was crystallized from ethanol/diethyl ether to provide the title compound. Yield 64%.

m.p. 210–216° C.

$^1$H-NMR (DMSO-$d_6$) δ: 1.33 (3H, t, J=7.1 Hz), 1.64 (3H, s), 2.08 (3H, s), 2.32 (3H, s), 2.35 (3H, s), 3.0–3.9 (13H, m), 3.07 (1H, d, J=16.0 Hz), 6.86 (1H, t, J=7.2 Hz), 7.00 (2H, d, J=8.0 Hz), 7.26 (2H, t, J=7.7 Hz).

Reference Example 10

2,3-Dihydro-2,4,6,7-tetramethyl-2-[(2,3,4,5-tetrahydro-1H-3-benzazepin-3-yl)methyl]-5-benzofuranamine dihydrochloride Using 2,3,4,5-tetrahydro-1H-3-benzazepine, the procedure of Reference Example 3 was otherwise repeated to provide 2,3-dihydro-2,4,6,7-tetramethyl-2-[(3H-1,2,4,5-tetrahydro-3-benzazepin-3-yl)methyl]-5-benzofuranamine. This product was dissolved in methanol and an excess of 10% HCl solution in methanol was added. The mixture was concentrated under reduced pressure and the residure was crystallized from methanol/diethyl ether to provide the title compound.

Yield 71%.

m.p. 180–183° C.

$^1$H-NMR (DMSO-$d_6$) δ: 1.64 (3H, s), 2.09 (3H, s), 2.24 (6H, s), 3.0–3.9 (11H, m), 3.08 (1H, d, J=16.6 Hz), 7.19 (4H, s).

Reference Example 11

4-Benzyloxypiperidine hydrochloride

To a solution of tert-butyl 4-hydroxy-1-piperidinecarboxylate (5.0 g) in tetrahydrofuran (50 mL) was added sodium hydride (1.0 g, a 66% dispersion in liquid paraffin) and the mixture was stirred at room temperature for 10 minutes. Then, 3.6 mL of benzyl bromide was added and the mixture was refluxed for 1 hour. This reaction mixture was poured into aqueous ammonium chloride solution and extracted with 2 portions of ethyl acetate. The pooled organic layer was washed with water and saturated aqueous NaCl, dried over $MgSO_4$, filtered, and concentrated under reduced pressure. The residue was dissolved in 20 mL of ethyl acetate, followed by addition of 15 mL of 4 N-HCl solution in ethyl acetate, and the mixture was stirred at room temperature for 2 hours. The precipitate was collected to provide 4.4 g of the title compound.

Yield 77%.

m.p. 134–139° C.

$^1$H-NMR (CDCl$_3$) δ: 1.9–2.3 (4H, m), 3.1–3.5 (4H, m), 3.7–3.8 (1H, m), 4.52 (2H, s), 7.2–7.45 (5H, m), 9.2–9.7 (2H, br).

Reference Example 12

4-[(3-Phenyl-2-propenyl)oxy]piperidine hydrochloride

Using 3-bromo-1-phenyl-1-propene and proceeding as in Reference Example 11, the title compound was provided. Yield 42%.

m.p. 211–213° C.

$^1$H-NMR (CDCl$_3$) δ: 1.9–2.3 (4H, m), 3.1–3.5 (4H, m), 3.7–3.8 (1H, m), 4.15 (2H, dd, J=5.8, 1.3 Hz), 6.24 (1H, dt, J=16.2, 5.8 Hz), 6.60 (1H, d, J=16.2 Hz), 7.2–7.5 (5H, m), 9.2–9.8 (2H, br).

Reference Example 13

2,3-Dihydro-2,4,6,7-tetramethyl-2-[(1-piperazinyl) methyl]-5-benzofuranamine trihydrochloride A mixture of 2,3-dihydro-2,4,6,7-tetramethyl-2-[(4-benzyl-1-piperazinyl)methyl]-5-benzofuranamine (12 g, 10% palladium on carbon (1.0 g, 50% hydrous), and 150 mL ethanol was stirred in hydrogen gas at 5 atmospheric pressure and 50° C. for 15 hours. After the reaction mixture was cooled, the catalyst was filtered off and the filtrate was concentrated. The residue was recrystallized from ethyl acetate/diisopropyl ether to provide 7.1 g of the free base of the title compound. Yield 80%. This free base was treated with 4.8 N HCl solution in ethanol to give the corresponding hydrochloride, which was recrystallized from methanol/ ethyl acetate to provide the title compound.

m.p. 228–231° C.

$^1$H-NMR (DMSO-d$_6$) δ: 1.53 (3H, s), 2.05 (3H, s), 2.24 (6H, s), 2.8–4.5 (12H, m), 9.2–10.0 (3H, br s).

Reference Example 14

1-[2-(Diphenylmethoxy)ethyl]piperazine

In a reactor equipped with a water trap (Dean-Stark trap), a mixture of benzhydrol (5.0 g), 1-(2-hydroxyethyl) piperazine (3.5 g), camphor-10-sulfonic acid (14 g), and toluene (80 mL) was refluxed for 6 hours. Then, 1N-hydrochloric acid was added and the mixture was separated into two phases. The aqueous layer was made basic with 5 N aqueous sodium hydroxide, saturated with sodium chloride, and extracted with chloroform. The extract was washed with a small amount of saturated aqueous NaCl, dried over $MgSO_4$, and concentrated under reduced pressure to provide 1.9 g of the title compound. Yield 24%. This compound was not further purified but directly submitted to the next reaction.

Oil.

$^1$H-NMR (CDCl$_3$) δ: 2.42–2.54 (4H, m), 2.60 (2H, t, J=6.0 Hz), 2.89 (4H, t, J=5.0 Hz), 3.60 (2H, t, J=6.0 Hz), 5.37 (1H, s), 7.20–7.38 (10H, m).

Reference Example 15

3-(Diphenylmethoxy)propyl bromide

In a reactor fitted with a water trap, a mixture of benzhydrol (5.0 g), 3-bromo-1-propanol (3.8 g), camphor-10-sulfonic acid (1.0 g), and toluene (80 mL) was refluxed for 2 hours. This reaction mixture was concentrated and the residue was purified by silica gel column chromatography (hexane:ethyl acetate=95:5) to provide 7.0 g of the title compound. Yield 85%.

Oil.

$^1$H-NMR (CDCl$_3$) δ: 2.16 (2H, quintet, J=6.0 Hz), 3.58 (4H, t, J=6.0 Hz), 5.36 (1H, s), 7.20–7.38 (10H, m).

Reference Example 16

1-[3-(Diphenylmethoxy)propyl]piperazine

In 20 mL of ethanol was dissolved 20 g of piperazine with heating. Then, a solution of 3-(diphenylmethoxy)propyl bromide (7.0 g) in ethanol (20 mL) was added dropwise and the mixture was stirred at 70° C. for 1 hour. This reaction mixture was diluted with saturated aqueous NaCl and extracted with chloroform. The extract was washed with saturated aqueous NaCl to remove the starting material piperazine, dried over $MgSO_4$, and concentrated under reduced pressure to provide 7.1 g of the title compound. Yield 99%. This product was not further purified but directly submitted to the next reaction.

Oil.

$^1$H-NMR (CDCl$_3$) δ: 1.75–1.92 (2H, m), 2.38–2.50 (6H, m), 2.88 (4H, t, J=5.0 Hz), 3.50 (2H, t, J=6.2 Hz), 5.33 (1H, s), 7.18–7.41 (10H, m).

Reference Example 17

4-(Diphenylmethoxy)butyl chloride

Starting with benzhydrol and 4-chloro-1-butanol, the procedure of Reference Example 15 was otherwise repeated to provide the title compoun. Yield 90%.

Oil.

$^1$H-NMR (CDCl$_3$) δ: 1.52–1.84 (4H, m), 3.45 (2H, t, J=6.0 Hz), 3.53 (2H, t, J=6.6 Hz), 5.32 (1H, s), 7.15–7.44 (10H, m).

Reference Example 18

1-[4-(Diphenylmethoxy)butyl]piperazine

Using 4-(diphenylmethoxy)butyl chloride and piperazine, the procedure of Reference Example 16 was otherwise repeated to provide the title compoud.

Yield 54%.

Oil.

$^1$H-NMR (CDCl$_3$) δ: 1.36–1.52 (2H, m), 1.60–1.73 (2H, m), 2.28–2.42 (6H, m), 2.88 (4H, t, J=4.8 Hz), 3.45 (2H, t, J=6.6 Hz), 5.33 (1H, s), 7.20–7.40 (10H, m).

Reference Example 19

5-(Dipenylmethoxy)pentyl chloride

Using benzhydrol and 5-chloro-1-butanol, the procedure of Reference Example 15 was otherwise repeated to provide the title compound. Yield 96%.

Oil.

$^1$H-NMR (CDCl$_3$) δ: 1.45–1.85 (6H, m), 3.46 (2H, t, J=6.2 Hz), 3.53 (2H, t, J=6.6 Hz), 5.33 (1H, s) 7.18–7.42 (10H, m).

Reference Example 20

1-[5-(Dipenylmethoxy)pentyl]piperazine

Using 5-(dipenylmethoxy)pentyl chloride and piperazine, the procedure of Reference Example 16 was otherwise repeated to provide the title compound.

Yield 93%.

Oil.

$^1$H-NMR (CDCl$_3$) δ: 1.34–1.55 (4H, m), 1.58–1.74 (2H, m), 2.26–2.42 (6H, m), 2.89 (4H, t, J=5.0 Hz), 3.44 (2H, t, J=6.4 Hz), 5.32 (1H, s), 7.18–7.42 (10H, m).

Reference Example 21

6-(Dipenylmethoxy)hexyl chloride

Using benzhydrol and 6-chloro-1-hexanol, the procedure of Reference Example 15 was otherwise repeated to provided the title compound. Yield 88%. Oil.

$^1$H-NMR (CDCl$_3$) δ: 1.40–1.51 (4H, m), 1.60–1.85 (4H, m), 3.45 (2H, t, J=6.4 Hz), 3.52 (2H, t, J=6.8 Hz), 5.33 (1H, s), 7.20–7.36 (10H, m).

Reference Example 22

1-[6-(Dipenylmethoxy)hexyl]piperazine

Using 6-(dipenylmethoxy)hexyl chloride and piperazine, the procedure of Reference Example 16 was otherwise repeated to provide the title compound.

Yield 94%.

Oil.

$^1$H-NMR (CDCl$_3$) δ: 1.22–1.54 (6H, m), 1.58–1.71 (2H, m), 2.25–2.42 (6H, m), 2.89 (4H, t, J=4.8 Hz), 3.41–3.49 (2H, m), 5.32 (1H, s) 7.19–7.39 (10H, m).

Reference Example 23

4-[(Dipenylmethoxy)methyl]piperidine

In a reactor fitted with a water trap, a mixture of benzhydrol (3.7 g), 4-piperidinemethanol (2.3 g), camphor-10-sulfonic acid (7.0 g), and toluene (30 mL) was refluxed for 2 hours. After cooling, 35 mL of 1N-aqueous sodium hydroxide was added and the reaction mixture was extracted with ethyl acetate. The extract was washed with saturated aqueous NaCl, dried over MgSO$_4$, and concentrated under reduced pressure to provide 5.3 g of the title compound. Yield 94%. This product was not further purified but directly submitted to the next reaction.

Oil.

$^1$H-NMR (CDCl3) δ: 1.08–1.32 (2H, m), 1.72–1.88 (3H, m), 2.61 (2H, dt, J=2.2, 12.0 Hz), 3.04–3.15 (2H, m), 3.29 (2H, d, J=6.0 Hz), 5.31 (1H, s), 7.15–7.40 (10H, m).

Reference Example 24

4-[2-(Dipenylmethoxy)ethyl]piperidine

Using benzhydrol and 4-piperidineethanol, the procedure of Reference Example 23 was otherwise repeated to provide the title compound. Yield 94%.

Oil.

$^1$H-NMR (CDCl3) δ: 1.06–1.28 (2H, m), 1.54–1.71 (3H, m), 2.52–2.63 (4H, m), 3.02–3.14 (2H, m), 3.48 (2H, t, J=6.2 Hz), 5.31 (1H, s), 7.20–7.40 (10H, s).

Reference Example 25

4-[3-(Dipenylmethoxy)propyl]piperidine

Using benzhydrol and 1-(tert-butoxycarbonyl)-4-piperidinepropanol, the procedure of Reference Example 23 was otherwise repeated to provide the title compound. Yield 90%.

Oil.

$^1$H-NMR (CDCl$_3$) δ: 0.99–1.19 (2H, m), 1.21–1.38 (2H, m), 1.60–1.75 (3H, m), 1.97 (2H, s), 2.55 (2H, dt, J=2.0, 12.0 Hz), 3.03–3.10 (2H, m), 3.43 (2H, t, J=6.4 Hz), 5.33 (1H, s), 7.17–7.37 (10H, m).

Reference Example 26

1-(2-Phenylethyl)piperazine

Using β-phenethyl bromide and piperzine, the procedure of Reference Example 16 was otherwise repeated to provide the title compound. Yield 92%.

Oil.

$^1$H-NMR (CDCl$_3$) δ: 2.47–2.63 (6H, m), 2.76–2.91 (2H, m), 2.93 (4H, t, J=4.8 Hz), 7.18–7.35 (5H, m).

Reference Example 27

4-[Bis (4-fluorophenyl)methyoxy]piperidine

In a reactor fitted with a water trap, a suspension of 4-hydroxypiperidine (3.0 g), 4,4'-difluorobenzhydrol (6.2 g), and p-toluenesulfonic acid monohydrate (6.3 g) in toluene (30 mL) was refluxed for 1 hour. This reaction mixture was washed with 1N-aqueous sodium hydroxide and saturated aqueous NaCl, and dried over MgSO$_4$. After filtration, the filtrate was concentrated under reduced pressure to provide 9.8 g of a mixture containing the title compound as oil. This product was not further purified but directly submitted to the next reaction.

Reference Example 28

2,3-Dihydro-2-[[-(4-methoxybenzoyl)-1-piperazinyl]methyl]-2,4,6,7-tetramethyl-5-benzofuranamine Using 2,3-dihydro-2,4,6,7-tetramethyl-2-[(1-piperazinyl)methyl]-5-benzofuranamine and p-anisic acid, the procedure of Example 10, presented hereinafter, was otherwise followed to provide the title compound. Yield 67%.

m.p. 120–123° C. (recrystallized from ethyl acetate/diisopropyl ether).

$^1$H-NMR (CDCl3) δ:1.43 (3H, s), 2.06 (9H, s), 2.30–2.70 (6H, m), 2.82 (1H, d, J=15.6 Hz), 3.11 (1H, d, J=15.6 Hz), 3.20–3.80 (6H, m), 3.83 (3H, s), 6.90 (2H, d, J=8.8 Hz), 7.36 (2H, d, J=8.8 Hz).

Reference Example 29

2,3-Dihydro-2-[[4-(3-methoxybenzoyl)-1-piperazinyl]methyl]-2,4,6,7-tetramethyl-5-benzofuranamine Using 2,3-dihydro-2,4,6,7-tetramethyl-2-[(1-piperazinyl)methyl]-5-benzofuranamine and m-anisic acid, the procedure of Example 10, presented hereinafter, was otherwise followed to provide the title compound. Yield 73%.

m.p. 95–98° C. (recrystallized from ethyl acetate/hexane).

$^1$H-NMR (CDCl$_3$) δ: 1.43 (3H, s), 2.06 (9H, s), 2.30–2.70 (6H, m), 2.82 (1H, d, J=15.0 Hz), 3.11 (1H, d, J=15.0 Hz), 3.20–3.80 (6H, m), 3.82 (3H, s), 6.91–6.97 (3H, m), 7.28–7.40 (1H, m).

Reference Example 30

2,3-Dihydro-2-[[4-(2-methoxybenzoyl)-1-piperazinyl] methyl]-2,4,6,7-tetramethyl-5-benzofuranamine Using 2,3-dihydro-2,4,6,7-tetramethyl-2-[(1-piperazinyl) methyl]-5-benzofuranamine and o-anisic acid, the procedure of Example 10, presented hereinafter, was otherwise followed to provide the title compound. Yield 42%.

m.p. 128–131° C. (recrystallized from ethyl acetate/ hexane).

$^1$H-NMR (CDCl$_3$) δ: 1.43 (3H, s), 2.06 (9H, s), 2.30–2.70 (5H, m), 2.82 (1H, d, J=15.0 Hz), 3.00–3.80 (8H, m), 3.81 (3H, s), 6.85–7.01 (2H, m), 7.20–7.40 (2H, m).

Reference Example 31

2-[[4-(3,4-Dimethyoxybenzoyl)-1-piperazinyl]methyl]-2,3-dihydro-2,4,6,7-tetramethyl-5-benzofuranamine Using 2,3-dihydro-2,4,6,7-tetramethyl-2-[(1-piperazinyl) methyl]-5-benzofuranamine and 3,4-dimethoxybenzoic acid, the procedure of Example 10, presented hereinafter, was otherwise followed to provide the title compound. Yield 74%.

m.p. 113–116° C. (recrystallized from ethyl acetate/ diisopropyl ether).

$^1$H-NMR (CDCl$_3$) δ: 1.43 (3H, s), 2.07 (9H, s), 2.40–2.80 (6H, m), 2.83 (1H, d, J=14.8 Hz), 3.11 (1H, d, J=14.8 Hz), 3.20–3.80 (6H, m), 3.89 (3H, s), 3.90 (3H, s), 6.84 (1H, d, J=9.2 Hz), 6.90–7.00 (2H, m).

Reference Example 32

2-[[4-(4-Chlorobenzoyl)-1-piperazinyl]methyl]-2,3-dihydro-2,4,6,7-tetramethyl-5-benzofuranamine Using 2,3-dihydro-2,4,6,7-tetramethyl-2-[(1-piperazinyl) methyl]-5-benzofuranamine and 4-chlorobenzoic acid, the procedure of Example 10, presented hereinafter, was otherwise followed to provide the title compound. Yield 64%.

m.p. 136–138° C. (recrystallized from ethyl acetate/ diisopropyl ether).

$^1$H-NMR (CDCl$_3$) δ: 1.43 (3H, s), 2.06 (9H, s), 2.30–2.70 (6H, m), 2.86 (1H, d, J=14.3 Hz), 3.11 (1H, d, J=14.3 Hz), 3.30–3.80 (6H, m), 7.30–7.40 (4H, m).

Reference Example 33

2,3-Dihydro-2,4,6,7-tetramethyl-2-[[4-(4-methylbenzoyl)-1-piperazinyl]methyl]-5-benzofuranamine Using 2,3-dihydro-2,4,6,7-tetramethyl-2-[(1-piperazinyl) methyl]-5-benzofuranamine and 4-methylbenzoic acid, the procedure of Example 10, presented hereinafter, was otherwise followed to provide the title compound. Yield 53%.

m.p. 131–133° C. (recrystallized from ethyl acetate/ diisopropyl ether).

$^1$H-NMR (CDCl$_3$) δ: 1.43 (3H, s), 2.07 (9H, s), 2.38 (3H, s), 2.40–2.80 (6H, m), 2.84 (1H, d, J=14.6 Hz), 3.12 (1H, d, J=14.6 Hz), 3.20–3.90 (6H, m), 7.10–7.40 (4H, m).

Reference Example 34

2,3-Dihydro-2,4,6,7-tetramethyl-2-[[4-(4-nitrobenzoyl)-1-piperazinyl]methyl]-5-benzofuranamine Using 2,3-dihydro-2,4,6,7-tetramethyl-2-[(1-piperazinyl) methyl]-5-benzofuranamine and 4-nitrobenzoic acid, the procedure of Example 10, presented hereinafter, was otherwise followed to provide the title compound. Yield 51%.

m.p. 154–158° C. (recrystallized from ethyl acetate/ diisopropyl ether).

$^1$H-NMR (CDCl$_3$) δ: 1.43 (3H, s), 2.06 (9H, s), 2.40–2.80 (6H, m), 2.84 (1H, d, J=15.2 Hz), 3.12 (1H, d, J=15.2 Hz), 3.20–3.85 (6H, m), 7.55 (2H, d, J=8.8 Hz), 8.27 (2H, d, J=8.8 Hz).

Reference Example 35

4,4-Dipenyl-1-butanol

In 70 mL of ice-cooled diethyl ether was suspended 1.9 g of lithium aluminum hydride, followed by dropwise addition of a solution of 4,4-diphenylbutyric acid (6.0 g) in diethyl ether (50 mL). After completion of dropwise addition, the mixture was refluxed for 2 hours and, then, allowed to cool. To this reaction mixture, 1.9 mL of water, 1.9 mL of 15% aqueous sodium hydroxide, and 5.7 mL of water were added in the order mentioned and the mixture was stirred at room temperature for 30 minutes. The precipitate was filtered off and the filtrate was concentrated to provide 5.6 g of the title compound. Yield 99%.

Oil.

$^1$H-NMR (CDCl$_3$) δ: 1.20 (1H, br s), 1.40–1.70 (2H, m), 2.10–2.19 (2H, m), 3.65 (2H, t, J=6.6 Hz), 3.91 (1H, t, J=7.8 Hz), 7.10–7.40 (10H, m).

Reference Example 36

4,4-Diphenylbutyl methanesulfonate

To an iced-cooled solution of 4,4-diphenyl-1-butanol (5.6 g) in dichloroethane (100 mL), 11 mL of triethylamine and 2.9 mL of methanesulfonyl chloride were added dropwise in the order mentioned. After 30 minutes of stirring, the reaction mixture was poured into water and extracted with ethyl acetate. The extract was washed with saturated aqueous NaCl, dried over MgSO$_4$, and concentrated to provide 7.5 g of the title compound. Yield 99%.

Oil.

$^1$H-NMR (CDCl$_3$) δ: 1.73 (2H, m), 2.18 (2H, dt, J=7.9, 7.8 Hz), 2.95 (3H, s), 3.91 (1H, t, J=7.9 Hz), 4.22 (2H, t, J=6.3 Hz), 7.10–7.40 (10H, m).

Reference Example 37

5,5-Diphenylvaleronitrile

A solution of 4,4-diphenylbutyl methanesulfonate (7.5 g) and sodium cyanide (2.5 g) in dimethyl sulfoxide (70 mL) was stirred at 60° C. for 15 hours. After the reaction mixture was allowed to cool, it was extracted with diethyl ether. The extract was dried over MgSO$_4$ and concentrated, whereby 5.8 g of the title compound was obtained quantitatively.

Oil.

$^1$H-NMR (CDCl$_3$) δ: 1.50–1.72 (2H, m), 2.19 (2H, dt, J=7.9, 7.8 Hz), 2.34 (2H, t, J=7.1 Hz), 3.91 (1H, t, J=7.9 Hz), 7.10–7.40 (10H, m).

Reference Example 38

5,5-Diphenylvaleric acid

To a solution of 5,5-diphenylvaleronitrile (6.5 g) in methanol (30 mL), 80 mL of water and 10 g of sodium hydroxide were added, and the mixture was refluxed for 72 hours. After the reaction mixture was allowed to cool, it was washed with diethyl ether and adjusted to pH 1 with concentrated hydrochloric acid. This acidic solution was extracted with diethyl ether and the extract was washed with saturated aqueous NaCl, dried over MgSO$_4$, and concentrated. The residue was recrystallized to provide 5.5 g of the title compound.

Yield 86%.

m.p. 87–90° C. (recrystallized from diethyl ether)

$^1$H-NMR (DMSO-d$_6$) δ: 1.30–1.50 (2H, m), 1.95–2.09 (2H, m), 2.23 (2H, t, J=7.6 Hz), 3.92 (1H, t, J=7.6 Hz), 7.12–7.35 (10H, m).

Reference Example 39

Ethyl 4-[(Diphenylmethyl)amino]-1-piperidinecarboxylate

In a reactor fitted with a water trap, a solution of 1,1-diphenylmethylamine (5.0 g) and 1-ethoxycarbonyl-4-piperidone (4.7 g) in toluene (70 mL) was refluxed for 4 hours. This reaction mixture was concentrated under reduced pressure and he residue was dissolved in 50 mL of ethanol. After the solution was cooled with ice, 2.1 g of sodium cyanoborohydride and a small amount of bromocresol green were added. Then, 4N-HCl solution in methanol was added dropwise until the reaction mixture had turned yellow and the mixture was further stirred for 20 minutes. This reaction mixture was poured into an access of aqueous sodium hydrogen carbonate and extracted with ethyl acetate. The extract was washed with saturated aqueous NaCl, dried over MgSO$_4$, and concentrated under reduced pressure. The residue was purified by silica gel column chromatography (hexane/ethyl acetate=5:1 to 65:35) to provide 8.4 g of the title compound. Yield 91%.

Amorphous solid.

$^1$H-NMR (CDCl$_3$) δ: 1.20–1.38 (2H, m), 1.24 (3H, t, J=7.0 Hz), 1.87–1.96 (2H, m), 2.54–2.66 (1H, m), 2.70–2.84 (2H, m), 3.99–4.17 (2H, m), 4.10 (2H, q, J=7.0 Hz), 5.02 (1H, s), 7.19–7.41 (10H, m).

Reference Example 40

N-(Diphenylmethyl)-4-piperidinamine dihydrochloride

A solution of ethyl 4-[(diphenylmethyl)amino]-1-piperidinecarboxylate (42 g) and sodium hydroxide (50 g) in methanol (300 mL) was refluxed for 24 hours. This reaction mixture was diluted with water and extracted with chloroform. The extract was washed with saturated aqueous NaCl, dried over MgSO$_4$, and concentrated under reduced pressure to give N-(diphenylmethyl)-4-piperidinamine. This product was converted to the dihydrochloride using 4N-HCl solution in ethanol and the precipitate was collected by filtration and dried to provide 31 g of the title compound. Yield 73%.

m.p. 228–234° C.

$^1$H-NMR (DMSO-d$_6$) δ: 1.91–2.08 (2H, m), 2.40–2.50 (2H, m), 2.78–2.90 (2H, m), 3.07–3.41 (3H, m), 5.75 (1H, br s), 7.34–7.47 (6H, m), 7.87 (4H, d, J=6.6 Hz), 9.16 (2H, br s), 10.44 (2H, br s).

Reference Example 41

1-[(5-Amino-2,3-dihydro-2,4,6,7-tetramethylbenzofuran-2-yl)methyl]-4-piperidineethanol Using 2-bromomethyl-2,3-dihydro-2,4,6,7-tetramethyl-5-benzofuranamine and 4-piperidineethanol, the procedure of Example 1, presented hereinafter, was otherwise repeated to provide the title compound.

Yield 88%.

m.p. 94–95° C. (recrystallized from ethyl acetate/hexane).

$^1$H-NMR (CDCl$_3$) δ: 1.20–1.63 (7H, m), 1.42 (3H, s), 1.98–2.18 (2H, m), 2.07 (6H, s), 2.09 (3H, s), 2.46 (1H, d, J=13.8 Hz), 2.54 (1H, d, J=13.8 Hz), 2.76–2.88 (2H, m), 2.06–3.14 (2H, m), 3.67 (2H, t, J=6.6 Hz),

Reference Example 42

Tert-butyl [2,3-dihydro-2-[[4-(2-hydroxyethyl)-1-piperidinyl]methyl]-2,4,6,7-tetramethylbenzofuran-5-yl]carbamate To a solution of 1-[(5-amino-2,3-dihydro-2,4,6,7-tetramethylbenzofuran-2-yl)methyl]-4-piperidineethanol (3.1 g) and di-tert-butyl dicarbonate (2.1 g) in tetrahydrofuran (20 mL) was added 10 mL of 1N-aqueous sodium hydroxide and the mixture was stirred at room temperature for 2 hours. This reaction mixture was diluted with water and extracted with ethyl acetate. The extract was washed with saturated aqueous NaCl, dried over MgSO$_4$, and concentrated under reduced pressure. The residue was purified by silica gel column chromatography (ethyl acetate/methanol=95:5) to provide 3.9 g of the title compound. Yield 98%.

Oil.

$^1$H-NMR (CDCl$_3$) δ: 1.20–1.65 (7H, m), 1.41 (3H, s), 1.50 (9H, s), 2.05–2.21 (2H, m), 2.06 (3H, s), 2.10 (3H, s), 2.12 (3H, s), 2.43–2.58 (2H, m), 2.73–2.90 (2H, m), 3.01–3.13 (2H, m), 3.68 (2H, t, J=6.6 Hz), 5.78 (1H, br s).

Reference Example 43

Tert-butyl [2-[[4-formylmethyl)-1-piperidinyl]methyl]-2,3-dihydro-2,4,6,7-tetramethylbenzofuran-5-yl]carbamate Under argon gas, 2.4 mL of oxalyl chloride was added dropwise to a solution of dimethyl sulfoxide (2.6 mL) in dichloromethane (40 mL) at −78° C. and the mixture was stirred for 20 minutes. Then, a solution of tert-butyl [2,3-dihydro-2-[[4-(2-hydroxyethyl)-1-piperidinyl]methyl]-2,4,6,7-tetramethylbenzofuran-5-yl]carbamate (3.6 g) in dichloromethane (10 mL) was added dropwise and the mixture was further stirred for 1 hour. To this reaction mixture was added 8.0 mL of triethylamine. Then, at room temperature, the mixture was made basic with aqueous sodium hydrogen carbonate solution and extracted with dichloromethane. The extract was washed with saturated aqueous NaCl and dried over MgSO$_4$ and the solvent was distilled off under reduced pressure. The residue was purified by silica gel column chromatography (hexane/ethyl acetate=1:1 to ethyl acetate) to provide 3.0 g of the title compound. Yield 85%.

Oil.

$^1$H-NMR (CDCl$_3$) δ: 1.20–2.25 (7H, m), 1.41 (3H, s), 1.50 (9H, s), 2.05 (3H, s), 2.09 (2H, s), 2.12 (3H, s), 2.30–2.36 (2H, m), 2.51 (2H, s), 2.72–2.88 (2H, m), 3.02–3.13 (2H, m), 5.77 (1H, br s), 9.76 (1H, s).

Reference Example 44

Tert-butyl [2-[[4-[2-[(diphenylmethyl)amino]ethyl]-1-piperidinyl]methyl]-2,3-dihydro-2,4,6,7-tetramethylbenzofuran-5-yl]carbamate A solution of tert-butyl [2-[[4-(formylmethyl)-1-piperidinyl]methyl]-2,3-dihydro-2,4,6,7-tetramethylbenzofuran-5-yl]carbamate (1.5 g) and 1,1-diphenylmethylamine (0.60 mL) in ethanol (20 mL) was stirred on an ice bath for 30 minutes. Then, 0.26 g of sodium cyanoborohydride and a small amount of bromocresol green were added. Thereafter, 4N-HCl solution in ethanol was added until the reaction mixture had turned yellow. The mixture was stirred for 1 hour, after which it was poured in an excess of aqueous sodium hydrogen carbonate. The mixture was extracted with ethyl acetate and the extract was washed with saturated aqueous NaCl and dried over MgSO$_4$.

The solvent was then distilled off under reduced pressure and the residue was purified by silica gel column chromatography (ethyl acetate/hexane=4:1 to ethyl acetate) to provide 1.6 g of the title compound. Yield 77%.

Oil.

$^1$H-NMR (CDCl$_3$) δ: 1.20–1.78 (7H, m), 1.40 (3H, s), 1.50 (9H, s), 2.00–2.21 (2H, m), 2.04 (3H, s), 2.09 (3H, s), 2.12 (3H, s), 2.41–2.60 (4H, m), 2.72–2.84 (2H, m), 2.98–3.12 (2H, m), 4.79 (1H, s), 5.77 (1H, br s), 7.18–7.40 (10H, m).

Reference Example 45

Tert-buty [2-[[4-[2-[(3,3-diphenylpropyl)amino]ethyl]-1-piperidinyl]methyl]-2,3-dihydro-2,4,6,7-tetramethylbenzofuran-5-yl]carbamate Using tert-butyl [2-[[4-(formylmethyl)-1-piperidinyl]methyl]-2,3-dihydro-2,4,6,7-tetramethylbenzofuran-5yl] carbamate and (3,3-diphenylpropyl)amine, the procedure of Reference Example 44 was otherwise repeated to provide the title compound. Yield 97%.

Amorphous solid.

$^1$H-NMR (CDCl$_3$) δ: 1.20–1.60 (9H, m), 1.40 (3H,s), 1.50 (9H, s), 2.04 (3H, s), 2.08 (3H, s), 2.11 (3H, s), 2.23–2.70 (8H, m), 2.72–2.86 (2H, m), 2.98–3.11 (2H, m), 3.97 (1H, t, J=7.8 Hz), 5.79 (1H, br s), 7.13–7.30 (10H, m).

Reference Example 46

Ethyl 1-[(5-amino-2,4,6,7-tetramethyl-2,3-dihydrobenzofuran-2-yl)methyl]-4-piperidinecarboxylate In an autoclave, a mixture of 2-bromomethyl-2,3-dihydro-2,4,6,7-tetramethyl-5-benzofuranamine (8.4 g), ethyl isonipecotate (14 g), and xylene (20 mL) was stirred under nitrogen gas at 180° C. for 15 hours. The supernatant was taken from the reaction mixture and washed with water, saturated aqueous NaHCO$_3$, and saturated aqueous NaCl, dried over MgSO$_4$, treated with activated carbon, filtered, and concentrated under reduced pressure. The residue was purified by silica gel column chromatography (hexane/ethyl acetate=5:1 to 2:1) and crystallized from hexane to provide 2.9 g of the title compound. Yield 27%.

m.p.74–76° C.

$^1$H-NMR (CDCl$_3$) δ: 1.24 (3H, t, J=7.1 Hz), 1.41 (3H, s), 1.6–1.9 (4H, m), 1.9–2.3 ) (3H, m), 2.07 (6H, s), 2.09 (3H, s), 2.46 (1H, d, J=13.7 Hz), 2.54 (1H, d, J=13.7 Hz), 2.79 (1H, d, J=15.4 Hz), 2.8–2.95 (1H, m), 3.0–3.2 (1H, m), 3.10 (1H, d, J=15.4 Hz), 4.12 (2H, q, J=7.1 Hz).

Reference Example 47

Sodium 1-[(5-amino-2,4,6,7-tetramethyl-2,3-dihydrobenzofuran-2-yl)methyl]-4-piperidinecarboxylate To a solution of ethyl 1-[(5-amino-2,4,6,7-tetramethyl-2, 3-dihydrobenzofuran-2-yl)methyl]-4-piperidinecarboxylate (10 g) in ethanol (40 mL) was added 5.7 mL of 5N-aqueous sodium hydroxide and the mixture was stirred under nitrogen gas at room temperature for 2 hours. The precipitate was collected by filtration and washed with diethyl ether to provide 7.5 g of the title compound. Yield 75%. The filtrate was concentrated under reduced pressure and the solid residue was washed thoroughly with diethyl ether to provide an additional 1.4 g of the title compound. Yield 14%. These products were not further purified but directly submitted to the next reaction.

m.p. 237–241° C.

$^1$H-NMR (CD$_3$OD) δ: 1.35 (3H, s), 1.5–1.9 (4H, m), 1.9–2.2 (3H, m), 2.02 (3H, s), 2.05 (6H, s), 2.49 (2H, s), 2.76 (1H, d, J=15.3 Hz), 2.8–3.0 (1H, m), 3.0–3.2 (1H, m), 3.12 (1H, d, J=15.3 Hz).

Reference Example 48

1-[(5-Amino-2,3-dihydro-2,4,6,7-tetramethylbenzofuran-2-yl)methyl]-N-(diphenylmethyl)-4-piperidinecarboxamide To a suspension of sodium 1-[(5-amino-2,4,6,7-tetramethyl-2,3-dihydrobenzofuran-2-yl)methyl]-4-piperidinecarboxylate (0.89 g) in N,N-dimethylformamide (10 mL) was added 0.35 g of triethylamine hydrochloride and the mixture was stirred at room temperature for 5 minutes. To this mixture were added 0.34 g of 1-hydroxybenzotriazole and 0.46 g of 1,1-diphenylmethylamine. Then, under ice-cooling, 0.48 g of 1-ethyl-3-(3-dimethylaminopropyl)carbodiimide hydrochloride was added. This mixture was stirred under nitrogen gas at room temperature for 23 hours. This reaction mixture was diluted with water and extracted with 2 portions of ethyl acetate. The pooled organic layer was washed with water and saturated aqueous NaCl, dried over MgSO$_4$, filtered, and concentrated under reduced pressure. The residue was recrystallized from methanol/diisopropyl ether to provide 0.71 g of the title compound. Yield 57%.

m.p. 175–177° C.

$^1$H-NMR (CDCl$_3$) δ: 1.40 (3H, s), 1.4–2.3 (7H, m), 2.06 (6H, s), 2.08 (3H, s), 2.46 (1H, d, J=13.9 Hz), 2.55 (1H, d, J=13.9 Hz), 2.79 (1H, d, J=14.8 Hz), 2.9–3.4 (4H, m), 3.10 (1H, d, J=14.8 Hz), 6.01 (1H, d, J=7.9 Hz), 6.24 (1H, d, J=7.9 Hz), 7.1–7.4 (10H, m).

Reference Example 49

1-[(5-Amino-2,3-dihydro-2,4,6,7-tetramethylbenzofuran-2yl)methyl]-N-(2,2-diphenylethyl)-4-piperidinecarboxamide Using 2,2-diphenylethylamine, the procedure of Reference Example 48 was otherwise repeated to provide the title compound. Yield 62%.

m.p. 168–170° C. (recrystallized from tetrahydrofuran/methanol).

$^1$H-NMR (CDCl$_3$) δ: 1.39 (3H, s), 1.4–2.2 (7H, m), 2.06 (3H, s), 2.07 (3H, s), 2.08 (3H, s), 2.43 (1H, d, J=14.1 Hz), 2.52 (1H, d, J=14.1 Hz), 2.78 (1H, d, J=15.0 Hz), 2.8–3.5 (4H, m), 3.08 (1H, d, J=15.0 Hz), 3.88 (2H, dd, J=8.0, 5.5 Hz), 4.18 (1H, t, J=8.0 Hz), 5.38 (1H, br t, J=5.5 Hz), 7.1–7.4 (10H, m).

Reference Example 50

1-[(5-Amino-2,3-dihydro-2,4,6,7-tetramethylbenzofuran-2-yl)methyl]-N-(3,3-diphenylpropyl)-4-piperidinecarboxamide dihydrochloride Using 3,3-diphenylpropylamine, the procedure of Reference Example 48 was otherwise repeated to provide 1-[(5-amino-2,3-dihydro-2,4,6,7-tetramethylbenzofuran-2-yl) methyl]-N-(3,3-diphenylpropyl)-4-piperidinecarboxamide. This product was dissolved in methanol and a stoichiometric excess of 10% hydrogen chloride solution in methanol was added dropwise and the mixture was concentrated under reduced pressure. The residue was crystallized from ethanol/diethyl ether to provide the title compound. Yield 52%.

m.p. 166–171° C.

$^1$H-NMR (DMSO-d$_6$) δ: 1.57 (3H, s), 1.7–2.6 (7H, m), 2.05 (3H,s), 2.23 (6H, s), 2.8–3.8 (10H, s), 3.98 (1H, t, J=7.7 Hz), 7.1–7.4 (10H, m), 8.05 (1H, br s), 9.4–10. 6 (4H, m).

Reference Example 51

Ethyl 4[N-benzyl-N(3,3-diphenylpropyl)amino]-1-piperidinecarboxylate

In a reactor equipped with a water trap, a solution of 3,3-diphenylpropylamine (4.9 g) and 1-ethoxycarbonyl-4-piperidone (4.0 g) in toluene (100 mL) was refluxed for 2 hours. This reaction mixture was concentrated under reduced pressure and the residue was dissolved in 80 mL of ethanol. After this solution was cooled with ice, 1.8 g of sodium cyanoborohydride and a small amount of bromocresol green were added. Then, 4N-hydrogen chloride solution in ethanol was added dropwise until the reaction mixture had turned yellow and, after completion of dropwise addition, the mixture was further stirred for 30 minutes. This reaction mixture was poured into an excess of aqueous sodium hydrogen carbonate and extracted with ethyl acetate. The extract was washed with saturated aqueous NaCl, dried over $MgSO_4$, and concentrated under reduced pressure to give ethyl 4-[(3,3-diphenylpropyl)amino]-1-piperidinecarboxylate. This product was dissolved in 80 mL of N,N-dimethylformamide, followed by addition of 2.8 mL of benzyl bromide and 3.2 g of potassium carbonate, and the mixture was stirred at room temperature for 2 hours. This reaaction mixture was diluted with water and extracted with ethyl acetate. The extract was washed with saturated aqueous NaCl, dried over $MgSO_4$, and concentrated. The residue was purified by silica gel column chromatography (hexane/ethyl acetate=9:1 to 7:3 ) to provide 7.8 g of the title compound. Yield based on 3,3-diphenylpropylamine was 73%.

Oil.

$^1$H-NMR (CDCl$_3$) δ: 1.18–1.40 (5H, m), 1.59–1.68 (2H, m), 2.10–2.20 (2H, m), 2.49–2.62 (5H, m), 3.60 (2H, s), 3.90–4.17 (5H, m), 7.10–7.35 (15H, m).

Reference Example 52

N-Benzyl-N-(3,3-diphenylpropyl)-4-piperidinamine

Using ethyl 4-[N-benzyl-N(3,3-diphenylpropyl)amino]-1-piperidinecarboxylate, the procedure of Reference Example 40 was otherwise repeated to provide the title compound. Yield 99%.

Oil.

$^1$H-NMR (CDCl$_3$) δ: 1.22–1.43 (2H, m), 1.63–1.75 (2H, m), 2.08–2.19 (2H, m), 2.40–2.61 (5H, m), 3.02–3.08 (2H, m), 3.62 (2H, s), 3.97 (1H, t, J=7.4 Hz), 7.10–7.36 (15H, m).

Reference Example 53

N-(2-Cyanomethyl-2,3-dihydro-2,4,6,7-tetramethylbenzofuran-5-yl)formamide

A solution of N-(2-bromomethyl-2,3-dihydro-2,4,6,7-tetramethylbenzofuran-5-yl)formamide (20 g) and sodium cyanide (17 g) in dimethyl sulfoxide (100 mL) was stirred under argon gas at 100° C. for 13 hours. This reaction mixture was diluted with water and extracted with ethyl acetate. The extract was washed with water and saturated aqueous NaCl, dried over $MgSO_4$, and concentrated under reduced pressure. The residue was recrystallized from ethyl acetate/diisopropyl ether to provide 14 g of the title compound. Yield 86%.

m.p. 183–185° C.

$^1$H-NMR (CDCl$_3$) δ: 1.66 (3H, s), 2.08-2.17 (9H, m), 2.73-2.75 (2H, m), 3.03-3.22 (2H, m), 6.65-6.76 (1H, m), 7.96 (0.4H, d, J=12.2 Hz), 8.41 (0.6H, d, J=1.4 Hz).

Reference Example 54

5-Amino-2,3-dihydro-2,4,6,7-tetramethyl-2-benzofuranacetic acid

To a solution of N-(2-cyanomethyl-2,3-dihydro-2,4,6,7-tetramethylbenzofuran-5-yl)formamide (14 g) in methanol (50 mL) was added 120 mL of 4.6N-aqueous sodium hydroxide and the mixture was refluxed under argon gas for 40 hours. This reaction mixture was neutralized with concentrated hydrochloric acid and extracted with chloroform. The extract was washed with saturated aqueous NaCl, dried over $MgSO_4$, and concentrated under reduced pressure. The residue was crystallized from chloroform/diisopropyl ether to provide 11 g of the title compound. Yield 82%.

m.p. 186–188° C.

$^1$H-NMR (CDCl$_6$) δ: 1.43 (3H, s), 1.95 (9H, s), 2.60 (2H, s), 2.84 (1H, d, J=15.6 Hz), 3.18 (1H, d, J=15.6 Hz).

Reference Example 55

5-[(Tert-butoxycarbonyl)amino]-2,3-dihydro-2,4,6,7-tetramethyl-2-benzofuranacetic acid To a suspension of 5-amino-2,3-dihydro-2,4,6,7-tetramethyl- 2-benzofuranacetic acid (8.3 g) in tetrahydrofuran (50 mL) was added a solution of di-tert-butyl dicarbonate (7.6 g) in a tetrahydrofuran (5 mL) as well as 34 mL of 1N-aqueous sodium hydroxide and the mixture was stirred at room temperature for 30 minutes. After ice-cooling, the reaction mixture was made acidic with 0.5M aqueous citric acid and extracted with ethyl acetate. The extract was washed with saturated aqueous NaCl, dried over $MgSO_4$, and concentrated under reduced pressure. The residue was purified by silica gel column chromatography (hexane/ethyl acetate=2.3) to provide 11 g of the title compound. Yield 92%.

Oil.

$^1$H-NMR (CDCl$_3$) δ: 1.50-1.53 (9H, m), 1.58 (3H, s), 2.08-2.09 (6H, m), 2.13 (3H, s), 2.78 (2H, br s), 2.98 (1H, d, J=15.4 Hz), 3.25 (1H, d, J=15.4 Hz), 5.80 (1H, s).

Reference Example 56

Tert-butyl [2,3-dihydro-2-(2-hydroxyethyl)-2,4,6,7-tetramethylbenzofuran-5-yl]carbamate To a solution of 5-[(tert-butoxycarbonyl)amino]-2,3-dihydro-2,4,6,7-tetramethyl-2benzofuranacetic acid (11 g) in 50 mL tetrahydrofuran was added 64 mL of 1M borane-tetrahydrofuran complex solution in tetrahydrofuran dropwise under ice-cooling and the mixture was stirred at room temperature for 12 hours. This reaction mixture was poured into water and extracted with ethyl acetate. The extract was washed with aqueous saturated NaCl, dried over $MgSO_4$, and concentrated under reduced pressure. The residue was purified by silica gel column chromatography (hexane/ethyl acetate=2:1) to provide 7.8 g of the title compound. Yield 76%.

Oil.

$^1$H-NMR (CDCl$_3$) δ: 1.47 (3H, s), 1.50 (9H, s), 1.89-2.16 (2H, m), 2.07 (3H, s), 2.10 (3H, s), 2.13 (3H, s), 2.35 (1H, br s), 2.91 (1H, d, J=15.4 Hz), 3.06 (1H, d, J=15.6 Hz), 3.71-3.97 (2H, m), 5.79 (1H, br s).

Reference Example 57

Tert-butyl [2-(2-bromoethyl)-2,3-dihydro-2,4,6,7-tetramethylbenzofuran-5-yl]carbamate To a solution of tert-butyl [2,3-dihydro-2-(2-hydroxyethyl)-2,4,6,7-tetramethylbenzofuran-5-yl]

carbamate (7.7 g) and carbon tetrabromide (8.0 g) in tetrahydrofuran (80 mL) was added 6.3 g of triphenylphosphine under ice-cooling and the mixture was stirred for 30 minutes. This reaction mixture was filtered and the filtrate was concentrated under reduced pressure. The residue was purified by silica gel column chromatography (hexane/ethyl acetate=97:3 to 4:1) to provide 7.5 g of the title compound. Yield 82%.

Amorphous solid.

$^1$H-NMR (CDCl$_3$) δ: 1.44 (3H, s), 1.50 (9H, s), 2.07 (3H, s), 2.08 (3H, s), 2.13 (3H, s), 2.26-2.35 (2H, m), 2.88 (1H, d, J=15.8 Hz), 3.01 (1H, d, J=15.8 Hz), 3.40-3.49 (2H, m), 5.77 (1H, br s).

Reference Example 58

Tert-butyl [2-[2-[4-(diphenylmethoxy)-1-piperidinyl]ethyl]-2,3-dihydro-2,4,6,7-tetramethylbenzofuran-5-yl]carbamate A suspension of tert-butyl [2-(2-bromoethyl)-2,3-dihydro-2,4,6,7-tetramethylbenzofuran-5-yl]carbamate (1.2 g), 4-(diphenylmethoxy)piperidine (0.85 g), and potassium carbonate (0.44 g) in N,N-dimethylformamide (20 mL) was stirred at 60° C. for 15 hours. This reaction mixture was diluted with water and extracted with ethyl acetate. The extract was washed with saturated aqueous NaCl, dried over MgSO$_4$, and concentrated under reduced pressure. The residue was purified by silica gel column chromatography (ethyl acetate/methanol=98:2 to 95:5) to provide 1.6 g of the title compound. Yield 92%.

Oil.

$^1$H-NMR (CDCl$_3$) δ: 1.39 (3H, s), 1.50 (9H, s), 1.66-1.96 (6H, m), 2.03-2.20 (2H, m), 2.06 (3H, s), 2.07 (3H, s), 2.12 (3H, s), 2.40-2.48 (2H, m), 2.70-2.80 (2H, m), 2.82 (1H, d, J=15.4 Hz), 3.01 (1H, d, J=15.4 Hz), 3.35-3.50 (1H, m), 5.51 (1H, s), 5.76 (1H, br s), 7.20-7.36 (10H, m).

Reference Example 59

Tert-butyl [2-[2-[4-[(diphenylmethoxy)methyl]-1-piperidinyl]ethyl]-2,3-dihydro-2,4,6,7-tetramethylbenzofuran-5-yl]carbamate Using tert-butyl [2-(2-bromoethyl)-2,3-dihydro-2,4,6,7-tetramethylbenzofuran-5-yl]carbamate and 4-[(diphenylmethoxy)methyl]piperidine, the procedure of Reference Example 58 was otherwise repeated to provide the title compound. Yield 82%.

Oil.

$^1$H-NMR (CDCl$_3$) δ: 1.18-1.50 (2H, m), 1.40 (3H, s), 1.50 (9H, s), 1.60-1.97 (7H, m), 2.07 (6H, s), 2.12 (3H, s), 2.41-2.50 (2H, m), 2.78-3.04 (4H, m), 3.29 (2H, d, J=6.4 Hz), 5.30 (1H, s), 5.76 (1H, br s), 7.20-7.37 (10H, m).

Reference Example 60

Tert-butyl [2-[2-[4-[2-(diphenylmethoxy)ethyl]-1-piperidinyl]ethyl]-2,3-dihydro-2,4,6,7-tetramethylbenzofuran-5-yl]carbamate Using tert-butyl [2-(2-bromoethyl)-2,3-dihydro-2,4,6,7-tetramethylbenzofuran-5-yl]carbamate and 4-(2-(diphenylmethoxy)ethyl]piperidine, the procedure of Reference Example 58 was otherwise repeated to provide the title compound. Yield 83%.

Oil.

$^1$H-NMR (CDCl$_3$) δ: 1.18-1.70 (4H, m), 1.39 (3H, s), 1.49 (9H, s), 1.80-2.00 (7H, m), 2.07 (6H, s), 2.11 (3H, s), 2.35-2.50 (2H, m), 2.78-3.05 (4H, m), 3.40-3.52 (2H, m), 5.30 (1H, s), 5.77 (1H, br s), 7.19-7.38 (10H, m).

Reference Example 61

2-[(5-Amino-2,3-dihydro-2,4,6,7-tetramethylbenzofuran-2-yl)methyl]-2H-isoindole-1,3-dione A suspension of 2-bromomethyl-2,3-dihydro-2,4,6,7-tetramethyl-5-benzofuranamine (2.0 g) and potassium phthalimide (2.2 g) in N,N-dimethylacetamide (20 mL) was refluxed under nitrogen gas for 3 hours. This reaction mixture was diluted with water and extracted with 2 portions of ethyl acetate. The pooled organic layer was washed with water and saturated aqueous NaCl, dried over MgSO$_4$, filtered, and concentrated under reduced pressure. The residue was crystallized from ethyl acetate/diisopropyl ether to provide 1.4 g of the title compound. Yield 56%.

m.p. 147–150° C.

$^1$H-NMR (CDCl$_3$) δ: 1.52 (3H, s), 1.98 (3H, s), 2.03 (3H, s), 2.08 (3H, s), 2.93 (1H, d, J=15.8 Hz), 3.0-3.4 (2H, br), 3.26 (1H, d, J=15.8 Hz), 3.86 (1H, d, J=13.9 Hz), 3.95 (1H, d, J=13.9 Hz), 7.6-7.9 (4H, m).

Reference Example 62

2,3-Dihydro-2,4,6,7-tetramethyl-2-[(1,2,3,4-tetrahydroisoquinolin-2-yl)methyl]-5-benzofuranamine oxalate A suspension of 2-bromomethyl-2,3-dihydro-2,4,6,7-tetramethyl-5-benzofuranamine (1.4 g), 1,2,3,4-tetrahydroisoquinoline (1.3 g), and potassium carbonate (1.4 g) in N,N-dimethylacetamide (10 mL) was refluxed under nitrogen gas for 15 hours. This reaction mixture was diluted with water and extracted with 2 portions of ethyl acetate. The pooled organic layer was washed with water and saturated aqueous NaCl, dried over MgSO$_4$, filtered, and concentrated under reduced pressure. The residue was purified by silica gel column chromatography (hexane/ethyl acetate=3:1) to provide 2,3-dihydro-2,4,6,7-tetramethyl-2-[(1,2,3,4-tetrahydroisoquinolin-2-yl)methyl]-5-benzofuranamine. This product was dissolved in ethanol, followed by addition of 1 equivalent of oxalic acid solution in ethanol. This mixture was heated and the resulting solution was concentrated under reduced pressure. The crystals that separated out were collected to provide 1.5 g of the title compound. Yield 68%.

m.p. 153–156° C.

$^1$H-NMR (DMSO-d$_6$) δ: 1.41 (3H, s), 1.99 (6H, s), 2.02 (3H, s), 2.7-3.2 (6H, m), 2.84 (1H, d, J=15.8 Hz), 3.11 (1H, d, J=15.8 Hz), 3.89 (1H, d, J=15.4 Hz), 4.00 (1H, d, J=15.4 Hz), 6.95-7.2 (4H, m).

Reference Example 63

2-[[4-(2,3-Dihydro-2-oxo-1H-benzimidazol-1-yl)-1-piperidinyl]methyl]-2,3-dihydro-2,4,6,7-tetramethyl-5-benzofuranamine dihydrochloride In an autoclave, a suspension of 2-bromomethyl-2,3-dihydro-2,4,6,7-tetramethyl-5-benzofuranamine (1.4 g) and 4-(2-keto-1-benzimidazolinyl)piperidine (2.3 g) in xylene (20 mL) was stirred under nitrogen gas at 180° C. for 15 hours. The reaction mixture was then cooled, filtered, and washed with diethyl ether. The filtrate was washed with water and extracted with 1N-hydrochloric acid. The aqueous layer was neutralized with saturated aqueous NaHCO$_3$ and extracted with 2 portions of ethyl acetate. The pooled organic layer was washed with saturated aqueous NaCl, dried over anhydrous sodium sulfate (Na$_2$SO$_4$) and silica gel (eluted with ethyl acetate), and concentrated under reduced pressure. The residue was crystallized from ethanol to give 1.2 g of 2-[[4-(2,3-dihydro-2-oxo-1H-benzimidazol-1-yl)-1-piperidinyl]methyl]-2,3-dihydro-2,4,6,7-tetramethyl-5-benzofuranamine. Yield 55%. This product was dissolved in tetrahydrofuran with heating and after the solution was diluted with methanol, a stoichiometric excess of 10% HCl/methanol was added. The resulting solution was concentrated under reduced pressure and cyrstallized from methanol/diethyl ether to provide the title compound.

m.p. 202–208° C.

$^1$H-NMR (DMSO-d$_6$) δ: 1.5-2.3 (3H, m), 1.65 (3H, m), 2.07 (3H, s), 2.22 (3H, s), 2.25 (3H, s), 2.8-3.2 (3H, m), 3.07 (1H, d, J=16.4 Hz), 3.2-3.7 (4H, m), 3.8-4.0 (1H, m), 4.4-4.7 (1H, m), 6.9-7.1 (3H, m), 7.6-7.8 (1H, m), 9.05-10.1 (2H, br), 10.7-11.0 (1H, m).

Reference Example 64

2-[[4-[(9-Fluorenyl)oxy]-1-piperidinyl]methyl]-2,3-dihydro-2,4,6,7-tetramethyl-5-benzofuranamine oxalate Using 2-bromomethyl-2,3-dihydro-2,4,6,7-tetramethyl-5-benzofuranamine and 4-[(9-fluorenyl)oxy]piperidine, the procedure of Example 1, presented below, was followed to provide 2-[[4-[(9-fluorenyl)oxy]-1-piperidinyl]methyl]-2,3-dihydro-2,4,6,7-tetramethyl-5-benzofuranamine. Yield 63%. A portion of the product was converted to the oxalate and recrystallized from ethanol to provide the title compound.

m.p. 121–123° C.

$^1$H-NMR (DMSO-d$_6$) δ: 1.36 (3H, s), 1.63 (2H, br s), 1.86-2.06 (2H, m), 1.96 (9H, s), 2.50-3.12 (8H, m), 3.72 (1H, br s), 5.62 (1H, s), 7.27-7.45 (4H, m), 7.59 (2H, d, J=6.8 Hz), 7.79 (2H, d, J=7.4 Hz).

Reference Example 65

4-[(9-Fluorenyl)oxy]piperidine

Using 9-fluorenol and 4-piperidinol, the procedure of Reference Example 23 was otherwise repeated to provide the title compound. Yield 38%.

Amorphous solid.

$^1$H-NMR (CDCl$_3$) δ: 1.45-1.68 (2H, m), 1.75-1.90 (2H, m), 2.50-2.62 (2H, m), 3.04-3.18 (2H, m), 3.45-3.58 (1H, m), 5.62 (1H, s), 7.22-7.40 (4H, m), 7.56-7.67 (4H, m).

Reference Example 66

2-Bromo-3-(methoxymethoxy)-1,4,5-trimethylbenzene

Under nitrogen gas, a solution of 2-bromo-3,5,6-trimethylphenol (10 g) in N,N-dimethylformamide (50 mL) was added dropwise to a suspension of 60% sodium hydride (2.1 g) in N,N-dimethylformamide (20 mL) under ice-cooling and the mixture was stirred for 10 minutes. To this mixture was further added a solution of chloromethyl methyl ether (3.9 mL) in N,N-dimethylformamide (5mL) dropwise and the mixture was stirred for another 30 minutes. This reaction mixture was diluted with iced water and extracted with ethyl acetate. The extract was washed with saturated aqueous sodium chloride solution, dried over MgSO$_4$, and concentrated under reduced pressure. The residue was purified by silica gel column chromatography (hexane:ethyl acetate=97:3) to provide the title compound (12 g). Yield 99%.

Oil.

$^1$H-NMR (CDCl$_3$) δ: 2.20 (3H, s), 2.24 (3H, s), 2.34 (3H, s), 3.66 (3H, s), 5.04 (2H, s), 6.85 (1H, s).

Reference Example 67

(R)-1-[[2-(Methoxymethoxy)-3,4,6-trimethylphenyl]methyl]-1-methyloxirane

To a solution of 2-bromo-3-(methoxymethoxy)-1,4,5-trimethylbenzene (3.0 g) in tetrahydrofuran (30 mL) was added 1.6M n-butyllithium/hexane (7.0 mL) dropwise at −78° C. and the mixture was stirred for 15 minutes. To this mixture were added (R)-methylglycidyl tosylate (2.8 g) and boron trifluoride-diethyl ether (1.5 mL), and the resulting mixture was further stirred for 15 minutes. The reaction mixture was warmed up to the room temperature, then diluted with water and extracted with ethyl acetate. The extract was washed with saturated aqueous sodium chloride solution, dried over MgSO$_4$, and concentrated under reduced pressure. The residue was subjected to silica gel column chromatography (hexane:ethyl acetate=3.1) to provide (R)-2-hydroxy-3-[2-(methoxymethoxy)-3,4,6-trimethylphenyl]-2-methylpropyl 4-methylbenzene-sulfonate. This compound was dissolved in methanol (20 mL), followed by addition of potassium carbonate (1.6 g) under ice-cooling and the mixture was stirred for 30 minutes. To this reaction mixture were added ethyl acetate and water and the resulting two layers were separated. The aqueous layer was extracted with ethyl acetate and the extract was combined with the organic layer separated as above. The combined organic solution was washed with saturated aqueous sodium chloride solution, dried over MgSO$_4$, and concentrated under reduced pressure. The residue was purified by silica gel column chromatography (hexane:ethyl acetate=9:1) to provide the title compound (0.73 g). the yield based on 2-bromo-3-(methoxymethoxy)-1,4,5-trimethylbenzene=25%.

Oil.

$^1$H-NMR (CDCl$_3$) δ: 1.35 (3H, s), 2.15 (3H, s), 2.20 (3H, s), 2.26 (3H, s), 2.44 (1H, d, J=5.2 Hz), 2.50 (1H, d, J=5.2 Hz), 3.00-3.15 (2H, m), 3.61 (3H, s), 4.88-4.95 (2H, m), 6.78 (1H, s).

Reference Example 68

(S)-2,3-Dihydro-2,4,6,7-tetramethyl-2-benzofuranmethanol

To a solution of (R)-1-[[2-(methoxymethoxy)-3,4,6-trimethylphenyl]methyl]-1-methyloxirane (0.60 g) in tetrahydrofuran (5mL) was added a mixture of trifluoroacetic acid (1 mL) and water 1 mL) dropwise under ice-cooling, and the mixture was stirred for 30 minutes. This reaction mixture was diluted with water and extracted with ethyl acetate. The extract was washed with water and saturated aqueous sodium chloride solution, dried over MgSO$_4$, and concentrated under reduced pressure. The residue was purified by silica gel column chromatography (hexane:ethyl acetate=8:2) to provide the title compound as a solid (0.41 g).

Yield 83%.

$^1$H-NMR (CDCl$_3$) δ: 1.44 (3H, s), 2.08 (3H, s), 2.15 (3H, s), 2.20 (3H, s), 2.80 (1H, d, J=15.4 Hz), 3.13 (1H, d, J=15.4 Hz), 3.55-3.73 (2H, m), 6.51 (1H, s).

This product was not further purified but directly submitted to the next reaction.

Reference Example 69

(S)-(2,3-Dihydro-2,4,6,7-tetramethylbenzofuran-2-yl)methyl methanesulfonate

To a solution of (S)-2,3-dihydro-2,4,6,7-tetra-methyl-2-benzofuranmethanol (0.40 g) and triethylamine (0.41 mL) in tetrahydrofuran (5 mL) was added methane-sulfonyl chloride (0.17 mL) dropwise under ice-cooling and the mixture was stirred for 10 minutes. This reaction mixture was diluted with water and extracted with ethyl acetate. The extract was serially washed with 1N-hydrochloric acid, saturated aqueous sodium hydrogen carbonate solution, and saturated aqueous sodium chloride solution, dried over $MgSO_4$, and concentrated under reduced pressure. The residue was recrystallized from ethyl acetate-hexane to provide the title compound (0.43 g). Yield 78%.

$[\alpha]_D$+1.4° (c. 0.41, ethanol).

m.p. 70–71° C.

$^1$H-NMR (CDCl$_3$) δ: 1.52 (3H, s), 2.05 (3H, s), 2.15 ) (3H, s), 2.19 (3H, s), 2.88 (1H, d, J=15.6 Hz), 3.02 (3H, s), 3.13 (1H, d, J=15.6 Hz), 4.26 (2H, s), 6.52 (1H, s).

Reference Example 70

(S)-1-[(2,3-Dihydro-2,4,6,7-tetramethylbenzofuran-2-yl)methyl]-N-(diphenylmethyl)-4-piperidinamine A suspension of (S)-(2,3-dihydro-2,4,6,7-tetramethylbenzofuran-2-yl)methyl methanesulfonate (0.34 g), N-(diphenylmethyl)-4-piperidinamine (0.73 g), and potassium carbonate (0.38 g) in N,N-dimethylacetamide (2 mL) was stirred under argon gas at 177° C. for 6 hours. This reaction mixture was diluted with water and extracted with diisopropyl ether. The organic layer was washed with water and extracted with 1N-hydrochloric acid. The aqueous layer was made basic with 2N-sodium hydroxide/water and extracted with diisopropyl ether. The extract was washed with water and saturated aqueous sodium chloride solution, dried over $MgSO_4$, and concentrated under reduced pressure. The residue was purified by silica gel column chromatography (hexane:ethyl acetate=7:3) to provide the title compound (0.49 g). Yield 79%.

$[\alpha]_D$+3.0° (c 0.20, ethanol).

Oil.

$^1$H-NMR (CDCl$_3$) δ: 1.25–1.52 (2H, m), 1.41 (3H, s), 1.80–1.96 (2H, m), 2.00–2.23 (2H, m), 2.03 (3H, s), 2.13 (3H, s), 2.18 (3H, s), 2.31–2.56 (3H, m), 2.71–2.87 (2H, m), 2.95–3.08 (2H, m), 5.00 (1H, s), 6.46 (1H, ), 7.16–7.39 (10H, m).

Reference Example 71

1-[(2,3-Dihydro-2,4,6,7-tetramethylbenzofuran-2-yl)methyl]-N-(diphenylmethyl)-4-piperidinamine A suspension of 2-bromomethyl-2,3-dihydro-2,4,6,7-tetramethylbenzofuran (1.0 g), N-(diphenylmethyl)-4-piperidinamine (1.5 g), and potassium carbonate (0.77 g) in N,N-dimethylacetamide (4 mL) was stirred under argon gas at 177° C. for 4 hours. This reaction mixture was diluted with water and extracted with ethyl acetate. The extract was washed with water and saturated aqueous sodium chloride solution, dried over $MgSO_4$, and concentrated under reduced pressure. The residue was purified by silica gel column chromatography (hexane:ethyl acetate=7:3) to provide the title compound (1.5 g). Yield 97%.

Oil.

$^1$H-NMR (CDCl$_3$) δ: 1.25–1.50 (2H, m), 1.41 (3H, s), 1.78–1.96 (2H, m), 2.01–2.22 (2H, m), 2.03 (3H, s), 2.13 (3H, s), 2.18 (3H, s), 2.31–2.57 (3H, m), 2.71–2.86 (2H, m), 2.96–3.07 (2H, m), 5.01 (1H, s), 6.46 (1H, s), 7.16–7.39 (10H, m).

Reference Example 72

2,3-Dihydro-2,4,6,7-tetramethyl-2-[[1,2,3,6-tetrahydro-4-(3-indolyl)-1-pyridyl]methyl]-5-benzofuranamine A suspension of 2-bromomethyl-2,3-dihydro-2,4,6,7-tetramethyl-5-benzofuranamine (0.85 g), 3-(1,2,3,6-tetrahydro-4-pyridyl)-1H-indole (1.1 g) and potassium bicarbonate (0.83 g) in N,N-dimethylactamide (6 mL) was refluxed for 7.5 hours under nitrogen atmosphere. To the mixture water was added and the product was extracted twice with ethyl acetate. The combined extract was washed with water followed by saturated aqueous sodium chloride solution, dried over anhydrous magnesium sulfate, filtered and evaporated. The residue was purified by basic silica gel column chromatography (hexane:ethyl acetate=1:1) and recrystallized from acetone/diisopropyl ether to provide 0.99 g of the title compound. Yield 82%.

m.p. 169–173° C.

$^1$H-NMR(CDCl$_3$) δ: 1.49 (3H, s), 2.08 (3H, s), 2.09 (3H, s), 2.14 (3H, s), 2.50–2.65 (2H, m), 2.66 (1H, d, J=13.9 Hz), 2.75 (1H, d, J=13.9 Hz), 2.75–3.06 (3H, m), 3.21 (1H, d, J=15.4 Hz), 3.23–3.51 (2H, m), 6.15–6.24 (1H, m), 7.06–7.29 (3H, m), 7.35–7.40 (1H, m), 7.86–7.94 (1H, m), 8.08 (1H, br s).

Reference Example 73

1-Phenyl-1H-indole

A suspension of indole (8.2 g), potassium bicarbonate (12 g) and copper (I) iodide (2.7 g) in bromobenzene (70 mL) was refluxed for 3 hours under nitrogen atmosphere. To the mixture copper (I) iodide (11 g) was added and the mixture was refluxed for additional 6 hours. The insoluble material was removed by filtration and the filtrate was concentrated under reduced pressure. The residue was purified by silica gel column chromatography (hexane:ethyl acetate=50:1 to 20:1) to provide 8.4 g of the title compound. Yield 62%.

Oil.

$^1$H-NMR(CDCl$_3$) δ: 6.68 (1H, dd, J=3.2,0.8 Hz), 7.11–7.27 (2H, m), 7.29–7.43 (2H, m), 7.44–7.63 (5H, m), 7.65–7.72 (1H, m).

Reference Example 74

1-Phenyl-3-(1,2,3,6-tetrahydro-4-pyridyl)-1H-indole

To a heated (110° C.) mixture of 4-piperidone monohydrate hydrochloride (8.2 g), acetic acid (15 mL) and trifluoroacetic acid (30 mL) was added 1-phenyl-1H-indole (3.1 g) under nitrogen atmosphere over a period of 25 min. The mixture was stirred for 30 minutes at 120° C., then cooled and poured into ice. This was neutralized with conc. ammonia water under cooling and the product was extracted thrice with ethyl acetate. The combined extract was washed with water followed by saturated aqueous sodium chloride solution, dried over anhydrous magnesium sulfate, filtered and evaporated. The residue was provided for the next reaction without further purification. Yield 63%. Amorphous.

$^1$H-NMR (CDCl$_3$) δ: 2.48–2.66 (2H, m), 3.21 (2H, t, J=5.7 Hz), 3.53–3.94 (3H, m), 6.23–6.34 (1H, m), 7.00–7.70 (9H, m), 7.80–8.04 (1H, m).

Reference Example 75

Bis [2,3-Dihydro-2,4,6,7-tetramethyl-2-[[1,2,3,6-tetrahydro-4-(1-phenyl-3-indolyl)-1-pyridyl]methyl]-5-benzofuranamine] trioxalate Using 1-Phenyl-3-(1,2,3,6-tetrahydro-4-pyridyl)-1H-indole, the procedure of Reference Example 72 was otherwise repeated to provide 2,3-Dihydro-2,4,6,7-tetramethyl-2-[[1,2,3,6-tetrahydro-4-(1-phenyl-3-indolyl)-1-pyridyl]methyl]-5-benzofuranamine. Yield 61%. A part of this product was converted to oxalate to afford the title compound.

Amorphous.

$^1$H-NMR (DMSO-d$_6$) δ: 1.48 (3H, s), 1.99 (6H, s), 2.05 (3H, s), 2.64–2.90 (2H, m), 2.89 (1H, d, J=15.4 Hz), 3.05–3.48 (5H, m), 3.62–3.95 (2H, m), 6.27 (1H, br s), 7.14–7.30 (2H, m), 7.37–7.67 (6H, m), 7.79 (1H, s), 7.93–8.02 (1H, m).

Reference Example 76

2,3-Dihydro-2-[[4-(3-indolyl)-1-piperidinyl]methyl]2,4,6,7-tetramethyl-5-benzofuranamine hydrochloride A mixture of 2,3-Dihydro-2,4,6,7-tetramethyl-2-[[1,2,3,6-tetrahydro-4-(3-indolyl)-1-pyridyl]methyl]-5-benzofuranamine (0.40 g), platinum oxide (80 mg), tetrahydrofuran (2 mL and methanol (4 mL) was stirred for 2 hours at 60° C. under hydrogen atmosphere. The mixture was cooled, the catalyst was removed by filtration and the filtrate was concentrated in vacuo. The residue was dissolved in methanol and to the resulting solution excess of 10% hydrogen chloride in methanol was added. The mixture was concentrated and the resulting crystalline product was collected to afford the 0.20 g of the title compound. Yield 44%.

m.p. 236–242° C.

$^1$H-NMR (DMSO-d$_6$) δ: 1.54 (3H, br s), 1.86–2.40 (5H, m), 1.99 (3H, s), 2.01 (6H, s), 2.70–3.90 (7H, m), 2.94 (1H, d, J=16.0 Hz), 4.50–5.50 (2H, br), 6.92–7.19 (3H, m), 7.35 (1H, d, J=8.0 Hz), 7.50–7.76 (1H, m), 9.40–10.20 (1H, br), 10.89 (1H, br s).

Reference Example 77

2,3-Dihydro-2,4,6,7-tetramethyl-2-[[4-(1-phenyl-3-indolyl)-1-piperidinyl]methyl]-5-benzofuranamine oxalate A mixture of 2,3-Dihydro-2,4,6,7-tetramethyl-2-[[1,2,3,6-tetrahydro-4-(1-phenyl-3-indolyl)-1-pyridyl]methyl]-5-benzofuranamine (0.36 g), platinum oxide (72 mg), tetrahydrofuran (2 mL) and methanol (4 mL) was stirred for 3.5 hours at 60° C. under hydrogen atmosphere. The mixture was cooled, the catalyst was removed by filtration and the filtrate was concentrated in vacuo. The residue was purified by basic silica gel column chromatography (hexane:ethyl acetate=5:1) to afford 2,3-Dihydro-2,4,6,7-tetramethyl-2-[[4-(1-phenyl-3-indolyl)-1-piperidinyl]methyl]-5-benzofuranamine. This was dissolved in methanol and to the resulting solution 1 equivalent of oxalic acid solution in methanol was added. The mixture was concentrated and to the residue was added ethanol and diethyl ether. The resulting powdery product was collected to afford the 0.10 g of the title compound. Yield 24%.

Amorphous.

$^1$H-NMR(DMSO-d$_6$) δ: 1.49 (3H, s), 1.84–2.36 (5H, m), 1.97 (3H, s), 1.99 (3H, s), 2.01 (3H, s), 2.90–3.70 (6H, m), 2.91 (1H, d, J=16.0 Hz), 3.12 (1H, d, J=16.0 Hz), 7.08–7.26 (2H, m), 7.32–7.69 (6H, m), 7.48 (1H, s), 7.76 (1H, d, J=7.8 Hz).

Reference Example 78

N-[2,3-Dihydro-2-(iodomethyl)-2,4,6-trimethylbenzofuran-5-yl]formamide

To a suspension of N-[4-hydroxy-2,6-dimethyl-3-(2-methyl-2-propenyl)phenyl]formamide (16 g) and calcium carbonate (9.3 g) in tetrahydrofuran (60 mL) and methanol (60 mL) was added benzyltrimethylammonium dichloride (27 g) slowly. The mixture was stirred for 10 minutes. The insoluble material was removed by filtration and the filtrate was concentrated in vacuo. To the residue was added ethyl acetate and water. The organic layer was separated and the aqueous layer was extracted with ethyl acetate. The combined organic layer was washed with 10% aqueous sodium hydrogen sulfite, water, saturated aqueous sodium bicarbonate and aqueous sodium chloride. The organic layer was dried over magnesium sulfate, filtrated and the filtrate was concentrated in vacuo. The residue was crystallized from ethyl acetate/diisopropyl ether to afford 23 g of the title compound. Yield 93%.

m.p. 135–138° C.

$^1$H-NMR(CDCl$_3$) δ: 1.66, 1.67 (3H, s), 2.13, 2.17 (3H, s), 2.21, 2.24 (3H, s), 2.97 (1H, d, J=15.7 Hz), 3.24 (1H, d, J=15.7), 3.43, 3.44 (2H, s), 6.53, 6.54(1H, s), 6.58–6.87(1H, m), 8.00(0.45H, d, J=12.2 Hz), 8.41 (0.55H, J=1.4 Hz).

Reference Example 79

N-[2,3-Dihydro-2-(iodomethyl)-7-isopropyl-2,4,6-trimethylbenzofuran-5-yl]formamide To a mixture of N-[2,3-dihydro-2-(iodomethyl)-2,4,6-trimethylbenzofuran-5-yl]formamide (6.9 g) and 2-propanol (10 mL) was added conc. sulfuric acid (20 mL) dropwise with water-cooling. The mixture was stirred for 1.5 hours at room temperature and poured into ice. The product was extracted twice with a mixture of tetrahydrofuran and diisopropylether (1:2). The combined organic layer was washed with saturated aqueous sodium bicarbonate and saturated aqueous sodium chloride, dried over magnesium sulfate, filtrated and evaporated in vacuo. The residue was purified with silica gel column chromatography (hexane:ethyl acetate=1:1) to afford 7.3 g of the title compound.

Yield 94%.

Amorphous.

$^1$H-NMR (CDCl$_3$) δ: 1.27, 1.28 (3H, d, J=6.6 Hz), 1.30, 1.32 (3H, d, J=6.8 Hz), 1.64, 1.67 (3H, s), 2.09, 2.13 (3H, s), 2.19, 2.23 (3H, s), 2.93 (1H, d, J=15.8 Hz), 3.04–3.27 (2H, m), 3.44, 3.45 (2H, s), 6.72 (0.5H, br s), 6.81 (0.5 H), br d, J=12.2 Hz), 7.97 (0.5H, d, J=12.2 Hz), 8.41 (0.5H, d, J=1.6 Hz).

Reference Example 80

2,3-Dihydro-2-(iodomethyl)-7-isopropyl-2,4,6-trimethyl-5-benzofuranamine

To a solution of N-[2,3-dihydro-2-(iodomethyl)-7-isopropyl-2,4,6-trimethylbenzofuran-5-yl]formamide (7.3 g) in methanol (40 mL) was added conc. hydrochloric acid (10 mL). The mixture was refluxed for 1.5 hours under nitrogen atmosphere, and poured into a suspension of sodium bicarbonate (20 g) in water and ethyl acetate The organic layer was separated and the aqueous layer was extracted with ethyl acetate. The combined organic layer was washed with water and saturated aqueous sodium chloride, dried over magnesium sulfate, treated with activated carbon, filtrated and evaporated in vacuo. The residue was crystallized from hexane to afford 5.7 g of the title compound. Yield 84%.

m.p. 84–86° C.

$^1$H-NMR(CDCl$_3$) δ: 1.29 (3H, d, J=7.0 Hz), 1.31 (3H, d, J=7.0 Hz), 1.62 (3H, s), 2.06 (3H, s), 2.13 (3H, s), 2.92 (1H, d, J=15.8 Hz), 3.11–3.27 (2H, m), 3.42 (2H, s).

Reference Example 81

2,3-Dihydro-7-isopropyl-2,4,6-trimethyl-2-[(4-phenyl-1-piperidinyl)methyl]-5-benzofuranamine A suspension of 2,3-dihydro-2-(iodomethyl)-7-isopropyl-2,4,6-trimethyl-5-benzofuranamine (1.1 g), 4-phenylpiperidine (0.87 g) and potassium carbonate (0.83 g) in N,N-dimethylacetamide (6 mL) was refluxed for 4.5 hours. The mixture was diluted with water and the product was extracted twice with ethyl acetate. The combined organic layer was washed with water and saturated aqueous sodium chloride, dried over magnesium sulfate, filtrated and evaporated in vacuo. The residue was purified with basic silica gel column chromatography (hexane:ethyl acetate=30:1 to 10:1) and recrystallized from hexane/ethyl acetate to afford 0.55 g of the title compound. Yield 47%.

m.p. 128–131° C.

$^1$H-NMR (CDCl$_3$) δ: 1.27 (3H, d, J=6.8 Hz), 1.28 (3H, d, J=6.8 Hz), 1.39 (3H, s), 1.66–1.87 (4H, m), 2.07 (3H, s), 2.10–2.55 (3H, m), 2.13 (3H, s), 2.60 (2H, s), 2.72 (1H, d, J=15.0 Hz), 3.00–3.28 (4H, m), 7.12–7.37 (5H, m).

Reference Example 82

N-[2,3-Dihydro-2-(iodomethyl)-7-isopropyl-2,4,6,7-tetramethylbenzofuran-5-yl]formamide To a suspension of N-[4-hydroxy-2,3,6-trimethyl-5-(2-methyl-2-propenyl)phenyl]formamide (187 g) and calcium carbonate (104 g) in tetrahydrofuran (600 mL) and methanol (600 mL) was added benzyltrimethylammonium dichloroiodate (307 g) slowly. The mixture was stirred for 10 minutes. The insoluble material was removed by filtration and the filtrate was concentrated in vacuo. To the residue was added ethyl acetate (800 mL) and water (400 mL). The organic layer was separated and the aqueous layer was extracted with ethyl acetate (400 mL). The combined organic layer was washed with 10% aqueous solution hydrogen sulfite (400 g), water (300 mL), saturated aqueous sodium bicarbonate (300 mL) and aqueous sodium chloride (300 mL). The organic layer was dried over magnesium sulfate, treated with activated carbon, filtrated and the filtrate was concentrated in vacuo. The residue was crystallized from ethyl acetate/diisopropyl ether to afford 271 g of the title compound. Yield 94%.

m.p. 145–147° C.

$^1$H-NMR (CDCl$_3$) δ: 1.66, 1.67 (3H, s), 2.05–2.20 (9H, m), 2.98 (1H, d, J=15.9 Hz), 3.24 (1H, d, J=15.9 Hz), 3.42, 3.43 (2H, s), 6.63–8.82 (1H, m), 7.96 (0.45H, d, J=12.0 Hz), 8.41 (0.55H, d, J=1.2 Hz).

Reference Example 83

2,3-Dihydro-2-(iodomethyl)-2,4,6,7-tetramethyl-5-benzofuranamine

To a solution of N-[2,3-dihydro-2-(iodomethyl)-2,4,6,7-tetramethylbenzofuran-5-yl]formamide (6.5 g) in methanol (40 mL) was added conc. hydrochloric acid (10 mL). The mixture was refluxed for 1.5 hours under nitrogen atmosphere, and poured into a suspension of sodium bicarbonate (12 g) in water and ethyl acetate The organic layer was separated and the aqueous layer was extracted with ethyl acetate. The combined organic layer was washed with water and saturated aqueous sodium chloride, dried over magnesium sulfate, treated with activated carbon, filtrated and evaporated in vacuo. The residue was crystallized from hexane to afford 5.5 g of the title compound. Yield 91%.

m.p. 105–107° C.

$^1$H-NMR(CDCl$_3$) δ: 1.64 (3H, s), 2.07 (6H, s), 2.12 (3H, s), 2.98 (1H, d, J=15.6 Hz), 3.25 (1H, D, J=15.6 Hz), 3.41 (2H, s).

Example 1

2,3-Dihydro-2,4,6,7-tetramethyl-2-[[4-(2-phenylethyl)-1-piperidinyl]methyl]-5-benzofuranamine In an autoclave, a mixture of 2-bromomethyl-2,3-dihydro-2,4,6,7-tetramethyl-5-benzofuranamine (1.5 g), 4-(2-phenylethyl)piperidine (2.0 g), and triethylamine (5.3 g) was stirred under argon gas at 180° C. for 15 hours. After cooling, the reaction mixture was diluted with saturated aqueous NaHCO$_3$ and extracted with ethyl acetate. The extract was washed with saturated aqueous NaCl and dried over MgSO$_4$ and the solvent was distilled off under reduced pressure. The residue was purified by silica gel column chromatography (hexane/ethyl acetate=1:1) and recrystallized from diisopropyl ether to provide 0.88 g of the title compound. Yield 42%.

m.p. 91–92° C.

$^1$H-NMR (CDCl$_3$) δ: 1.17–1.35 (3H, m), 1.42 (3H, s), 1.48–1.70 (4H, m), 1.99–2.17 (2H, m), 2.07 (6H, s), 2.10 (3H, s), 2.45 (1H, d, J=13.8 Hz), 2.53 (1H, d, J=13.8 Hz), 2.55–2.65 (2H, m), 2.79 (1H, d, J=15.2 Hz), 2.82–2.92 (1H, m), 3.06–3.14 (1H, m), 3.10 (1H, d, J=15.2 Hz), 7.13–7.20 (3H, m), 7.22–7.31 (2H, m).

Example 2

2,3-Dihydro-2,4,6,7-tetramethyl-2-[[4-(3-phenylpropyl)-1-piperidinyl]methyl]-5-benzofuranamine Using 2-bromomethyl-2,3-dihydro-2,4,6,7-tetramethyl-5-benzofuranamine and 4-(3-phenylpropyl)piperidine, the procedure of Example 1 was otherwise repeated to provide the title compound.

Yield 42%.

m.p. 79–80° C. (recrystallized from diisopropyl ether/hexane).

$^1$H-NMR (CDCl$_3$) δ: 1.15–1.30 (5H, m), 1.41 (3H, s), 1.52–1.67 (4H, m), 1.98 –2.17 (2H, m), 2.06 (3H, s), 2.07 (3H, s), 2.09 (3H, s), 2.44 (1H, d, J=13.6 Hz), 2.53 (1H, d, J=13.6 Hz), 2.57 (2H, t, J=7.6 Hz), 2.78 (1H, d, J=15.0 Hz), 2.81–2.88 (1H, m), 3.00–3.10 (1H, m), 3.09 (1H, d, J=15.0 Hz), 7.13–7.21 (3H, m), 7.22–7.30 (2H, m).

Example 3

2,3-Dihydro-2,4,6,7-tetramethyl-2-[[4-(4-phenylbutyl)-1-piperidinyl]methyl]-5-benzofuranamine Using 2-bromomethyl-2,3-dihydro-2,4,6,7-tetramethyl-5-benzofuranamine and 4-(4-phenylbutyl)piperidine, the procedure of Example 1 was otherwise repeated to provide the title compound.

Yield 62%.

m.p. 70–71° C. (recrystallized from pentane).

$^1$H-NMR (CDCl$_3$) δ: 1.10–1.39 (7H, m), 1.41 (3H, s), 1.51–1.65 (4H, m), 1.98–2.18 (2H, m), 2.06 (3H, s), 2.07 (3H, s), 2.09 (3H, s), 2.44 (1H, d, J=13.8 Hz), 2.52 (1H, d, J=13.8 Hz), 2.59 (2H, t, J=7.4 Hz), 2.79 (1H, d, J=15.2 Hz), 2.83–2.88 (1H, m), 3.00–3.10 (1H, m), 3.10 (1H, d, J=15.2 Hz), 7.12–7.20 (3H, m), 7.23–7.30 (2H, m).

Example 4

2,3-Dihydro-2,4,6,7-tetramethyl-2-[[4-[(3,4-methylenedioxyphenyl)methyl]-1-piperazinyl]methyl]-5-benzofuranamine trihydrochloride In an autoclave, a mixture of 2-bromomethyl-2,3-dihydro-2,4,6,7-tetramethyl-5-benzofuranamine (1.5 g), 1-[(3,4-methylenedioxyphenyl)methyl]piperazine (2.5 g), and triethylamine (1.6 g) was stirred under argon gas at 180° C. for 15 hours. After cooling, the reaction mixture was diluted with saturated aqueous $NaHCO_3$ and extracted with ethyl acetate. The extract was washed with saturated aqueous NaCl and dried over $MgSO_4$ and the solvent was distilled off under reduced pressure. The residue was purified by silica gel column chromatography (ethyl acetate/methanol=100:0 to 95:5) and treated with 4N-HCl solution in ethanol for conversion to the trihydrochloride. This product was recrystallized from ethanol to provide 1.2 g of the title compound. Yield 41%.

m.p. 216–218° C.

$^1$H-NMR (DMSO-$d_6$) δ: 1.51 (3H, s), 2.03 (3H, s), 2.22 (3H, s), 2.23 (3H, s), 2.96 (1H, d, J=16.8 Hz), 3.25 (1H, d, J=16.8 Hz), 3.40 (10H, br s), 4.25 (2H, s), 6.06 (2H, s), 6.97 (1H, d, J=8.0 Hz), 7.08 (1H, d, J=8.0 Hz), 7.29 (1H, s), 9.85 (2H, br s).

Example 5

2-[(4-Benzyl-1-piperidinyl)methyl]-2,3-dihydro-2,4,6,7-tetramethyl-5-benzofuranamine In an autoclave, a mixture of 2-bromomethyl-2,3-dihydro-2,4,6,7-tetramethyl-5-benzofuranamine (0.85 g), 4-benzylpiperidine (1.1 g), and triethylamine (1.3 mL) was stirred under nitrogen gas at 180° C. for 15 hours. This reaction mixture was diluted with saturated aqueous $NaHCO_3$ and extracted with 2 portions of ethyl acetate. The pooled organic layer was washed with water and saturated aqueous NaCl and dried over $MgSO_4$. After filtration, the filtrate was concentrated under reduced pressure. The residue was subjected to silica gel column chromatography (hexane/ethanol=10:1) and crystallized from hexane to provide 0.86 g of the title compound. Yield 78%.

m.p. 71–73° C.

$^1$H-NMR (CDCl$_3$) δ: 1.1–1.7 (5H, m), 1.41 (3H, s), 1.9–2.2 (2H, m), 2.06 (9H, s), 2.3–2.6 (4H, m), 2.7–2.9 (1H, m), 2.79 (1H, d, J=15.4 Hz), 3.0–3.2 (1H, m), 3.10 (1H, d, J=15.4 Hz), 7.1–7.3 (5H, m).

Example 6

2-[(4-Benzyl-1-piperazinyl)methyl]-2,3-dihydro-2,4,6,7-tetramethyl-5-benzofuranamine trihydrochloride Using 1-benzylpiperazine, the procedure of Example 5 was otherwise repeated to provide 2-[(4-benzyl-1-piperazinyl)methyl]-2,3-dihydro-2,4,6,7-tetramethyl-5-benzofuranamine. This product was dissolved in methanol, followed by addition of a stoichiometric excess of 10% HCl solution in methanol and mixing. The crystals that separated out were collected to provide the title compound. Yield 78%.

m.p. 210–215° C.

$^1$H-NMR (DMSO-$d_6$) δ: 1.50 (3H, s), 2.02 (3H, s), 2.22 (3H, s), 2.23 (3H, s), 2.97 (1H, d, J=16.1 Hz), 3.0–4.2 (10H, m), 3.25 (1H, d, J=16.1 Hz), 4.35 (2H, s), 7.4–7.5 (3H, m), 7.55–7.7 (2H, m), 9.6–10.2 (2H, br).

Example 7

2-[(4-Benzyloxy-1-piperidinyl)methyl]-2,3-dihydro-2,4,6,7-tetramethyl-5-benzofuranamine In ethyl acetate was suspended 2.0 g of 4-benzyloxypiperidine hydrochloride and the suspension was neutralized with aqueous 1N-auqeous sodium hydroxide. The organic layer was separated and the aqueous layer was extracted with ethyl acetate. The pooled organic layer was washed with water and saturated aqueous NaCl, dried over $MgSO_4$, filtered, and concentrated under reduced pressure. To a solution prepared by dissolving the resulting 4-benzyloxypiperidine in 0.5 mL of toluene were added 1.1 g of 2-bromomethyl-2,3-dihydro-2,4,6,7-tetramethyl-5-benzofuranamine and 2.8 mL of triethylamine, and in an autoclave, the mixture was stirred under nitrogen gas at 180° C. for 15 hours. This reaction mixture was diluted with saturated aqueous $NaHCO_3$ and extracted with 3 portions of ethyl acetate. The pooled organic layer was washed with water and saturated aqueous NaCl, dried over $MgSO_4$, and filtered and the filtrate was concentrated under reduced pressure. The residue was subjected to silica gel column chromatography (hexane/ethyl acetate=1:1) and recrystallized from ethyl acetate/hexane to provide 1.1 g of the title compound. Yield 67%.

m.p. 85–86° C.

$^1$H-NMR (CDCl$_3$) δ: 1.42 (3H, s), 1.5–2.1 (4H, m), 2.07 (6H, s), 2.09 (3H, s), 2.1–2.45 (2H, m), 2.47 (1H, d, J=13.8 Hz), 2.56 (1H, d, J=13.8 Hz), 2.7–3.1 (2H, m), 2.80 (1H, d, J=15.4 Hz), 3.10 (1H, d, J=15.4 Hz), 3.3–3.45 (1H, m), 4.53 (2H, s), 7.2–7.4 (5H, m).

Example 8

2,3-Dihydro-2,4,6,7-tetramethyl-2-[[4-[(3-phenyl-2-propenyl)oxy]-1-piperidinyl]methyl]-5-benzofuranamine Using 4-[(3-phenyl-2-propenyl)oxy]piperidine hydrochloride, the procedure of Example 7 was otherwise repeated to provide the title compound. Yield 71%.

m.p. 77–79° C. (crystallized from diethyl ether/hexane).

$^1$H-NMR (CDCl$_3$)δ: 1.4–2.0 (4H, m), 1.42 (3H, s), 2.07 (6H, s), 2.10 (3H, s), 2.1–2.4 (2H, m), 2.48 (1H, d, J=13.8 Hz), 2.56 (1H, d, J=13.8 Hz), 2.7–3.1 (2H, m), 2.80 (1H, d, J=15.4 Hz), 3.10 (1H, d, J=15.4 Hz), 3.25–3.45 (1H, m), 4.16 (2H, dd, J=5.9, 1.1 Hz), 6.29 (1H, dt, J=15.8, 5.9 Hz), 6.60 (1H, d, J=15.8 Hz), 7.15–7.45 (5H, m).

Example 9

2,3-Dihydro-2,4,6,7-tetramethyl-2-[[4-[(3-phenylpropyl)oxy]-1-piperidinyl]methyl]-5-benzofuranamine A suspension of 2,3-dihydro-2,4,6,7-tetramethyl-2-[[4-[(3-phenyl-2-propenyl)oxy]-1-piperidinyl]methyl]-5-benzofuranamine (1.2 g) and 5% palladium on carbon (0.23 g) in tetrahydrofuran (10 mL) was stirred under hydrogen atmosphere at room temperature for 1 hour. The catalyst was then filtered off and the filtrate was concentrated under reduced pressure. The residue was crystallized from hexane to provide 0.36 g of the title compound. Yield 31%.

m.p. 53–54° C. (crystallized from hexane).

$^1$H-NMR (CDCl$_3$) δ: 1.4–1.7 (2H, m), 1.42 (3H, s), 1.7–2.0 (4H, m), 2.07 (6H, s), 2.10 (3H, s), 2.1–2.4 (2H, m), 2.47 (1H, d, J=14.0 Hz), 2.56 (1H, d, J=14.0 Hz), 2.69 (2H, t, J=7.5 Hz), 2.7–3.1 (2H, m), 2.80 (1H, d, J=15.4 Hz), 3.10 (1H, d, J=15.4 Hz), 3.1–3.3 (1H, m), 3.42 (2H, t, J=6.4 Hz), 7.1–7.35 (5H, m).

Example 10

2,3-Dihydro-2,4,6,7-tetramethyl-2-[[4-(4-phenylbutyryl)-1-piperazinyl]methyl]-5-benzofuranamine To a solution of 1-ethyl-3-(3-dimethylaminopropyl) carbodiimide hydrochloride (0.22 g) and 1-hydroxybenzotriazole (0.13 g) in N,N-dimethylformamide (5 mL) was added 0.12 g of 4-phenylbutyric acid at 0° C. and the mixture was stirred at that temperature for 5 minutes and further at room temperature for 2 hours. This reaction mixture was added to a solution of 2,3-dihydro-2,4,6,7-tetramethyl-2-[(1-piperazinyl)methyl]-5-benzofuranamine (0.20 g) in N,N-dimethylformamide (2 mL) at 0° C. and the mixture was further stirred for 30 minutes. This reaction mixture was poured into water and extracted with ethyl acetate. The extract was dried over MgSO$_4$ and the solvent was distilled off under reduced pressure. The residue was purified by silica gel column chromatography (hexane/ethyl acetate= 1:2) to provide 0.22 g of the title compound. Yield 74%.

Oil.

$^1$H-NMR (CDCl$_3$) δ: 1.42 (3H, s), 1.97 (2H, m), 2.05 (3H, s), 2.07 (6H, s), 2.30 (2H, t, J=8.0 Hz), 2.4–2.8 (10H, m), 2.80 (1H, d, J=15.1 Hz), 3.10 (1H, d, J=15.1 Hz), 3.32 (2H, t, J=4.8 Hz), 3.57 (2H, t, J=5.0 Hz), 7.1–7.3 (5H, m).

Example 11

2,3-Dihydro-2,4,6,7-tetramethyl-2-[[4-(4-phenylbutyl)-1-piperazinyl]methyl]-5-benzofuranamine trihydrochloride A mixture of 2,3-dihydro-2,4,6,7-tetramethyl-2-[[4-(4-phenylbutyryl)-1-piperazinyl]methyl]-5-benzofuranamine (0.47 g), lithium aluminum hydride (83 mg), and tetrahydrofuran (7 mL) was refluxed under argon gas for 1 hour. After cooling, the reaction mixture was poured on crushed ice and extracted with ethyl acetate. The extract was dried over MgSO$_4$ and the solvent was distilled off under reduced pressure. The residue was purified by silica gel column chromatography (ethyl acetate) and recrystallized from hexane/diisopropyl ether to provide 0.35 g of the free base of the title compound. Yield 76%. This free base was treated with 4.8N-HCl solution in ethanol for conversion to the trihydrochloride and then recrystallized from methanol/diisopropyl ether to provide 0.12 g of the title compound. Yield 21%.

m.p. 190–193° C.

$^1$H-NMR (DMSO-d$_6$) δ: 1.49 (3H, s), 1.5–1.8 (4H, m), 2.05 (3H, s), 2.22 (6H, s), 2.59 (2H, m), 2.8–3.7 (14H, m), 7.1–7.3 (5H, m), 9.7–9.9 (2H, br s).

Example 12

2,3-Dihydro-2,4,6,7-tetramethyl-2-[[4-(3-phenylpropionyl)-1-piperazinyl]methyl]-5-benzofuranamine Using 2,3-dihydro-2,4,6,7-tetramethyl-2-[(1-piperazinyl)methyl]-5-benzofuranamine and 3-phenylpropionic acid, the procedure of Example 10 was otherwise repeated to provide the title compound. Yield 73%.

Oil.

$^1$H-NMR (CDCl$_3$) δ: 1.41 (3H, s), 2.07 (9H, s), 2.4–3.1 (12H, m), 3.33 (2H, t, J=5.1 Hz), 3.58 (2H, t, J=5.1 Hz), 7.1–7.3 (5H, m).

Example 13

2,3-Dihydro-2,4,6,7-tetramethyl-2-[[4-(3-phenylpropyl)-1-piperazinyl]methyl]-5-benzofuranamine trihydrochloride Using 2,3-dihydro-2,4,6,7-tetramethyl-2-[[4-(3-phenylpropionyl)-1-piperazinyl]methyl]-5-benzofuranamine, the procedure of Example 11 was otherwise repeated to provide the title compound. Yield 19%.

m.p. 200–202° C. (recrystallized from methanol/diethyl ether).

$^1$H-NMR (DMSO-d$_6$) δ: 1.49 (3H, s), 2.03 (5H, m), 2.22 (6H, s), 2.64 (2H, t, J=7.7 Hz), 2.8–3.7 (14H, m), 7.1–7.4 (5H, m), 9.7–9.9 (2H, br s).

Example 14

2-[[4-(2,2-Diphenylethyl)-1-piperazinyl]methyl]-2,3-dihydro-2,4,6,7-tetramethyl-5-benzofuranamine Using 2-[[4-(2,2-diphenylacetyl)-1-piperazinyl]methyl]-2,3-dihydro-2,4,6,7-tetramethyl-5-benzofuranamine, the procedure of Example 11 was otherwise repeated to provide the title compound. Yield 79%.

m.p. 130–132° C. (recrystallized from ethyl acetate/diisopropyl ether).

$^1$H-NMR (CDCl$_3$) δ: 1.39 (3H, s), 2.06 (3H, s), 2.07 (6H, s), 2.10–2.70 (10H, m), 2.78 (1H, d, J=15.4 Hz), 2.96 (2H, d, J=7.4 Hz), 3.10 (1H, d, J=15.4 Hz), 4.20 (1H, t, J=7.4 Hz), 7.00–7.40 (10H, m).

Example 15

2-[[4-(3,3-Diphenylpropionyl)-1-piperazinyl]methyl]-2,3-dihydro-2,4,6,7-tetramethyl-5-benzofuranamine Using 2,3-dihydro-2,4,6,7-tetramethyl-2-[(1-piperazinyl)methyl]-5-benzofuranamine and 3,3-diphenylpropionic acid, the procedure of Example 10 was otherwise repeated to provide the title compound. Yield 72%.

m.p. 77–78° C. (recrystallized from ethyl acetate/diisopropyl ether).

$^1$H-NMR (CDCl$_3$) δ: 1.40 (3H, s), 2.07 (3H, s), 2.09 (6H, s), 2.00–2.60 (6H, m), 2.81 (1H, d, J=15.0 Hz), 3.03 (2H, d, J=7.4 Hz), 3.06 (1H, d, J=15.0 Hz), 3.31 (2H, t, J=4.6 Hz), 3.52 (2H, t, J=4.6 Hz), 4.66 (1H, t, J=7.4 Hz), 7.10–7.40 (10H, m).

Example 16

2-[[4-(3,3-Diphenylpropyl)-1-piperazinyl]methyl]-2,3-dihydro-2,4,6,7-tetramethyl-5-benzofuranamine trihydrochloride Starting with 2-[[4-(3,3-diphenylpropionyl)-1-piperazinyl]methyl]-2,3-dihydro-2,4,6,7-tetramethyl-5-benzofuranamine, the free base of the title compound was obtained in the same manner as in Example 11. Yield 78%.

Oil.

$^1$H-NMR (CDCl$_3$) δ: 1.41 (3H, s), 2.07 (6H, s), 2.09 (3H, s), 2.30–2.80 (14H, m), 2.79 (1H, d, J=15.4 Hz), 3.11 (1H, d, J=15.4 Hz), 3.97 (1H, m), 7.10–7.40 (10H, m).

The above free base was treated with 4.8N-HCl solution in ethanol and the resulting trihydrochloride was recrystallized from methanol/diisopropyl ether to provide the title compound.

m.p. 200–203° C.

Example 17

2-[[4-(Diphenylmethoxy)-1-piperidinyl]methyl]-2,3-dihydro-2,4,6,7-tetramethyl-5-benzofuranamine oxalate Using 4-(diphenylmethoxy)piperidine, the procedure of Reference Example 3 was otherwise repeated to give 2-[(4-diphenylmethoxy-1-piperidinyl)methyl]-2,3-dihydro-2,4,6,7-tetramethyl-5-benzofuranamine. This product was dissolved in ethanol, followed by addition of one equivalent of oxalic acid solution in ethanol. This mixture was heated and the resulting solution was cooled. Then, diethyl ether was added to the solution for crystallization to provide the title compound. Yield 26%.

m.p. 173–175° C.

$^1$H-NMR (DMSO-$d_6$) δ: 1.41 (3H, s), 1.6–2.1 (4H, m), 1.96 (9H, s), 2.7–3.4 (8H, m), 3.4–3.6 (1H, m), 5.64 (1H, s), 7.15–7.3 (10H, m).

Example 18

2-[[4-(2,2-Diphenylacetyl)-1-piperazinyl]methyl]-2,3-dihydro-2,4,6,7-tetramethyl-5-benzofuranamine Using 2,3-dihydro-2,4,6,7-tetramethyl-2-[(1-piperazinyl)methyl]-5-benzofuranamine and 2,2-diphenyl acetate, the procedure of Example 10 was otherwise repeated to provide the title compound. Yield 67%.

m.p. 113–115° C. (recrystallized from ethyl acetate/diisopropyl ether).

$^1$H-NMR (CDCl$_3$) δ: 1.38 (3H, s), 2.05 (3H, s), 2.06 (6H, s), 2.10–2.70 (6H, m), 2.79 (1H, d, J=15.4 Hz), 3.08 (1H, d, J=15.4 Hz), 3.00–3.80 (2H, br s), 3.39 (2H, t, J=4.8 Hz), 3.65 (2H, t, J=4.8 Hz), 5.19 (1H, s), 7.10–7.40 (10H, m).

Example 19

2-[[4-[2-(Diphenylmethoxy)ethyl]-1-piperazinyl]methyl]-2,3-dihydro-2,4,6,7-tetramethyl-5-benzofuranamine trihydrochloride Using 2-bromomethyl-2,3-dihydro-2,4,6,7-tetramethyl-5-benzofuranamine and 1-[2-(diphenylmethoxy)ethyl]piperazine, the procedure of Example 4 was otherwise repeated to provide the title compound. Yield 33%.

m.p. 173–176° C. (recrystallized from ethanol/diethyl ether).

$^1$H-NMR (DMSO-$d_6$) δ: 1.54 (3H, s), 2.03 (3H, s), 2.24 (6H, s), 2.95–3.78 (16H, m), 5.57 (1H, s), 7.25–7.44 (10H, m).

Example 20

2-[[4-[3-(Diphenylmethoxy)propyl]-1-piperazinyl]methyl]-2,3-dihydro-2,4,6,7-tetramethyl-5-benzofuranamine trihydrochloride Using 2-bromomethyl-2,3-dihydro-2,4,6,7-tetramethyl-5-benzofuranamine and 1-[3-(diphenylmethoxy)propyl]piperazine, the procedure of Example 4 was otherwise repeated to provide the title compound. Yield 54%.

m.p. 193–196° C. (recrystallized from ethanol).

$^1$H-NMR (DMSO-$d_6$) δ: 1.54 (3H, s), 2.05 (5H, br s), 2.24 (6H, s), 2.95–3.63 (16H, m), 5.48 (1H, s), 7.34–7.36 (10H, m).

Example 21

2-[[4-[4-(Diphenylmethoxy)butyl]-1-piperazinyl]methyl]-2,3-dihydro-2,4,6,7-tetramethyl-5-benzofuranamine trihydrochloride Using 2-bromomethyl-2,3-dihydro-2,4,6,7-tetramethyl-5-benzofuranamine and 1-[4-(diphenylmethoxy)butyl]piperazine, the procedure of Example 4 was otherwise repeated to provide the title compound. Yield 43%.

m.p. 203–205° C. (recrystallized from ethanol).

$^1$H-NMR (DMSO-$d_6$) δ: 1.54 (3H, s), 1.62 (2H, br s), 1.80 (2H, br s), 2.05 (3H, s), 2.23 (3H, s), 2.24 (3H, s), 2.94–3.58 (16H, m), 5.44 (1H, s), 7.20–7.38 (10H, m).

Example 22

2-[[4-[5-(Diphenylmethoxy)pentyl]-1-piperazinyl]methyl]-2,3-dihydro-2,4,6,7-tetramethyl-5-benzofuranamine trihydrochloride Using 2-bromomethyl-2,3-dihydro-2,4,6,7-tetramethyl-5-benzofuranamine and 1-[5-(diphenylmethoxy) pentyl]piperazine, the procedure of Example 4 was otherwise repeated to provide the title compound. Yield 45%.

m.p. 186–189° C. (decomp., recrystallized from ethanol).

$^1$H-NMR (DMSO-$d_6$) δ: 1.31–1.70 (6H, m), 1.53 (3H, s), 2.05 (3H, s), 2.24 (6H, s), 2.94–3.58 (16H, m), 5.42 (1H, s), 7.20–7.39 (10H, m).

Example 23

2-[[4-[6-(Diphenylmethoxy)hexyl]-1-piperazinyl]methyl]-2,3-dihydro-2,4,6,7-tetramethyl-5-benzofuranamine trihydrochloride Using 2-bromomethyl-2,3-dihydro-2,4,6,7-tetramethyl-5-benzofuranamine and 1-[6-(diphenylmethoxy)hexyl]piperazine, the procedure of Example 4 was otherwise repeated to provide the title compound. Yield 60%.

m.p. 183–186° C. (decomp., recrystallized from ethanol).

$^1$H-NMR (DMSO-$d_6$) δ: 1.35–1.71 (8H, m), 1.53 (3H, s), 2.05 (3H, s), 2.23 (6H, s), 2.96–3.60 (16H, m), 5.41 (1H, s), 7.20–7.39 (10H, m).

Example 24

2-[[4-[(Diphenylmethoxy)methyl]-1-piperidinyl]methyl]-2,3-dihydro-2,4,6,7-tetramethyl-5-benzofuranamine oxalate In an autoclave, a mixture of 2-bromomethyl-2,3-dihydro-2,4,6,7-tetramethyl-5-benzofuranamine (1.5 g), 4-[(diphenylmethoxy)methyl]piperidine (3.0 g), and triethylamine (7.4 mL) was stirred under argon gas at 180° C. for 15 hours. This reaction mixture was diluted with water and extracted with ethyl acetate. The extract was washed with saturated aqueous NaCl, dried over MgSO$_4$, and concentrated under reduced pressure. The residue was purified by silica gel column chromatography (hexane/ethyl acetate= 1:1) to provide 2.4 g of 2-[[4-[(diphenylmethoxy)methyl]-1-piperidinyl]methyl]-2,3-dihydro-2,4,6,7-tetramethyl-5-benzofuranamine. Yield 95%. This product was treated with 0.45 g of oxalic acid and, then, recrystallized from ethanol to provide 1.8 g of the title compound. Yield 58%.

m.p. 125–127° C.

$^1$H-NMR (DMSO-$d_6$) δ: 1.36–1.79 (5H, m), 1.39 (3H, s), 1.96 (9H, s), 2.60–3.34 (10H, m), 5.40 (1H, s), 7.21–7.34 (10H, m).

Example 25

2-[[4-[2-(Diphenylmethoxy)ethyl]-1-piperidinyl]methyl]-2,3-dihydro-2,4,6,7-tetramethyl-5-benzofuranamine oxalate Using 2-bromomethyl-2,3-dihydro-2,4,6,7-tetramethyl-5-benzofuranamine and 4-[2-(diphenylmethoxy)ethyl]piperidine, the procedure of Example 24 was otherwise repeated to provide the title compound. Yield 32%.

m.p. 107–110° C. (recrystallized from ethanol).

$^1$H-NMR (DMSO-$d_6$) δ: 1.36–1.72 (7H, m), 1.43 (3H, s), 1.96 (9H, s), 2.70–2.88 (3H, m), 3.00–3.25 (4H, m), 3.38–3.45 (3H, m), 5.40 (1H, s), 7.20–7.39 (10H, m).

Example 26

2-[[4-[3-(Diphenylmethoxy)propyl]-1-piperidinyl]methyl]-2,3-dihydro-2,4,6,7-tetramethyl-5-benzofuranamine oxalate Using 2-bromomethyl-2,3-dihydro-2,4,6,7-tetramethyl-5-benzofuranamine and 4-[3-(diphenylmethoxy)propyl]piperidine, the procedure of Example 24 was otherwise repeated to provide the title compound. Yield 40%.

m.p. 109–111° C. (recrystallized from ethanol).

$^1$H-NMR (DMSO-$d_6$) δ: 1.22–1.80 (9H, m), 1.40 (3H, s), 1.98 (9H, s), 2.65–3.40 (10H, m), 5.40 (1H, s), 7.20–7.38 (10H, m).

Example 27

2,3-Dihydro-2,4,6,7-tetramethyl-2-[[4-(2-phenylethyl)-1-piperazinyl]methyl]-5-benzofuranamine Using 2-bromomethyl-2,3-dihydro-2,4,6,7-tetramethyl-5-benzofuranamine and 1-(2-phenylethyl)piperazine, the procedure of Example 1 was otherwise repeated to provide the title compound.

Yield 50%.

m.p. 99–100° C. (recrystallized from diisopropyl ether/pentane).

$^1$H-NMR (CDCl$_3$) δ: 1.33 (3H, s), 1.98 (6H, s), 2.00 (3H, s), 2.38–2.75 (15H, m), 3.04 (1H, d, J=15.0 Hz), 7.08–7.19 (5H, m).

Example 28

2-[[4-[Bis(4-fluorophenyl)methoxy]-1-piperidinyl]methyl]-2,3-dihydro-2,4,6,7-tetramethyl-5-benzofuranamine oxalate A suspension of 4-[bis(4-fluorophenyl)methoxy]piperidine (3.8 g) as obtained in Reference Example 27, 2-bromomethyl-2,3-dihydro-2,4,6,7-tetramethyl-5-benzofuranamine (1.4 g), and potassium carbonate (1.4 g) in N,N-dimethylacetamide (10 mL) was refluxed under nitrogen gas for 15 hours. This reaction mixture was diluted with water and extracted with 2 portions of ethyl acetate. The pooled organic layer was washed with water and saturated aqueous NaCl, dried over MgSO$_4$, filtered, and concentrated under reduced pressure. The residue was subjected to silica gel column chromatography (hexane/ethyl acetate=2:1 to 1:1) to give 2-[[4-[bis(4-fluorophenyl)methoxy]-1-piperidinyl]methyl-2,3-dihydro-2,4,6,7-tetramethyl-5-benzofuranamine. This product was dissolved in ethanol, followed by addition of 1 equivalent of oxalic acid solution in ethanol. This mixture was heated and the resulting solution was concentrated under reduced pressure and recrystallized from methanol to provide 1.5 g of the title compound.

Yield 52%.

m.p. 181–185° C.

$^1$H NMR (DMSO-$d_6$) δ: 1.40 (3H, s), 1.6–2.1 (4H, m), 1.96 (9H, s), 2.6–3.3 (8H, m), 3.3–3.6 (1H, m), 5.68 (1H, s), 7.15 (4H, t, J=9.0 Hz), 7.39 (4H, dd, J=8.6, 5.6 Hz).

Example 29

2,3-Dihydro-2-[[4-(4-methoxybenzyl)-1-piperazinyl]methyl]-2,4,6,7-tetramethyl-5-benzofuranamine trihydrochloride Using 2,3-dihydro-2-[[4-(4-methoxybenzoyl)-1-piperazinyl]methyl]-2,4,6,7-tetramethyl-5-benzofuranamine, the procedure of Example 11 was otherwise repeated to provide the title compound.

Yield 85%.

m.p. 197–202° C. (recrystallized from water/ethanol).

$^1$H-NMR (DMSO-$d_6$) δ: 1.48 (3H, s), 2.03 (3H, s), 2.23 (6H, s), 2.70–4.40 (17H, m), 6.99 (2H, d, J=8.8 Hz), 7.53 (2H, d, J=8.8 Hz), 9.80 (2H, br s).

Example 30

2,3-Dihydro-2-[[4-(3-methoxybenzyl)-1-piperazinyl]methyl]-2,4,6,7-tetramethyl-5-benzofuranamine trihydrochloride Using 2,3-dihydro-2-[[4-(3-methoxybenzoyl)-1-piperazinyl]methyl]-2,4,6,7-tetramethyl-5-benzofuranamine, the procedure of Example 11 was otherwise repeated to provide the title compound.

Yield 74%.

m.p. 196–199° C. (recrystallized from water/ethanol).

$^1$H-NMR (DMSO-$d_6$) δ: 1.54 (3H, s), 2.04 (3H, s), 2.24 (6H, s), 2.97 (1H, d, J=16.2 Hz), 3.20–4.50 (16H, m), 7.01 (1H, d, J=8.0 Hz), 7.18 (1H, d, J=7.0 Hz), 7.30–7.46 (2H, m), 9.90 (2H, br s).

Example 31

2,3-Dihydro-2-[[4-(2-methoxybenzyl)-1-piperazinyl]methyl]-2,4,6,7-tetramethyl-5-benzofuranamine trihydrochloride Using 2,3-dihydro-2-[[4-(2-methoxybenzoyl)-1-piperazinyl]methyl]-2,4,6,7-tetramethyl-5-benzofuranamine, the procedure of Example 11 was otherwise repeated to provide the title compound.

Yield 67%.

m.p. 202–204° C. (recrystallized from methanol/ethanol).

$^1$H-NMR (DMSO-$d_6$) δ: 1.54 (3H, s), 2.03 (3H, s), 2.24 (6H, s), 2.70–3.80 (10H, m), 3.86 (3H, s), 4.10–4.70 (4H, m), 7.00–7.20 (2H, m), 7.40–7.70 (2H, m), 9.83 (2H, br s).

Example 32

2-[[4-(3,4-Dimethoxybenzyl)-1-piperazinyl]methyl]-2,3-dihydro-2,4,6,7-tetramethyl-5-benzofuranamine trihydrochloride Using 2,3-dihydro-2-[[4-(3,4-dimethoxybenzoyl)-1-piperazinyl]methyl]-2,4,6,7-tetramethyl-5-benzofuranamine, the procedure of Example 11 was otherwise repeated to provide the title compound.

Yield 77%.

m.p. 176–179° C. (recrystallized from water/ethanol).

$^1$H-NMR (DMSO-$d_6$) δ: 1.49 (3H, s), 2.03 (3H, s), 2.22 (6H, s), 2.70–4.40 (20H, m), 6.98 (1H, d, J=7.6 Hz), 7.08 (1H, d, J=7.6 Hz), 7.39 (1H, s), 9.80 (2H, br s).

Example 33

2-[[4-(4-Chlorobenzyl)-1-piperazinyl]methyl]-2,3-dihydro-2,4,6,7-tetramethyl-5-benzofuranamine trihydrochloride Using 2-[[4-(4-chlorobenzoyl)-1-piperazinyl]methyl]-2,3-dihydro-2,4,6,7-tetramethyl-5-benzofuranamine, the procedure of Example 11 was otherwise repeated to provide the title compound.

Yield 91%.

m.p. 198–200° C. (recrystallized from water/ethanol).

$^1$H-NMR (DMSO-d$_6$) δ: 1.43 (3H, s), 2.02 (3H, s), 2.20 (3H, s), 2.22 (3H, s), 2.70–4.40 (14H, m), 7.54 (2H, d, J=7.6 Hz), 7.63 (2H, d, J=7.6 Hz), 9.75 (2H, br s).

Example 34

2,3-Dihydro-2,4,6,7-tetramethyl-2-[[4-(4-methylbenzyl)-1-piperazinyl]methyl]-5-benzofuranamine trihydrochloride Using 2,3-dihydro-2,4,6,7-tetramethyl-2-[[4-(4-methylbenzoyl)-1-piperazinyl]methyl]-5-benzofuranamine, the procedure of Example 11 was otherwise repeated to provide the title compound. Yield 36%.

m.p. 183–186° C. (recrystallized from water/ethanol).

$^1$H-NMR (DMSO-d$_6$) δ: 1.50 (3H, s), 2.00 (3H, s), 2.20 (6H, s), 2.34 (3H, s), 2.80–4.20 (12H, m), 4.28 (2H, s), 7.25 (2H, d, J=7.6 Hz), 7.49 (2H, d, J=7.6 Hz), 9.78 (2H, br s).

Example 35

2-[[4-(4,4-Diphenylbutyryl)-1-piperazinyl]methyl]-2,3-dihydro-2,4,6,7-tetramethyl-5-benzofuranamine Using 2,3-dihydro-2,4,6,7-tetramethyl-2-[(1-piperazinyl)methyl]-5-benzofuranamine and 4,4-diphenylbutyric acid, the procedure of Example 10 was otherwise repeated to provide the title compound.

Yield 29%.

m.p. 135–138° C. (recrystallized from ethyl acetate/diisopropyl ether).

$^1$H-NMR (CDCl$_3$) δ: 1.41 (3H, s), 2.07 (9H, s), 2.10–2.70 (10H, m), 2.80 (1H, d, J=14.7 Hz), 3.09 (1H, d, J=14.7 Hz), 3.10–3.40 (4H, m), 3.55 (2H, t, J=5.2 Hz), 3.95 (1H, t, J=7.7 Hz), 7.10–7.70 (10H, m).

Example 36

2-[[4-(4,4-Diphenylbutyl)-1-piperazinyl]methyl]-2,3-dihydro-2,4,6,7-tetramethyl-5-benzofuranamine trihydrochloride Using 2-[[4-(4,4-diphenylbutyryl)-1-piperazinyl]methyl]-2,3-dihydro-2,4,6,7-tetramethyl-5-benzofuranamine, the procedure of Example 11 was otherwise repeated to provide the title compound.

Yield 54%.

m.p. 190–192° C. (recrystallized from methanol/diethyl ether).

$^1$H-NMR (DMSO-d$_6$) δ: 1.50 (3H, s), 1.55–1.65 (2H, m), 2.03 (5H, br s), 2.23 (6H, s), 2.60–4.30 (15H, m), 7.10–7.40 (10H, m), 9.70–10.00 (2H, br s).

Example 37

2-[[4-(5,5-Diphenylvaleryl)-1-piperazinyl]methyl]-2,3-dihydro-2,4,6,7-tetramethyl-5-benzofuranamine Using 2,3-dihydro-2,4,6,7-tetramethyl-2-[(1-piperazinyl)methyl]-5-benzofuranamine and 5,5-diphenylvaleric acid, the procedure of Example 10 was otherwise repeated to provide the title compound.

Yield 86%.

Oil.

$^1$H-NMR (CDCl$_3$) δ: 1.41 (3H, s), 1.50–1.70 (2H, m), 2.20–2.70 (21H, m), 2.81 (1H, d, J=15.4 Hz), 3.09 (1H, d, J=15.4 Hz), 3.28 (2H, t, J=4.8 Hz), 3.53 (2H, t, J=4.8 Hz), 3.90 (1H, t, J=8.2 Hz), 7.20–7.40 (10H, m).

Example 38

2-[[4-(5,5-Diphenylpentyl)-1-piperazinyl]methyl]-2,3-dihydro-2,4,6,7-tetramethyl-5-benzofuranamine trihydrochloride Using 2-[[4-(5,5-diphenylvaleryl)-1-piperazinyl]methyl]-2,3-dihydro-2,4,6,7-tetramethyl-5-benzofuranamine, the procedure of Example 11 was otherwise repeated to provide the title compound.

Yield 86%.

m.p. 177–181° C. (recrystallized from methanol/diethyl ether).

$^1$H-NMR (DMSO-d$_6$) δ: 1.05–1.25 (2H, m), 1.44 (3H, s), 1.60–1.80 (2H, m), 1.90–2.10 (5H, m), 2.21 (6H, s), 2.40–4.00 (15H, m), 7.10–7.40 (10H, m), 9.75 (2H, br s).

Example 39

1-[(5-Amino-2,3-dihydro-2,4,6-tetramethylbenzofuran-2-yl)methyl]-N-(diphenylmethyl)-4-piperidinamine Using 2-bromomethyl-2,3,-dihydro-2,4,6,7-tetramethyl-5-benzofuranamine and N-(diphenylmethyl)-4-piperidinamine, the procedure of Example 1 was otherwise repeated to provide the title compound.

Yield 38%.

m.p. 128–129° C. (recrystallized from ethyl acetate/hexane).

$^1$H-NMR (CDCl$_3$) δ: 1.25–1.49 (2H, m), 1.39 (3H, s), 1.79–1.92 (2H, m), 2.00–2.19 (2H, m), 2.05 (3H, s), 2.06 (3H, s), 2.08 (3H, s), 2.30–2.54 (3H, m), 2.73–2.84 (2H, m), 2.96–3.11 (2H, m), 5.00 (1H, s), 7.17–7.39 (10H, m).

Example 40

1-[(5-Amino-2,3-dihydro-2,4,6,7-tetramethylbenzofuran-2-yl)methyl]-N-(diphenylmethyl)-4-piperidinamine trihydrochloride 1-[(5-Amino-2,3-dihydro-2,4,6,7-tetramethylbenzofuran-2-yl)methyl]-N-(diphenylmethyl)-4-piperidineamine (2.2 g) was treated with 4N-HCl solution in ethanol and the resulting trihydrochloride was recrystallized from ethanol/diethyl ether to provide 2.5 g of the title compound. Yield 87%.

m.p. 200–203° C. (decomp.).

$^1$H-NMR (DMSO-d$_6$) δ: 1.57 (3H, s), 2.04 (3H, s), 2.18–2.59 (4H, m), 2.23 (6H, s), 2.98–3.76 (9H, m), 5.74 (1H, s), 7.30–7.44 (6H, m), 7.86–7.90 (4H, m).

Example 41

1[(5-Amino-2,3-dihydro-2,4,6,7-tetramethylbenzofuran-2-yl)methyl]-N-(diphenylmethyl)-4-piperidineethylamine trihydrochloride To a solution of tert-butyl [2-[[4-[2-[(diphenylmethyl)amino]ethyl]-1-piperidinyl]methyl]-2,3-dihydro-2,4,6,7-tetramethylbenzofuran-5-yl]carbamate (1.6 g) in ethanol (3 mL) was added 10 mL of 4N-HCl/ethanol and the mixture was stirred at room temperature for 15 hours. This reaction mixture was made basic with aqueous sodium hydrogen carbonate solution and extracted with ethyl acetate. The extract was washed with saturated aqueous NaCl and dried over MgSO$_4$. The solvent was then distilled off under reduced pressure to provide 1.3 g of 1-[(5-amino-2,3-dihydro-2,4,6,7-tetramethylbenzofuran-2-yl)methyl]-N-(diphenylmethyl)-4-piperidineethylamine. Yield 97%. This product was treated with 4N-HCl solution in ethanol and the resulting trihydrochloride was recrystallized from ethanol/diethyl ether to provide 1.3 g of the title compound. Yield 76%.

m.p. 197–199° C. (decomp.).

$^1$H-NMR (DMSO-d$_6$) δ: 1.50–1.80 (7H, m), 1.57 (3H, s), 2.04 (3H, s), 2.24 (6H, s), 2.80–3.75 (10H, m), 5.60 (1H, br s), 7.38–7.58 (6H, m), 7.78 (4H, d, J=7.8 Hz).

Example 42

1-[(5-Amino-2,3-dihydro-2,4,6,7-tetramethylbenzofuran-2-yl)methyl]-N-(3,3-diphenylpropyl)-4-piperidineethylamine trihydrochloride Using tert-butyl [2-[[4-[2-[(3,3-diphenylpropyl)amino]ethyl]-1-piperidinyl]methyl]-2,3-dihydro-2,4,6,7-tetramethylbenzofuran-5-yl]carbamate, the procedure of Example 41 was otherwise repeated to provide the title compound. Yield 23%.

m.p. 180–181° C. (recrystallized from ethanol/diethyl ether).

$^1$H-NMR (DMSO-d$_6$) δ: 1.58 (3H, s), 1.77 (9H, br s), 2.05 (3H, s), 2.23 (6H, s), 2.73–3.69 (12H, m), 4.10–4.14 (1H, m), 7.18–7.32 (10H, m).

Example 43

1-[(5-Amino-2,3-dihydro-2,4,6,7-tetramethylbenzofuran-2-yl)methyl]-N-(diphenylmethyl)-4-piperidinemethylamine dihydrochloride To a solution of 1-[(5-amino-2,3-dihydro-2,4,6,7-tetramethylbenzofuran-2-yl)methyl]-N-(diphenylmethyl)-4-piperidinecarboxamide (1.3 g) in tetrahydrofuran (20 mL) was added 17 mL of 1 M borane tetrahydrofuran complex solution in tetrahydrofuran with ice-cooling and the mixture was refluxed under nitrogen gas for 23 hours. After this reaction mixture was cooled with ice, 12 mL of 5N-hydrochloric acid was added dropwise and the mixture was concentrated under reduced pressure. The residue was neutralized with sodium hydrogen carbonate and extracted with 2 portions of ethyl acetate. The pooled organic layer was washed with water and saturated aqueous NaCl, dried over MgSO$_4$, filtered, and concentrated under reduced pressure. The residue was subjected to silica gel column chromatography (hexane/ethanol=10:1) to give 0.89 g of 1-[(5-amino-2,3-dihydro-2,4,6,7-tetramethylbenzofuran-2-yl)methyl]-N-(diphenylmethyl)-4-piperidinemethylamine. Yield 68%. This product was dissolved in methanol and a stoichiometric excess of 10% HCl solution in methanol was added dropwise. The mixture was concentrated under reduced pressure to provide the title compound.

Amorphous solid.

$^1$H-NMR (DMSO-d$_6$) δ: 1.3–2.2 (5H, m), 1.48 (3H, s), 1.98 (3H, s), 2.00 (6H, s), 2.3–3.7 (10H, m), 4.0–4.3 (1H, br), 5.48 (1H, br s), 7.2–7.6 (6H, m), 7.6–7.9 (4H, m).

Example 44

1-[(5-Amino-2,3-dihydro-2,4,6,7-tetramethylbenzofuran-2-yl)methyl]-N-(2,2-diphenylethyl)-4-piperidinemethylamine trihydrochloride To a solution of 1-[(5-amino-2,3-dihydro-2,4,6,7-tetramethylbenzofuran-2-yl)methyl]-N-(2,2-diphenylethyl)-4-piperidinecarboxamide (1.0 g) in tetrahydrofuran (20 mL) was added 12 mL of 1 M borane tetrahydrofuran complex solution in tetrahydrofuran dropwise with ice-cooling and the mixture was refluxed under nitrogen gas for 6 hours. After this reaction mixture was cooled with ice, 8 mL of 5N-hydrochloric acid was added dropwise, followed by stirring. The mixture was added dropwise to a suspension of sodium hydrogen carbonate (4 g) in water/diisopropyl ether for neutralization and extracted with 2 portions of ethyl acetate. The pooled organic layer was washed with saturated aqueous NaCl, dried over MgSO$_4$, filtered, and concentrated. After the residue was dissolved in methanol, 10 mL of 5N-hydrochloric acid was added and the mixture was refluxed for 1 hour. After ice-cooling, the mixture was diluted with 20 mL of 5N-aqueous sodium hydroxide and extracted with 3 portions of diethyl ether. The pooled organic layer was washed with water and saturated aqueous NaCl, dried over MgSO$_4$, filtered, and concentrated under reduced pressure. The residue was subjected to silica gel column chromatography (hexane/ethyl acetate/triethylamine=30:10:1 to 20:10:1) to recover 1-[(5-amino-2,3-dihydro-2,4,6,7-tetramethylbenzofuran-2-yl)methyl]-N-(2,2-diphenylethyl)-4-piperidinemethylamine. After this product was dissolved in methanol, a stoichiometric excess of 10% HCl solution in methanol was added dropwise and the resulting mixture was concentrated under reduced pressure to provide 0.74 g of the title compound.

Yield 61%.

Amorphous solid.

$^1$H-NMR (DMSO-d$_6$) δ: 1.4–2.3 (5H, m), 1.57 (3H, s), 2.04 (3H, s), 2.23 (6H, s), 2.6–3.8 (12H, m), 4.6–4.8 (1H, m), 7.1–7.5 (10H, m), 8.9–9.2 (2H, br), 9.5–10.1 (3H, br), 10.3–10.6 (1H, br).

Example 45

1-[(5-Amino-2,3-dihydro-2,4,6,7-tetramethylbenzofuran-2-yl)methyl]-N-(3,3-diphenylpropyl)-4-piperidinemethylamine dihydrochloride Using 1-[(5-amino-2,3-dihydro-2,4,6,7-tetramethylbenzofuran-2-yl)methyl]-N-(3,3-diphenylpropyl)-4-piperidinecarboxamide (the free base obtained in Reference Example 50), the procedure of Example 44 was otherwise repeated to provide the title compound. Yield 46%.

m.p. 168–172° C. (crystallized from methanol/diethyl ether).

$^1$H-NMR (DMSO-d$_6$) δ: 1.3–2.2 (5H, m), 1.46 (3H, br s), 1.98 (9H, s), 2.3–3.5 (14H, m), 4.09 (1H, t, J=7.5 Hz), 7.1–7.4 (10H, m).

Example 46

1-[(5-Amino-2,3-dihydro-2,4,6,7-tetramethylbenzofuran-2-yl)methyl]-N-benzyl-N-(3,3-diphenylpropyl)-4-piperidinamine trihydrochloride Using 2-bromoethyl-2,3-dihydro-2,4,6,7-tetramethyl-5-benzofuranamine and N-benzyl-N-(3,3-diphenylpropyl)-4-piperidinamine, the procedure of Example 1 was otherwise repeated to provide 1-[(5-amino-2,3-dihydro-2,4,6,7-tetramethylbenzofuran-2-yl)methyl]-N-benzyl-N-(3,3-diphenylpropyl)-4-piperidinamine. Yield 60%.

Oil.

$^1$H-NMR (CDCl$_3$) δ: 1.39 (3H, s), 1.45–1.61 (4H, m), 1.97–2.18 (4H, m), 2.05 (3H, s), 2.07 (3H, s), 2.08 (3H, s), 2.37–2.54 (5H, m), 2.72–2.89 (2H, m), 3.02–3.10 (2H, m), 3.58 (2H, s), 3.94 (1H, t, J=7.6 Hz), 7.11–7.30 (15H, m).

The 1-[(5-amino-2,3-dihydro-2,4,6,7-tetramethylbenzofuran-2-yl)methyl]-N-benzyl-N-(3,3-diphenylpropyl)-4-piperidinamine obtained above (1.0 g) was treated with 4N HCl solution in ethanol and the resulting trihydrochloride was recrystallized from ethanol/diethyl ether to provide 0.65 g of the title compound. Yield 53%.

m.p. 185–187° C.

$^1$H-NMR (DMSO-d$_6$) δ: 1.59 (3H, s), 1.93–2.55 (6H, m), 2.06 (3H, s), 2.24 (6H, s), 2.76–3.60 (9H, m), 3.79–3.94 (3H, m), 4.23–4.49 (2H, m), 7.16–7.23 (10H, m), 7.38–7.42 (3H, m), 7.66–7.71 (2H, m).

Example 47

1-[(5-Amino-2,3-dihydro-2,4,6,7-tetramethylbenzofuran-2-yl)methyl]-N-(3,3-diphenylpropyl)-4-piperidinamine trihydrochloride To a solution of 1-[(5-amino-2,3dihydro-2,4,6,7-tetramethylbenzofuran-2-yl)methyl]-N-benzyl-N-(3,3-diphenylpropyl)-4-piperidinamine (1.5 g) in ethanol (50 mL) was added 0.30 g of 5% palladium on carbon (50% hydrous) and the mixture was stirred in a hydrogen atmosphere at 5 atmospheric pressure and 40° C. for 6 hours. This reaction mixture was filtered and the filtrate was concentrated under reduced pressure to provide 1.2 g of 1-[(5-amino-2,3-dihydro-2,4,6,7-tetramethylbenzofuran-2-yl)methyl]-N-(3,3-diphenylpropyl)-4-piperidinamine. Yield 94%. This product was treated with 4N-HCl solution in ethanol and the resulting trihydrochloride was recrystallized from ethanol/diethyl ether to provide 1.3 g of the title compound. Yield 82%.

m.p. 187–189° C. (decomp.).

$^1$H-NMR (DMSO-d$_6$) δ: 1.58 (3H, s), 2.02–2.26 (4H, m), 2.05 (3H, s), 2.23 (6H, s), 2.78 (2H, br s), 3.00–3.55 (10H, m), 3.77–3.91 (1H, m), 4.14 (1H, t, J=7.6 Hz), 7.20–7.33 (10H, m).

Example 48

2-[2-[4-(Diphenylmethoxy)-1-piperidinyl]ethyl]-2,3-dihydro-2,4,6,7-tetramethyl-5-benzofuranamine oxalate Starting with tert-butyl [2-[2-[4-(diphenylmethoxy)-1-piperidinyl]ethyl]-2,3-dihydro-2,4,6,7-tetramethylbenzofuran-5-yl]carbamate, the procedure of Example 41 was otherwise repeated to provide 2-[2-[4-diphenylmethoxy)-1-piperidinyl]ethyl]-2,3-dihydro-2,4,6,7-tetramethyl-5-benzofuranamine. Yield 84%. This compound was converted to the oxalate and recrystallized from ethanol to provide the title compound. Yield 45%.

m.p. 137–139° C.

$^1$H-NMR (DMSO-d$_6$) δ; 1.31 (3H, s), 1.62–2.01 (6H, m), 1.94 (6H, s), 1.96 (3H, s), 2.77–3.20 (8H, m), 3.54 (1H, br s), 5.65 (1H, s), 7.20–7.38 (10H, m).

Example 49

2-[2-[4-[(Diphenylmethoxy)methyl]-1-piperidinyl]ethyl]-2,3-dihydro-2,4,6,7-tetramethyl-5-benzofuranamine dioxalate Using tert-butyl [2-[2-[4-[(diphenylmethoxy)methyl]-1-piperidinyl]ethyl]-2,3-dihydro-2,4,6,7-tetramethylbenzofuran-5-yl]carbamate, the procedure of Example 48 was otherwise repeated to provide the title compound. Yield 20%.

m.p. 160–162° C. (recrystallized from ethanol).

$^1$H-NMR (DMSO-d$_6$) δ: 1.28–1.66 (2H, m), 1.36 (3H, s), 1.84–2.10 (5H, m), 1.99 (9H, s), 2.81–3.16 (6H, m), 3.25–3.30 (2H, m), 3.41–3.56 (2H, m), 5.43 (1H, s), 7.20–7.37 (10H, m).

Example 50

2-[2-[4-[2-(Diphenylmethoxy)ethyl]-1-piperidinyl]ethyl]-2,3-dihydro-2,4,6,7-tetramethyl-5-benzofuranamine oxalate Using tert-butyl [2-[2-[4-[2-(diphenylmethoxy)ethyl]-1-piperidinyl]ethyl]-2,3-dihydro-2,4,6,7-tetramethylbenzofuran-5-yl]carbamate, the procedure of Example 48 was otherwise repeated to provide the title compound. Yield 54%.

m.p. 119–121° C. (recrystallized from ethanol).

$^1$H-NMR (DMSO-d$_6$) δ: 1.24–2.10 (9H, m), (3H, s), 1.96 (6H, s), 1.98 (3H, s), 2.79–3.14 (6H, m), 3.36–3.43 (4H, m), 5.41 (1H, s) 7.20–7.38 (10H,

Example 51

N-[2-[[4-[4-Diphenylmethoxy)butyl]-1-piperazinyl]methyl]-2,3-dihydro-2,4,6,7-tetramethylbenzofuran-5-yl]acetamide To a suspension of 2-[[4-[4-(diphenylmethoxy)butyl]-1-piperazinyl]methyl]-2,3-dihydro-2,4,6,7-tetramethyl-5-benzofuranamine trihydrochloride (0.60 g) in tetrahydrofuran (10 mL) was added 8 mL of 1N-aqueous sodium hydroxide as well as 0.10 mL of acetic anhydride under ice-cooling and the mixture was stirred for 1 hour. This reaction mixture was diluted with water and extracted with ethyl acetate. The extract was washed with saturated aqueous NaCl, dried over MgSO$_4$, and concentrated under reduced pressure. The residue was purified by silica gel column chromatography (ethyl acetate/methanol=9:1) to provide 0.48 g of the title compound. Yield 93%.

Oil.

$^1$H-NMR (CDCl$_3$) δ: 1.42 (3H, s), 1.62 (4H, br s), 2.05–2.82 (25H, m), 3.08–3.17 (1H, m), 3.41–3.47 (2H, m), 5.32 (1H, s), 6.58–6.62 (1H, m), 7.20–7.33 (10H, m).

Example 52

2-[[4-[4-(Diphenylmethoxy)butyl]-1-piperazinyl]methyl]-N-ethyl-2,3-dihydro-2,4,6,7-tetramethyl-5-benzofuranamine trihydrochloride To a solution of N-[2-[[4-[4-(diphenylmethoxy)butyl]-1-piperazinyl]methyl]-2,3-dihydro-2,4,6,7-tetramethylbenzofuran-5yl]acetamide (0.48 g) in tetrahydrofuran (20 mL) was added 64 mg of lithium aluminum hydride and the mixture was refluxed under argon gas for 15 hours. this reaction mixture was diluted with a small amount of water and ethyl acetate, MgSO$_4$ and Hyflo Super-Cel (tradename) were added. The mixture was filtered and the filtrate was concentrated under reduced pressure. The residue was purified by silica gel column chromatography (ethyl acetate/methanol=95:5) to give 0.32 g of 2-[[(4-[4-(diphenylmethoxy)butyl]-1-piperazinyl]methyl]-N-ethyl-2,3-dihydro-2,4,6,7-tetramethyl-5benzofuranamine. Yield 68%. this product was treated with 4N-HCl solution in ethanol and the resulting trihydrochloride was recrystallized from ethanol/diethyl ether to provide 0.32 g of the title compound. Yield 55% m.p. 156–158° C.

$^1$H-NMR (DMSO-d$_6$) δ; 1.33 (3H, t, J=7.2 Hz), 1.57–1.63 (5H, m), 1.73–1.85 (2H, m), 2.05 (3H, s), 2.30 (3H, s), 2.33 (3H, s), 2.98–3.60 (18H, m), 5.44 (1H, s), 7.22–7.40 (10H, m).

Example 53

1-[(5-Amino-2,3-dihydro-2,4,6,7-tetramethylbenzofuran-2-yl)-methyl]-N-[bis(4-fluorophenyl)methyl]-4-piperidinamine Under argon gas, a suspension of 2-bromomethyl-2,3-dihydro-2,4,6,7-tetramethyl-5-benzofuranamine (1.4 g), N-[bis(4-fluorophenyl)methyl]-4-piperidinamine (4.5 g), and potassium carbonate (1.4 g) in N,N-dimethylacetamide (20 mL) was stirred at 172° C. for 4.5 hours. This reaction mixture was diluted with water and extracted with ethyl acetate. The extract was washed with water and saturated aqueous sodium chloride solution, dried over $MgSO_4$, and concentrated under reduced pressure. The residue was purified by column chromatograph (silica gel/ethyl acetate and basic silica gel/hexane:ethyl acetate=9:1–85:15) and recrystallized from ethyl acetate-hexane to provide the title compound (0.97 g, yield 39%).

m.p. 133–134° C.

$^1$H-NMR (CDCl$_3$) δ: 1.24–1.47 (2H, m), 1.40 (3H, s), 1.78–1.91 (2H, m), 1.96–2.18 (2H, m), 2.05 (3H, s), 2.07 (3H, s), 2.08 (3H, s), 2.23–2.55 (3H, m), 2,74–2.96 (2H, m), 2.95–3.12 (2H, m), 4.97 (1H, s), 6.97 (4H, t, J=8.8 Hz), 7.20–7.40 (4H, m).

Example 54

1-[(5-Amino-2,3-dihydro-2,4,6,7-tetramethylbenzofuran-2-yl)methyl]-N-[bis(4-methoxyphenyl)methyl]-4-piperidinamine Starting with 2-bromomethyl-2,3-dihydro-2,4,6,7-tetramethyl-5-benzofuranamine and N-[bis(4-methoxyphenyl)methyl]-4-piperidinamine, the procedure of Example 53 was otherwise repeated to provide the title compound. Yield 43%.

m.p. 109–111° C.

$^1$H-NMR (CDCl$_3$) δ: 1.25–1.46 (2H, m), 1.40 (3H, s), 1.76–2.55 (9H, m), 2.05 (3H, s), 2.07 (3H, s), 2.08 (3H, s), 2.72–2.86 (2H, m), 2.06–3.12 (2H, m), 3.77 (6H, s), 4.92 (1H, s), 6.82 (4H, d, J=8.8 Hz), 7.26 (4H, d, J=8.8 Hz).

Example 55

(R)-1-[(5-Amino-2,3-dihydro-2,4,6,7-tetramethylbenzofuran-2-yl)methyl]-N-(diphenylmethyl)-4-piperidinamine 1-[(5-Amino-2,3-dihydro-2,4,6,7-tetramethylbenzofuran-2-yl)methyl]-N-(diphenylmethyl)-4-piperidinamine was subjected to preparative high-performance liquid chromatography (column: CHIRALCEL OD (20×250 mm, Daicel Chemical Industry, Ltd.), mobile phase: hexane-2-propanol=95:5); flow rate: 80 mL/min., column temperature: 30° C.) to provide the title compound. $[α]_D$ −21.4° (c 0.496, ethanol)

Example 56

(S)-1-[(5-Amino-2,3-dihydro-2,4,6,7-tetramethylbenzofuran-2-yl)methyl]-N-(diphenylmethyl)-4-piperidinamine 1-[(5-Amino-2,3-dihydro-2,4,6,7-tetramethylbenzofuran-2-yl)methyl]-N-(diphenylmethyl)-4-piperidinamine was subjected to preparative high-performance liquid chromatography (column: CHIRALCEL OD (20×250 mm, Daicel Chemical Industry, Ltd.), mobile phase: hexane-2-propanol=95:5); flow rate: 80 mL/min., column temperature: 30° C.) to provide the title compound.

$[α]_D$ +21.5° (c 0.549, ethanol)

Example 57

(R)-1-[(5-Amino-2,3-dihydro-2,4,6,7-tetramethylbenzofuran-2yl)methyl]-N-(diphenylmethyl)-4-piperidinamine sulfate To a solution of (R)-1-[(5-amino-2,3-dihydro-2,4,6,7-tetramethylbenzofuran-2-yl)methyl]-N-(diphenyl-methyl)-4-piperidinamine (3.5 g) in a mixture of methanol (15 mL) and ethyl acetate (5 mL) was added 2N-sulfuric acid (7.5 mL) and the mixture was concentrated under reduced pressure. To the residue was added methanol (15 mL) and the mixture was stood for 18 hours. The solid formed were collected, dried and recrystallized from methanol-water to provide 3.5 g of the title compound. Yield 75%.

$[α]_D$ −8.0° (c 0.51, ethanol).

m.p. 154–156° C.

$^1$H-NMR (DMSO-d$_6$) δ: 1.33 (3H, s), 1.52–2.20 (4H, m), 1.95 (9H, s), 2.15–2.30 (1H, s), 2.58–2.82 (4H, m), 2.97–3.25 (4H, m), 5.52 (1H,br s), 7.28–7.42 (6H, m), 7.52–7.58 (4H, m).

Example 58

(S)-1-[(5-Amino-2,3-dihydro-2,4,6,7-tetramethylbenzofuran-2-yl)methyl]-N-(diphenylmethyl)-4-piperidinamine sulfate Using (S)-1-[(5-amino-2,3-dihydro-2,4,6,7-tetramethylbenzofuran-2-yl)methyl]-N-(diphenylmethyl)-4-piperidinamine and 2N-sulfuric acid, the procedure of Example 57 was otherwise repeated to provide the title compound. Yield 68%

$[α]_D$ +8.5° (c 0.52, ethanol).

m.p. 155–157° C. (recrystallized from methanol-water)

$^1$-NMR (DMSO-d$_6$) δ: 1.34 (3H, s), 1.53–2.07 (4H, m), 1.95 (9H, s), 2.23 (1H, br s), 2.59–2.81 (4H, m), 2.99–3.28 (4H, m), 5.52 (1H, br s), 7.28–7.43 (6H, m), 7.52–7.57 (4H, m).

Example 59

(S)-1-[(5-Amino-2,3-dihydro-2,4,6,7-tetramethylbenzofuran-2-yl)methyl]-N-(diphenylmethyl)-4-piperidinamine 4-Nitroaniline (0.14 g) was dissolved in 2N-hydrochloric acid (3 mL) under heating and the solution was ice-cooled. To this solution was added a solution of sodium nitrite (72 mg) in water (0.5 mL) dropwise, and the mixture was stirred for 15 minutes. The aqueous solution of 4-nitrobenzenediazonium chloride thus obtained was added to a solution of (S)-1-[(2,3-dihydro-2,4,6,7-tetramethylbenzofuran-2yl)methyl]-N-(diphenylmethyl)-4-piperidinamine (0.43 g) in acetic acid (3 mL) under cooling and the mixture was stirred at room temperature for 12 hours. This reaction mixture was poured into saturated aqueous sodium carbonate solution and extracted with ethyl acetate. The extract was washed with water and saturated aqueous sodium chloride solution, dried over $MgSO_4$, and concentrated under reduced pressure. To the (S)-1-[[2,3-dihydro-2,4,6,7-tetramethyl-5-(4-nitrophenyl-azo)benzofuran-2-yl]methyl]-N-(diphenylmethyl)-4-piperidinamine thus obtained were added ethanol (30 mL) and Raney nickel (Kawaken Fine Chemical NDHT-90) (0.6 g) and the mixture was stirred in a hydrogen atmosphere at 5 atm. and room temperature for 1 hour. This reaction mixture was filtered and the filtrate was concentrated under reduced pressure. The residue was purified by silica gel column chromatography (hexane:ethyl acetate=1:1) to provide 0.32 g of the title compound. Yield 71%.

¹H-NMR (CDCl₃) δ: 1.25–1.52 (2H, m), 1.40 (3H, s), 1.78–2.20 (4H, m), 2.05 (3H, s), 2.06 (3H, s), 2.08 (3H, s), 2.30–2.54 (3H, m), 2.72–2.83 (2H, m), 2.95–3.11 (2H, m), 5.01 (1H, s), 7.15–7.40 (10H, m).

Example 60

1-[(5-Amino-2,3-dihydro-7-isopropyl-2,4,6-trimethylbenzofuran-2-yl)methyl]-N-(diphenylmethyl)-4-piperidinamine A suspension of 2,3-dihydro-2-(iodomethyl)-7-isopropyl-2,4,6-trimethyl-5-benzofuranamine (1.1 g), N-(diphenylmethyl)-4-piperidinamine (1.4 g) and potassium carbonate (0.83 g) in N,N-dimethylacetamide (6 mL) was refluxed for 4.5 hours. The mixture was diluted with water and the product was extracted twice with ethyl acetate. The combined organic layer was washed with water and saturated aqueous sodium chloride, dried over magnesium sulfate, filtrated and evaporated in vacuo. The residue was purified with basic silica gel column chromatography (hexane:ethyl acetate=20:1 to 5:1) and recrystallized from hexane/ethyl acetate to afford 1.4 g of the title compound. Yield 91%.

Amorphous.

¹H-NMR(CDCl₃) δ: 1.20–1.50 (2H, m), 1.25 (3H, d, J=7.4 Hz), 1.26 (3H, d, J=6.8 Hz), 1.33 (3H, s), 1.70–2.55 (5H, m), 2.04 (3H, s), 2.12 (3H, s), 2.51 (2H, s), 2.67 (1H, d, J=15.0 Hz), 2.78–3.29 (3H, m), 3.12 (1H, d, J=15.0 Hz), 5.01(1H, s), 7.12–7.47 (10H, m).

The chemical formulas of the compounds obtained in Examples 1 through 60 are shown in Table 1 through Table 5.

TABLE 1

| Ex. No. | Y | Za | Zb | Ar | Additive |
|---|---|---|---|---|---|
| 1 | CH | CH₂ | CH₂ | phenyl | |
| 2 | CH | CH₂ | CH₂CH₂ | phenyl | |
| 3 | CH | CH₂ | CH₂CH₂CH₂ | phenyl | |
| 4 | N | CH₂ | — | benzodioxole | 3HCl |
| 5 | CH | CH₂ | — | phenyl | |
| 6 | N | CH₂ | — | phenyl | 3HCl |
| 7 | CH | OCH₂ | — | phenyl | |
| 8 | CH | OCH₂ | CH=CH | phenyl | |

TABLE 1-continued

[Structure: 5-amino-4,6,7-trimethyl-2-methyl-2,3-dihydrobenzofuran with CH₂ linked to N of piperazine/piperidine ring, then —Y—Za—Zb—Ar]

| Ex. No. | Y | Za | Zb | Ar | Additive |
|---|---|---|---|---|---|
| 9 | CH | OCH$_2$ | CH$_2$CH$_2$ | phenyl | |
| 10 | N | COCH$_2$ | CH$_2$CH$_2$ | phenyl | |
| 11 | N | CH$_2$ | CH$_2$CH$_2$CH$_2$ | phenyl | 3HCl |
| 12 | N | COCH$_2$ | CH$_2$ | phenyl | |
| 13 | N | CH$_2$ | CH$_2$CH$_2$ | phenyl | 3HCl |
| 14 | N | CH$_2$ | CH(phenyl) | phenyl | |
| 15 | N | COCH$_2$ | CH(phenyl) | phenyl | |
| 16 | N | CH$_2$ | CH$_2$·CH(phenyl) | phenyl | 3HCl |
| 17 | CH | O·CH(phenyl) | — | phenyl | (COOH)$_2$ |

TABLE 1-continued
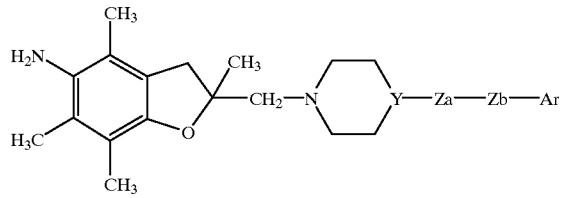
| Ex. No. | Y | Za | Zb | Ar | Additive |
|---|---|---|---|---|---|
| 18 | N | CO·CH (phenyl) | — | (phenyl) | |
TABLE 2
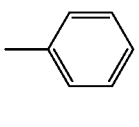
| Ex. No. | Y | Za | Zb | Ar | Additive |
|---|---|---|---|---|---|
| 19 | N | CH$_2$ | CH$_2$OCH (phenyl) | (phenyl) | 3HCl |
| 20 | N | CH$_2$ | CH$_2$CH$_2$OCH (phenyl) | (phenyl) | 3HCl |
| 21 | N | CH$_2$ | CH$_2$CH$_2$CH$_2$OCH (phenyl) | (phenyl) | 3HCl |
| 22 | N | CH$_2$ | CH$_2$CH$_2$CH$_2$CH$_2$OCH (phenyl) | (phenyl) | 3HCl |
| 23 | N | CH$_2$ | CH$_2$CH$_2$CH$_2$CH$_2$CH$_2$OCH (phenyl) | (phenyl) | 3HCl |

TABLE 2-continued
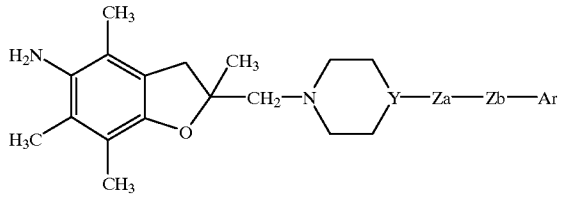
| Ex. No. | Y | Za | Zb | Ar | Additive |
|---|---|---|---|---|---|
| 24 | CH | CH$_2$ | 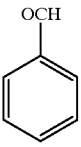 | 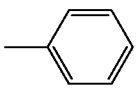 | (COOH)$_2$ |
| 25 | CH | CH$_2$ | 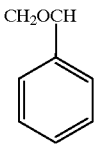 | 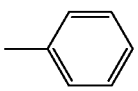 | (COOH)$_2$ |
| 26 | CH | CH$_2$ | 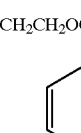 | 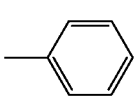 | (COOH)$_2$ |
| 27 | N | CH$_2$ | CH$_2$ | 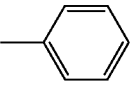 | |
| 28 | CH | 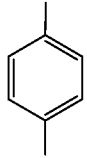 | — | 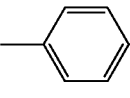 | (COOH)$_2$ |
TABLE 3
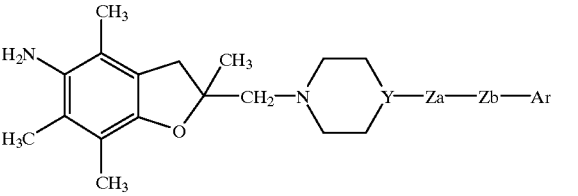
| Ex. No. | Y | Za | Zb | Ar | Additive |
|---|---|---|---|---|---|
| 29 | N | CH$_2$ | — | 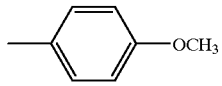 | 3HCl |

TABLE 3-continued
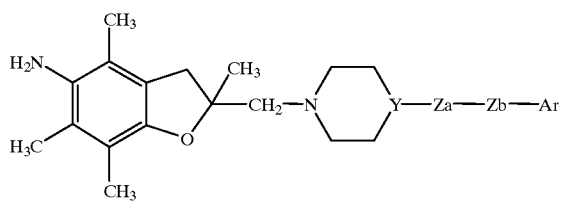
| Ex. No. | Y | Za | Zb | Ar | Additive |
|---|---|---|---|---|---|
| 30 | N | CH$_2$ | — | 3-methoxyphenyl | 3HCl |
| 31 | N | CH$_2$ | — | 2-methoxyphenyl | 3HCl |
| 32 | N | CH$_2$ | — | 3,4-dimethoxyphenyl | 3HCl |
| 33 | N | CH$_2$ | — | 4-chlorophenyl | 3HCl |
| 34 | N | CH$_2$ | — | 4-methylphenyl | 3HCl |
| 35 | N | COCH$_2$ | CH$_2$CH(phenyl) | phenyl | |
| 36 | N | CH$_2$ | CH$_2$CH$_2$CH(phenyl) | phenyl | 3HCl |
| 37 | N | COCH$_2$ | CH$_2$CH$_2$CH(phenyl) | phenyl | |
| 38 | N | CH$_2$ | CH$_2$CH$_2$CH$_2$CH(phenyl) | phenyl | 3HCl |

TABLE 3-continued
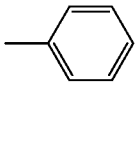
| Ex. No. | Y | Za | Zb | Ar | Additive |
|---|---|---|---|---|---|
| 39 | CH | 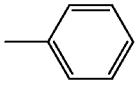 NHCH | — | 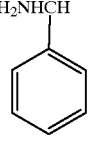 | |
| 40 | CH | 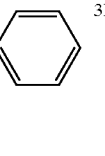 NHCH | — | 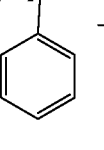 | 3HCl |
TABLE 4
| Ex. No. | R¹ | m | Y | Za | Zb | Ar | Additive |
|---|---|---|---|---|---|---|---|
| 41 | H | 1 | CH | CH$_2$ | 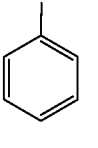 CH$_2$NHCH | 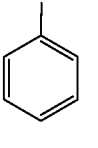 | 3HCl |
| 42 | H | 1 | CH | CH$_2$ | 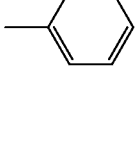 CH$_2$NHCH$_2$CH$_2$CH | 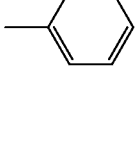 | 3HCl |
| 43 | H | 1 | CH | CH$_2$ | 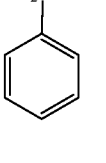 NHCH | 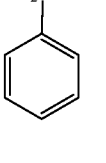 | 2HCl |
| 44 | H | 1 | CH | CH$_2$ | 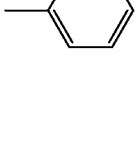 NHCH$_2$CH | 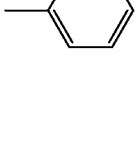 | 3HCl |

TABLE 4-continued
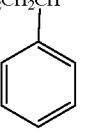
| Ex. No. | R¹ | m | Y | Za | Zb | Ar | Additive |
|---|---|---|---|---|---|---|---|
| 45 | H | 1 | CH | CH₂ | NHCH₂CH₂CH<br>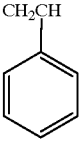 | —⌬ (phenyl) | 2HCl |
| 46 | H | 1 | CH | N(CH₂C₆H₅)CH₂ | CH₂CH<br>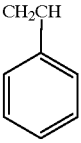 | —⌬ | 3HCl |
| 47 | H | 1 | CH | NHCH₂ | CH₂CH<br>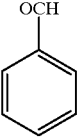 | —⌬ | (COOH)₂ |
| 48 | H | 2 | CH | OCH<br>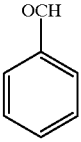 | — | —⌬ | (COOH)₂ |
| 49 | H | 2 | CH | CH₂ | OCH<br>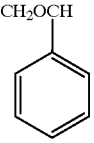 | —⌬ | 2(COOH)₂ |
| 50 | H | 2 | CH | CH₂ | CH₂OCH<br>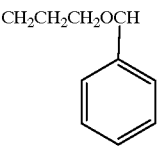 | —⌬ | (COOH)₂ |
| 51 | CH₃CO | 1 | N | CH₂ | CH₂CH₂CH₂OCH<br>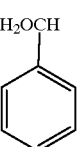 | —⌬ | (COOH)₂ |
| 52 | CH₃CH₂ | 1 | N | CH₂ | CH₂CH₂CH₂OCH<br>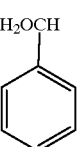 | —⌬ | (COOH)₂ |

TABLE 5

[Structure: 5-amino-4,6-dimethyl-2-methyl-2,3-dihydrobenzofuran with R⁵ at 7-position and -CH₂-N(piperazine)-Y-Za-Zb-Ar substituent]

| Ex. No. | Absolute configuration | R⁵ | Za | Zb | Ar | Additive |
|---|---|---|---|---|---|---|
| 53 | | CH₃ | NHCH-(4-F-C₆H₄) | — | 4-F-C₆H₄ | |
| 54 | | CH₃ | NHCH-(4-OCH₃-C₆H₄) | — | 4-OCH₃-C₆H₄ | |
| 55 | R | CH₃ | NHCH-C₆H₅ | — | C₆H₅ | |
| 56 | S | CH₃ | NHCH-C₆H₅ | — | C₆H₅ | |
| 57 | R | CH₃ | NHCH-C₆H₅ | — | C₆H₅ | H₂SO₄ |
| 58 | S | CH₃ | NHCH-C₆H₅ | — | C₆H₅ | H₂SO₄ |
| 59 | S | CH₃ | NHCH-C₆H₅ | — | C₆H₅ | |

TABLE 5-continued

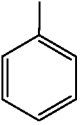

| Ex. No. | Absolute configuration | R⁵ | Za | Zb | Ar | Additive |
|---|---|---|---|---|---|---|
| 60 | | CH(CH₃)₂ | NHCH<br> | — | (phenyl) | |

Formulation Example 1 the compound obtained in Example 5 was dissolved in 30% (w/v) polyethylene glycol 400-saline to prepare a 0.01% solution of the compound. This solution was filtered through a bacterial filter and dispensed into vials, 10 mL per vial, to provide an injectable solution for intravenous administration which contained 1 mg of the compound in each vial.

Formulation Example 2

(S)-2.3-Dihydro-2,4,6,7-tetramethyl-2-[(4-phenyl-1-piperidinyl)methyl]-5-benzofuranamine dihydrochloride was dissolved in 30% (w/v) polyethylene glycol 400-saline to prepare a 0.01% solution of the compound. The solution was filtered through a bacterial filter and dispensed into vials, 10 mL per vial, to provide an injectable solution for intravenous administration which contained 1 mg of the compound in each vial.

Formulation Example 3

| | |
|---|---|
| (1) Compound of Example 5 | 1.0 g |
| (2) Lactose | 60.0 g |
| (3) Corn starch | 35.0 g |
| (4) Gelatin | 3.0 g |
| (5) Magnesium stearate | 2.0 g |

Using 30 mL of 10 wt. % aqueous solution of gelatin (3.0 g as gelatin), a mixture of 1.0 g the compound obtained in Example 5, 60.0 g lactose, and 35.0 g corn starch was granulated through a 1 mm-mesh sieve, dried at 40° C., and resieved. The granules thus obtained were mixed with 2.0 g magnesium stearate and the mixture was compressed. The resulting core tablets were coated with a suspension of sucrose, titanium dioxide, talc, and gum arabic in water. The coated tablets were glazed with beeswax to provide 1000 coated tablets.

Formulation Example 4

The compound obtained in Example 40 was dissolved in 30% (w/v) polyethylene glycol 400-saline to prepare a 0.01% solution of the compound. This solution was filtered through a bacterial filter and dispensed into vials, 10 mL per vial, to provide an injectable solution for intravenous administration which contained 1 mg of the compound in each vial.

Experimental Example 1

A sodium Channel Binding Experiment using the Rat Cerebral Cortex Fraction

Wistar rats (10–15 weeks old) were used in the experiment. The rat was sacrificed by decapitation and the cerebral cortex was immediately isolated. Then, using a homogenizer, the isolated cortex was homogenized in approximately 10 volumes of ice-cooled 0.32 M sucrose-5 mM potassium hydrogen phosphate (pH 7.4, 4° C.) solution. The resulting homogenate was centrifuged at 1,000×g for 10 minutes and the supernatant was further centrifuged at 20,000×g for 15 minutes. The pellet was suspended and washed in 0.32 M sucrose buffer and recentrifuged at 20,000×g for 15 minutes. The residue was recovered. The membrane sample thus obtained was suspended in Na-free assay buffer (50 mM HEPES, 5.4 mM KCl, 0.8 mM MgSO₄, 5.5 mM glucose, 130 mM choline chloride (pH 7.4)) and the binding assay was carried out as follows. To 0.2 mL of the assay buffer containing the test compound, 1 $\mu$M tetrodotoxin, 100 $\mu$g/mL scorpion toxin, and 5 nM [³H] batracotoxinin A20-α-benzoate (34.0 ci/mmol) was added 0.2 mL of the above membrane sample suspension to make a final volume of 0.4 mL and the reaction was carried out in an incubator at 37° C. for 1 hour. This reaction mixture was immediately suction-filtered on a CF/B filter and the filter was washed with 2 mL of wash buffer (5 mM HEPES, 1.8 mM Cacl₂, 0.8 mM MgSO₄, 130 mM choline chloride, and 0.01% BSA(pH 7.4, 4° C.) for a total of 3 times. To this filter was added 4 mL of scintillator and the radioactivity was measured with a liquid scintillation counter. For determination of nonspecific binding, 0.3 mM veratridine was added.

The test compound was added at the final concentrations of 0.03, 0.1, 0.3, 1, 3, 10, and 30 $\mu$M, and the IC₅₀ value was calculated from the inhibition rates.

The results are shown below.

| Compound | IC$_{50}$ ($\mu$M) |
|---|---|
| Example 1 | 0.22 |
| Example 2 | 0.28 |
| Example 3 | 0.26 |
| Example 4 | 0.28 |
| Example 5 | 0.52 |
| Example 6 | 0.79 |
| Example 17 | 0.32 |
| Example 24 | 0.41 |
| Example 25 | 0.34 |
| Example 26 | 0.22 |
| Example 27 | 0.20 |
| Example 28 | 0.22 |
| Example 29 | 0.21 |
| Example 30 | 0.39 |
| Example 31 | 0.49 |
| Example 32 | 0.25 |
| Example 33 | 0.31 |
| Example 34 | 0.42 |
| Example 40 | 0.16 |
| Example 41 | 0.14 |
| Example 42 | 0.16 |
| Reference Example 8 | 0.64 |
| Reference Example 10 | 0.47 |

The above data indicate that the compounds (I) and (Ia) have an affinity for the sodium channel.

INDUSTRIAL APPLICABILITY

The compound (I) of the present invention and compound (Ia) show a high affinity for the sodium channel, particularly for site 2, with a low toxic potential and a low risk for side effects. Therefore, they can act as sodium channel modulators and, hence, are of value as prophylactic and therapeutic agents for central nervous system diseases and disorders such as central nervous system ischemia, central nervous system trauma (e.g. brain trauma, spinal cord injury, whiplash injury, etc.), epilepsy, neurodegenerative diseases (e.g. amyotrophic lateral sclerosis (ALS), Alzheimer's disease, Huntington's chorea, Parkinson's disease, diabetic neuropathy, etc.), vascular dementia (e.g. multi-infarct dementia, Binswanger's disease, etc.), manic-depressive psychosis, depression, schizophrenia, chronic pain, trigeminal neuralgia, migraine and cerebral edema. Furthermore, compounds (I) and (Ia) have excellent antioxidant and dopamine transporter modulating activities and are, therefore, of use as prophylactic and therapeutic drugs for other ischemic cardiovascular diseases (e.g. myocardial infarction, angina pectoris, etc.), and atherosclerosis, among other diseases.

What is claimed is:
1. A compound of the formula:

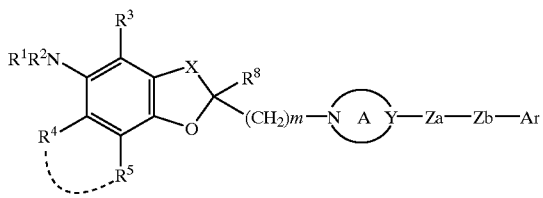

wherein $R^1$ and $R^2$ each is
i) a hydrogen atom,
ii) a $C_{1-6}$ alkyl which may be substituted by 1 to 5 substituents selected from the group consisting of halogen, $C_{3-6}$ cycloalkyl, $C_{2-6}$ alkynyl, $C_{2-6}$ alkenyl, $C_{6-10}$ aryl, $C_{7-11}$ aralkyl, $C_{1-6}$ alkoxy, $C_{6-10}$ aryloxy, $C_{1-6}$ alkyl-carbonyl, $C_{6-10}$ aryl-carbonyl, $C_{1-6}$ alkyl-carbonyloxy, $C_{6-10}$ aryl-carbonyloxy, carboxy, $C_{1-6}$ alkoxy-carbonyl, carbamoyl, amidino, imino, amino, mono-$C_{1-6}$ alkylamino, di-$C_{1-6}$ alkylamino, 3- to 6-membered cyclic amino, $C_{1-3}$ alkylendioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, or
iii) an acyl selected from the group consisting of formyl, $C_{1-6}$ alkyl-carbonyl, $C_{6-10}$ aryl-carbonyl, $C_{6-10}$ aryl-$C_{1-6}$ alkyl-carbonyl, $C_{1-6}$ alkoxy-carbonyl, $C_{6-10}$ aryl-$C_{1-6}$ alkoxy-carbonyl, $C_{1-6}$ alkylsulfonyl, $C_{6-10}$ arylsulfonyl which may be substituted by 1 to 3 $C_{1-6}$ alkyl and $C_{6-10}$ aryl-$C_{1-6}$ alkylsulfonyl;

$R^3$, $R^4$ and $R^5$ each is
i) a $C_{1-6}$ alkyl which may be substituted by 1 to 5 substituents selected from the group consisting of halogen, $C_{3-6}$ cycloalkyl, $C_{2-6}$ alkynyl, $C_{2-6}$ alkenyl, $C_{6-10}$ aryl, $C_{7-11}$ aralkyl, $C_{1-6}$ alkoxy, $C_{6-10}$ aryloxy, $C_{1-6}$ alkyl-carbonyl, $C_{6-10}$ aryl-carbonyl, $C_{1-6}$ alkyl-carbonyloxy, $C_{6-10}$ aryl-carbonyloxy, carboxy, $C_{1-6}$ alkoxy-carbonyl, carbamoyl, amidino, imino, amino, mono-$C_{1-6}$ alkylamino, di-$C_{1-6}$ alkylamino, 3- to 6-membered cyclic amino, $C_{1-3}$ alkylendioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, or
ii) a $C_{1-6}$ alkoxy which may be substituted by 1 to 5 substituents selected from the group consisting of halogen, $C_{3-6}$ cycloalkyl, $C_{2-6}$ alkynyl, $C_{2-6}$ alkenyl, $C_{6-10}$ aryl, $C_{7-11}$ aralkyl, $C_{1-6}$ alkoxy, $C_{6-10}$ aryloxy, $C_{1-6}$ alkyl-carbonyl, $C_{6-10}$ aryl-carbonyl, $C_{1-6}$ alkyl-carbonyloxy, $C_{6-10}$ aryl-carbonyloxy, carboxy, $C_{1-6}$ alkoxy-carbonyl, carbamoyl, amidino, imino, amino, mono-$C_{1-6}$ alkylamino, di-$C_{1-6}$ alkylamino, 3- to 6-membered cyclic amino, $C_{1-3}$ alkylendioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, 'or $R^4$ and $R^5$ form, taken together with the respective adjacent carbon atoms, a 5- or 6-membered carbocyclic group selected from the group consisting of a 6-membered aromatic hydrocarbon ring and a 5- or 6-membered cycloalkene;

$R^6$ is a $C_{1-6}$ alkyl;

Ar is i) a $C_{6-14}$ aryl or ii) a 5-to 10-membered aromatic heterocyclic group containing 1 to 4 hetero atoms selected from nitrogen, sulfur and oxygen in addition to carbon, each of which may be substituted by 1 to 5 substituents selected from the group consisting of group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkyl-sulfonyl, $C_{6-10}$ aryl and $C_{6-10}$ aryloxy;

ring A is a 5- to 8-membered nitrogen-containing heterocyclic ring optionally containing 1 to 4 hetero atoms selected from nitrogen, sulfur and oxygen in addition to nitrogen and carbon, which may be substituted by 1 to 3 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkyl-sulfonyl, $C_{6-10}$ aryl and $C_{6-10}$ aryloxy;

X represents a $C_{1-6}$ alkylene which may be substituted by 1 to 3 substituents selected from the group consisting of halogen, $C_{1-6}$ alkyl, $C_{3-6}$ cycloalkyl, $C_{2-6}$ alkenyl, $C_{2-6}$ alkynyl, $C_{6-14}$ aryl, nitro, cyano, hydroxy, $C_{1-6}$ alkoxy, amino, mono-$C_{1-6}$ alkylamino, di-$C_{1-6}$ alkylamino, $C_{1-6}$ alkyl-carbonyl, $C_{6-10}$ aryloxy and oxo;

Y is i) a nitrogen atom or ii) a group of the formula:

>C(R$^8$)— wherein R$^8$ is a hydrogen atom, halogen, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy;

Za represents a group of the formula:

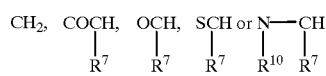

wherein R$^7$ is a hydrogen atom or i) a $C_{6-10}$ aryl or ii) a 5- to 10-membered aromatic heterocyclic group containing 1 to 4 hetero atoms selected from nitrogen, sulfur and oxygen in addition to carbon, each of which may be substituted by 1 to 5 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkyl-sulfonyl, $C_{6-10}$ aryl and $C_{6-10}$ aryloxy;

R$^{10}$ is
i) a hydrogen atom,
ii) a $C_{1-6}$ alkyl, $C_{2-6}$ alkenyl, $C_{2-4}$ alkynyl, $C_{3-6}$ cycloalkyl, $C_{6-14}$ aryl or $C_{7-16}$ aralkyl group which may be substituted by 1 to 5 substituents selected from the group consisting of halogen, $C_{3-6}$ cycloalkyl, $C_{2-6}$ alkynyl, $C_{2-6}$ alkenyl, $C_{6-10}$ aryl, $C_{7-11}$ aralkyl, $C_{1-6}$ alkoxy, $C_{6-10}$ aryloxy, $C_{1-6}$ alkyl-carbonyl, $C_{6-10}$ aryl-carbonyl, $C_{1-6}$ alkyl-carbonyloxy, $C_{6-10}$ aryl-carbonyloxy, carboxy, $C_{1-6}$ alkoxy-carbonyl, carbamoyl, amidino, imino, amino, mono-$C_{1-6}$ alkylamino, di-$C_{1-6}$ alkylamino, 3- to 6-membered cyclic amino, $C_{1-3}$ alkylendioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, or iii) an acyl selected from the group consisting of formyl, $C_{1-6}$ alkyl-carbonyl, $C_{6-10}$ aryl-carbonyl, $C_{6-10}$ aryl-$C_{1-6}$ alkyl-carbonyl, $C_{1-6}$ alkoxy-carbonyl, $C_{6-10}$ aryl-$C_{1-6}$ alkoxy-carbonyl, $C_{1-6}$ alkylsulfonyl, $C_{6-10}$ arylsulfonyl which may be substituted by 1 to 3 $C_{1-6}$ alkyl and $C_{6-10}$ aryl-$C_{1-6}$ alkylsulfonyl; and Zb is a bond or a divalent aliphatic hydrocarbon group selected from the group consisting of (i) a $C_{1-8}$ alkylene, (ii) a $C_{2-8}$ alkenylene, (iii) a $C_{2-8}$ or (iv) a group of the formula: —$(CH_2)_p$—M—$(CH_2)_q$— wherein p and q each is an integer of 0 to 8 and p+q is an integer of 1 to 8; M is O, NR$^9$, S, SO or SO$_2$, wherein R$^9$ is a hydrogen atom, $C_{1-6}$ alkyl, $C_{3-6}$ cycloalkyl, $C_{6-14}$ aryl, $C_{7-11}$ aralkyl or an acyl selected from the group consisting of formyl, $C_{1-6}$ alkyl-carbonyl, $C_{6-10}$ aryl-carbonyl, $C_{6-10}$ aryl-$C_{1-6}$ alkyl-carbonyl, $C_{1-6}$ alkoxy-carbonyl, $C_{6-10}$ aryl-$C_{1-6}$ alkoxy-carbonyl, $C_{1-6}$ alkylsulfonyl, $C_{6-10}$ arylsulfonyl which may be substituted by 1 to 3 $C_{1-6}$ alkyl and $C_{6-10}$ aryl-$C_{1-6}$ alkylsulfonyl, each of which divalent group may be substituted by 1 to 5 substituents selected from the group consisting of halogen, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{6-14}$ aryl, $C_{7-11}$ aralkyl, $C_{6-10}$ aryloxy, oxo formyl, $C_{1-6}$ alkyl-carbonyl, $C_{6-10}$ aryl-carbonyl, $C_{6-10}$ aryl-$C_{1-6}$ alkyl-carbonyl, $C_{1-6}$ alkoxy-carbonyl, $C_{6-10}$ aryl $C_{1-6}$ alkoxy-carbonyl, $C_{1-6}$ alkylsulfonyl, $C_{6-10}$ arylsulfonyl which may be substituted by 1 to 3 $C_{1-6}$ alkyl and $C_{6-10}$ aryl-$C_{1-6}$ alkylsulfonyl; and m represents an integer of 1 to 3, or a salt thereof.

2. A compound claimed in claim 1 wherein Za is a group of the formula:

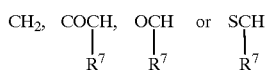

wherein R$^7$ has the same meaning as defined in claim 1.

3. A compound claimed in claim 1 wherein R$^1$ and R$^2$ each is a hydrogen atom.

4. A compound claimed in claim 1 wherein R$^3$, R$^4$, and R$^5$ each is $C_{1-6}$ alkyl.

5. A compound claimed in claim 1 wherein R$^6$ is $C_{1-6}$ alkyl.

6. A compound claimed in claim 1 wherein Ar is a $C_{6-14}$ aryl which may be substituted by 1 to 3 substituents selected from the group consisting of halogen, $C_{1-6}$ alkyl and $C_{1-6}$ alkoxy.

7. A compound claimed in claim 1 wherein ring A is a 6-membered nitrogen-containing heterocyclic which may be substituted by 1 to 3 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy.

8. A compound claimed in claim 1 wherein X is methylene.

9. A compound claimed in claim 1 wherein Y is CH.

10. A compound claimed in claim 1 wherein Za is a group of the formula:

wherein respective symbols have the same meanings as defined in claim 1.

11. A compound claimed in claim 1 wherein $R^7$ is $C_{6-10}$ aryl which may be substituted by 1 to 5 substituents selected from the group consisting of halogen, $C_{1-3}$ alkylenedioxy, nitro, cyano, $C_{1-6}$ alkyl which may be halogenated, $C_{3-6}$ cycloalkyl, $C_{1-6}$ alkoxy which may be halogenated, $C_{1-6}$ alkylthio which may be halogenated, hydroxy, amino, mono-$C_{1-6}$ alkylamino, di-$C_{1-6}$ alkylamino, $C_{1-6}$ alkyl-carbonyl, carboxy, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, sulfo, $C_{1-6}$ alkylsulfonyl, $C_{6-10}$ aryl and $C_{6-10}$ aryloxy.

12. A compound claimed in claim 1 wherein $R^{10}$ is a hydrogen atom.

13. A compound claimed in claim 1 wherein Zb is a bond.

14. A compound claimed in claim 1 wherein m is 1.

15. A compound claimed in claim 1 wherein $R^1$ and $R^2$ each is a hydrogen atom;

$R^3$, $R^4$, $R^5$, and $R^6$ each is a $C_{1-6}$ alkyl;

Ar is a phenyl which may be substituted by 1 to 3 substituents selected from the group consisting of halogen, $C_{1-6}$ alkyl and $C_{1-6}$ alkoxy;

ring A is a 6-membered nitrogen-containing heterocyclic ring;

X is methylene;

Y is CH or N;

Za is a group of the formula:

wherein $R^{7'}$ is a phenyl which may be substituted by 1 to 3 substituents selected from the group consisting of halogen, $C_{1-6}$ alkyl and $C_{1-6}$ alkoxy; and $R^{10'}$ is a hydrogen atom;

Zb is a bond or a $C_{1-6}$ alkylene which may be substituted by a $C_{6-10}$ aryl; and m is 1 or 2.

16. A compound claimed in claim 1 wherein $R^1$ and $R^2$ each is a hydrogen atom;

$R^3$, $R^4$, $R^5$, and $R^6$ each is a $C_{1-6}$ alkyl;

Ar is a $C_{6-10}$ aryl which may be substituted by a methylenedioxy;

ring A is a 6-membered nitrogen-containing heterocyclic ring;

X is methylene;

Y is CH or N;

Za is a group of the formula: $CH_2$,

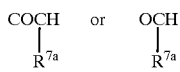

wherein $R^{7a}$ is a hydrogen atom or $C_{6-10}$ aryl;

Zb is a bond or a (i) $C_{1-6}$ alkylene or (ii) $C_{2-6}$ alkenylene group which may be substituted by a $C_{6-10}$ aryl; and m is 1.

17. A compound claimed in claim 1 wherein $R^{1'}$ and $R^2$ each is hydrogen;

$R^3$, $R^4$, $R^5$, and $R^6$ each is a $C_{1-6}$ alkyl;

Ar is a $C_{6-10}$ aryl which may be substituted by 1 to 3 substituents selected from the group consisting of halogen, methylenedioxy, $C_{1-6}$ alkyl and $C_{1-6}$ alkoxy;

ring A is a 6-membered nitrogen-containing heterocyclic ring;

X is methylene;

Y is CH or N;

Za is a group of the formula:

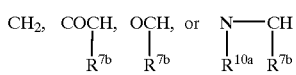

wherein $R^{7b}$ is a hydrogen atom or a $C_{6-10}$ aryl which may be substituted by a halogen; and $R^{10a}$ is a hydrogen atom or a $C_{7-11}$ aralkyl;

Zb is a bond or a divalent group selected from the group consisting of (i) a $C_{1-6}$ alkylene, (ii) a $C_{2-6}$ alkenylene and (iii) a group of the formula:

—$(CH_2)_{p'}$—M'—$(CH_2)_{q'}$— wherein p' and q' each is an integer of 0 to 5, p'+q' is an integer of 1 to 6 and M' is O or NH, each of which divalent group may be substituted by a $C_{6-10}$ aryl; and m is 1 or 2.

18. A compound claimed in claim 1 which is

1-[(5-amino-2,3-dihydro-2,4,6,7-tetramethylbenzofuran-2-yl)methyl]-N-(diphenylmethyl)-4-piperidinamine, (−)-1-[(5-amino-2,3-dihydro-2,4,6,7-tetramethylbenzofuran-2-yl)methyl]-N-(diphenylmethyl)-4-piperidinamine, (+)-1-[(5-amino-2,3-dihydro-2,4,6,7-tetramethylbenzofuran-2-yl)methyl]-N-(diphenylmethyl)-4-piperidinamine, 1-[(5-amino-2,3-dihydro-7-isopropyl-2,4,6-trimethylbenzofuran-2-yl)methyl]-N-(diphenylmethyl)-4-piperidinamine, (−)-1-[(5-amino-2,3-dihydro-7-isopropyl-2,4,6-trimethylbenzofuran-2-yl)methyl]-N-(diphenylmethyl)-4-piperidinamine, (+)-1-[(5-amino-2,3-dihydro-7-isopropyl-2,4,6-trimethylbenzofuran-2-yl)methyl]-N-(diphenylmethyl)-4-piperidinamine, or a salt thereof.

19. A process for producing a compound claimed in claim 1 which comprises (i) reacting a compound of the formula:

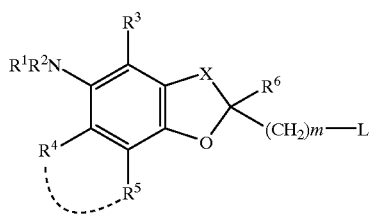

wherein L represents a leaving group; the other symbols have the same meanings as defined in claim 1, or a salt thereof with a compound of the formula:

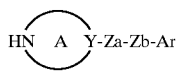

wherein the respective symbols have the same meanings as defined in claim 1, or a salt thereof;

(ii) subjecting a compound of the formula:

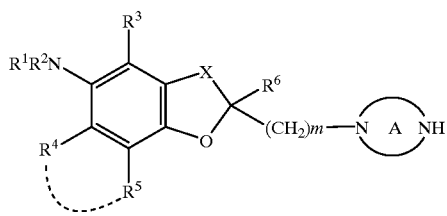

wherein the respective symbols have the same meanings as defined in claim 1, or a salt thereof to (a) alkylation, (b) acylation or (c) acylation followed by reduction;

(iii) reacting a compound of the formula:

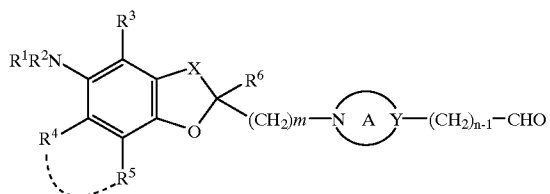

wherein n represents an integer of 1 to 4; the other symbols have the same meanings as defined in claim 1, or a salt thereof with a compound of the formula:

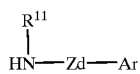

wherein $R^{11}$ represents a hydrogen atom or a hydrocarbon group which may be substituted; Zd represents a divalent aliphatic hydrocarbon group which may be substituted and may contain oxygen, nitrogen or sulfur;

Ar has the same meaning as defined in claim 1, or a salt thereof, (iv) reacting a compound of the formula:

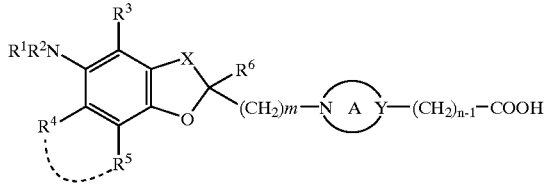

wherein the respective symbols have the same meanings as defined above, or a salt thereof with a compound of the formula:

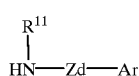

wherein the respective symbols have the same meanings as defined above, or a salt thereof, optionally followed by reduction; or (v) subjecting a compound of the formula:

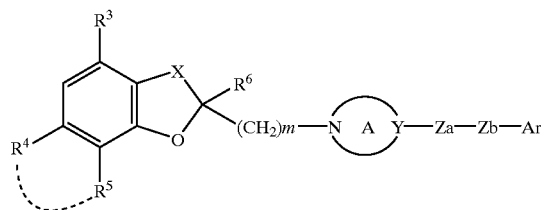

wherein the respective symbols have the same meanings as defined in claim 1, or a salt thereof to (a) nitration followed by reduction or (b) diazo coupling reaction followed by reduction.

20. A pharmaceutical composition which comprises an affective amount of the compound claimed in claim 1, if necessary together with a pharmaceutically acceptable carrier.

21. A composition claimed in claim 20 which is for modulating sodium channel.

22. A composition claimed in claim 21 which is for the prophylaxis or treatment of central nervous system ischemia, central nervous system trauma, neurodegenerative disease or cerebral edema.

23. A method for modulating sodium channel in a mammal in need thereof which comprises administering to such mammal an effective amount of a compound claimed in claim 1 or a pharmaceutically acceptable salt thereof with a pharmaceutically acceptable excipient, carrier or diluent.

* * * * *

UNITED STATES PATENT AND TRADEMARK OFFICE
CERTIFICATE OF CORRECTION

PATENT NO. : 6,172,085 B1  
DATED : January 9, 2001  
INVENTOR(S) : Minoru Ohkawa.

Page 1 of 1

It is certified that error appears in the above-identified patent and that said Letters Patent is hereby corrected as shown below:

ABSTRACT and claim 1,
Please note the formula of the compound has an erroneous expression. The symbol "$R^8$" in the formula should read -- $R^6$ --.

Signed and Sealed this

Twenty-fifth Day of December, 2001

*Attest:*

JAMES E. ROGAN
*Attesting Officer*  *Director of the United States Patent and Trademark Office*